(12) United States Patent
Hostetter et al.

(10) Patent No.: US 9,920,113 B2
(45) Date of Patent: Mar. 20, 2018

(54) ANTIBODY BINDING MICROBIAL HEPARIN BINDING MOTIF TO RETARD OR PREVENT MICROBIAL BIOFILM FORMATION ON IMPLANTED MEDICAL DEVICES

(71) Applicants: Children's Hospital Medical Center, Cincinnati, OH (US); University of Cincinnati, Cincinnati, OH (US); Yale University, New Haven, CT (US)

(72) Inventors: Margaret K. Hostetter, Cincinnati, OH (US); Long Lu, Cincinnati, OH (US); Julianne Vernadette Green, Cincinnati, OH (US); Alexey Porollo, Cincinnati, OH (US); Kris I. Orsborn, Terrace Park, OH (US); Khoon Ghee Queenie Tan, Durham, NC (US); Kenneth Greis, Fort Thomas, KY (US); David Andes, Madison, WI (US)

(73) Assignees: CHILDREN'S HOSPITAL MEDICAL CENTER, Cincinnati, OH (US); UNIVERSITY OF CINCINNATI, Cincinnati, OH (US); YALE UNIVERSITY, New Haven, CT (US)

( * ) Notice: Subject to any disclaimer, the term of this patent is extended or adjusted under 35 U.S.C. 154(b) by 27 days.

(21) Appl. No.: 15/165,102

(22) Filed: May 26, 2016

(65) Prior Publication Data
US 2016/0257734 A1 Sep. 8, 2016

Related U.S. Application Data

(60) Division of application No. 14/518,051, filed on Oct. 20, 2014, now Pat. No. 9,409,975, which is a continuation-in-part of application No. PCT/US2013/031499, filed on Mar. 14, 2013.

(60) Provisional application No. 61/636,243, filed on Apr. 20, 2012.

(51) Int. Cl.
C07K 16/14 (2006.01)
C07K 7/08 (2006.01)
C07K 16/12 (2006.01)
A61K 39/00 (2006.01)

(52) U.S. Cl.
CPC .......... *C07K 16/14* (2013.01); *C07K 7/08* (2013.01); *C07K 16/1271* (2013.01); *A61K 39/00* (2013.01); *A61K 2039/505* (2013.01); *A61K 2039/575* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| 5,505,945 A * | 4/1996 | Gristina ............. A61K 39/44 424/130.1 |
| 5,886,151 A * | 3/1999 | Hostetter ............. C07K 14/40 424/274.1 |
| 6,346,411 B1 | 2/2002 | Hostetter et al. |
| 6,734,162 B2 | 5/2004 | Van Antwerp et al. |
| 6,774,219 B2 | 8/2004 | Hostetter et al. |
| 7,138,502 B2 | 11/2006 | Hostetter et al. |
| 7,241,613 B1 | 7/2007 | Willins et al. |
| 7,595,374 B1 | 9/2009 | Chang et al. |
| 2003/0082680 A1 | 10/2003 | Hostetter et al. |
| 2007/0027309 A1 * | 2/2007 | Weinstock ........... C12Q 1/6895 536/23.7 |
| 2007/0116706 A1 | 5/2007 | Hostetter et al. |
| 2011/0189183 A1 | 8/2011 | Williamson et al. |

FOREIGN PATENT DOCUMENTS

| WO | 2006/024631 | 3/2006 |
| WO | 2013/158276 | 10/2013 |

OTHER PUBLICATIONS

Ramage et al. 2006 (Candida biofilms on implanted biomaterials: a clinically significant problem; FEMS Yeast Res 6:979-986).*
International Search Report for PCT/US2013/031499, dated Jul. 9, 2013 (5 pages).
Written Opinion for PCT/US2013/031499, dated Jul. 9, 2013 (5 pages).
Advani et al. Central Line-Associated Bloodstream Infection in Hospitalized Children with Peripherally Inserted Central Venous Catheters: Extending Risk Analyses Outside the Intensive Care Unit. Clinical Infectious Diseases vol. 52, No. 9 (2011), pp. 1108-1115.
Alberti-Segui et al. Identification of potential cell-surface proteins in Candida albicans and investigation of the role of a putative cell-surface glycosidase in adhesion and virulence. Yeast, vol. 21 (2004), pp. 285-302.
Almirante et al. Epidemiology and Predictors of Mortality in Cases of Candida Bloodstream Infection: Results from Population-Based Surveillance, Barcelona, Spain, from 2002 to 2003. Journal of Clinical Microbiology, vol. 43, No. 4 (2005), pp. 1829-1835.
Alvarez-Dominguez et al. Host Cell Heparan Sulfate Proteoglycans Mediate Attachmant and Entry of Listeria monocytogenes, and the Listerial Surface Protein ActA Is Involved in Heparan Sulfate Receptor Recognition. Infection and Immunity, vol. 65, No. (1997), pp. 78-88.
Anderson et al. Antimicrobial activities of heparin-binding peptides. Eur. J. Biochem. 271, 1219-1226 (2004).
Andes et al. Development and Characterization of an In Vivo Central Venous Catheter Candida albicans Biofilm Model. Infection and Immunity, vol. 72, No. 10 (2004), pp. 6023-6031.
Barth et al. Cellular Binding of Hepatitis C Virus Envelope Glycoprotein E2 Requires Cell Surface Heparan Sulfate. Journal of Biological Chemistry, vol. 278, No. 42 (2003), pp. 41003-41012.

(Continued)

*Primary Examiner* — Mary Lyons
(74) *Attorney, Agent, or Firm* — Thompson Hine LLP

(57) ABSTRACT

Methods and reagents for ameliorating biofilm formation on a surface of an indwelling or implanted device in a patient resulting in decreased virulence of microorganisms such as *Candida* species and/or *Staphylococcus* species.

6 Claims, 21 Drawing Sheets

(56) References Cited

OTHER PUBLICATIONS

Beck-Sague et al. Secular Trends in the Epidemiology of Nosocomial Fungal Infections in the United States, 1980-1990. Journal of Infectious Diseases 1993; 167:1247-51.
Bendtsen et al. Improved Prediction of Signal Peptides: SignalIP 3.0. J. Mol. Biol. vol. 340 (2004), pp. 783-795.
Brown et al. Tolerance to single, but multiple, amino acid replacements in Antibody VH CDR2; J. Immunol.; 156(9):3285-91 at 3290 (May 1996).
Capila and Linhardt. Heparin Protein Interactions. Angew. Chem. Int. Ed., vol. 41 (2002), 390-412.
Cardin and Weintraub. Molecular Modeling of Protein-Glycosaminoglycan Interactions. Arterioscler Thromb Vasc Biol. 9 (1989) 21-32.
Carrasco et al. Evaluation of a triple-lumen central venous heparin-coated catheter versus a catheter coated with chlorhexidine and silver sulfadiazine in critically ill patients. Intensive Care Med vol. 30 (2004), pp. 633-638.
Srinivasan et al. Vital Signs: Central Line-Associated Blood Stream Infections—United States, 2001, 2008, and 2009. Morbidity and Mortality Weekly Report. 60 (2011) 243-248.
Chaffin. Candida albicans Cell Wall Proteins. Microbiology and Molecular Biology Reviews. 7 (2008) 495-544.
Chandra et al. Biofilm Formation by the Fungal Pathogen Candida albicans: Development, Architecture, and Drug Resistance. Journal of Bacteriology, 183 (2001) 5385-5394.
Chen et al. Dengue virus infectivity depends on envelope protein binding to target cell heparin sulfate. Nature Medicine, vol. 3, No. 8 (1997), pp. 866-871.
Cormack. Directed Mutagenesis Using the Polymerase Chain Reaction. Current Protocols in Molecular Biology (1997), Supplement 37, 8.5.1-8.5.10.
Devore-Carter et al. Superantigen-Like Effects of a Candida albicans Polypeptide. J Infect Dis. vol. 197, No. 7, (2008), pp. 981-989 Author Manuscript (26 pages).
Diskin. Catheter-related sepsis in dialysis patients. QJM, 100 (2007) 666-667 (3 pages total).
Downes et al. Polymicrobial Bloodstream Infections among Children and Adolescents with Central Venous Catheters Evaluated in Ambulatory Care. Clinical Infectious Diseases, vol. 46 (2008), pp. 387-394.
Duncan et al. Lcl of Legionella pneumophila Is an Immunogenic GAG Binding Adhesin That Promotes Interactions with Lung Epithelial Cells and Plays a Crucial Role in Biofilm Formation. Infection and Immunity, vol. 79, No. 6 (2011), pp. 2168-2181.
Eismann et al. Peroxiredoxin-6 protects against mitochondrial dysfunction and liver injury during ischemia-reperfusion in mice. Am J Physiol Gastrointest Liver Physio, vol. 296 (2009), pp. G266-G274.
Fagan et al. The Hek Outer Membrane Protein of *Escherichia coli* Strain RS218 Binds to Proteoglycan and Utilizes a Single Extracellular Loop for Adherence, Invasion, and Autoaggregation. Infect. Immun. 76 (2008) 1135-1142.
Fankhauser and Mäser. Identification of GPI anchor attachment signals by a Kohonen self-organizing map. Bioinformatics 21 (2005) 1846-1852.
Farshi et al. Dual Roles of the Cardin-Weintraub Motif in Multimeric Sonic Hedgehog. Journal of Biological Chemistry, vol. 286, No. 26 (2011), pp. 23608-23619.
Finkel and Mitchell. Genetic control of Candida albicans biofilm development. Nature Reviews | Microbiology, vol. 9, (2011), pp. 109-118.
Fleckenstein et al. Interaction of an Outer Membrane Protein of Enterotoxigenic *Escherichia coli* with Cell Surface Heparan Sulfate Proteoglycans. Infect. Immun. 2002, 70(3):1530-1537.
Frevert et al. Malaria Circumsporozoite Protein Binds to Heparan Sulfate Proteoglycans Associated with the Surface Membrane of Hepatocytes. J. Exp. Med., vol. 177 (1993), pp. 1287-1298.
Gale et al. Linkage of Adhesion, Filamentous Growth, and Virulence in Candida albicans to a Single Gene, INT1. Science, vol. 279, (1998), pp. 1355-1358.
Guerino et al. HLA class II transgenic mice develop a safe and long lasting immune response against StreptInCor, an anti-group A *Streptococcus* vaccine candidate. Vaccine vol. 29 (2011), pp. 8250-8256.
Hoffman Winston. A ten-minute DNA preparation from yeast efficiently releases autonomous plasmids for transformation of *Escherichia coli*. Gene vol. 51 (1987), pp. 267-212.
Hostetter. The iC3b receptor of Candida albicans and its Roles in Pathogenesis. Vaccine. Dec. 30, 2008; 26(Supp 8): 1108-1112. Author manuscript 11 pages.
Isemann, et al. Effect of heparin and other factors associated with complications of peripherally inserted central venous catheters in neonates. Journal of Perlnatology. Epub Feb. 2, 2012, 32(11):856-86o.
Jenkins, et al. Two Domains within the Mycoplasma hyopneumoniae Cilium Adhesin Bind Heparin. Infect. Immun. 2006, 74(1):481-487.
Kao et al. The Epidemiology of Candidemia in Two United States Cities: Results of a Population-Based Active Surveillance. Clinical Infectious Diseases 1999;29:1164-1170.
Li et al. Binding of von Willebrand factor by coagulasenegative staphylococci. J. Med. Microbiol. vol. 49 (2000), pp. 217-225.
Lopez, et al. Antibodies in the protection against mycobacterial infections: what have we learned? Procedia in Vaccinology 2 (20 10) 172-177.
Macdonald et al. Risk Factors for Candidemia in a Children's Hospital. Clinical Infectious Diseases vol. 26 (1998), pp. 642-645.
Mao et al. C-Terminal Signals Regulate Targeting of Glycosylphosphatidylinositol-Anchored Proteins to the Cell Wall or Plasma Membrane in Candida albicans. Eukaryotic Cell, vol. 7, No. 11 (2008), pp. 1906-1915.
Margalit et al. Comparative Analysis of Structurally Defined Heparin Binding Sequences Reveals a Distinct Spatial Distribution of Basic Residues. Journal of Biological Chemistry, vol. 268, No. 26 (1993), pp. 19228-19231.
Marson et al. Development of a microtiter plate-based glycosaminoglycan array for the investigation of glycosaminoglycan-protein interactions. Glycobiology. vol. 19, No. 12 (2009), pp. 1537-1546. Author manuscript 19 pages.
Mermel et al. Clinical Practice Guidelines for the Diagnosis and Management of Intravascular Catheter-Related Infection: 2009 Update by the Infectious Diseases Society of America. Clinical Infectious Diseases vol. 49 (2009), pp. 1-45.
Miceli, et al. In Vitro Analyses of the Effects of Heparin and Parabens on *Candida albicans* Biofilms and Planktonic Cells. Antimicrobial Agents and Chemotherapy. 56 (2012)148-53.
Morgan et al. Excess Mortality, Hospital Stay, and Cost Due to Candidemia: A Case-Control Study Using Data from Population-Based Candidemia Surveillance. Infection Control and Hospital Epidemiology, 26 (2005) 540-547.
NCBI Direct Submission XP_720565.1. Integrin-line protein [Candida albicans SC5314]. May 28, 2008. Retrieved from the internet http://www.ncbi.nlm.nih.gov/protein/XP_720565.1 (2 pages).
Nobile and Mitchell. Genetics and genomics of Candida albicans biofilm formation. Cellular Microbiology, vol. 8, No. 9 (2006), pp. 1382-1391.
Nobile et al. A Recently Evolved Transcriptional Network Controls Biofilm Development in Candida albicans. Cell. 148 (2012) 126-138. Author manuscript 25 pages.
Osmond et al. Protein-heparin interactions measured by BIAcore 2000 are affected by the method of heparin immobilization. Analytical Biochemistry vol. 310 (2002), pp. 199-207.
Pappas et al. A Prospective Observational Study of Candidemia: Epidemiology, Therapy, and Influences on Mortality in Hospitalized Adult and Pediatric Patients. Clinical Infectious Diseases vol. 37 (2003), pp. 634-643.
Pascu et al. Staphylococci Bind Heparin-Binding Host Growth Factors. Current Microbiology vol. 32 (1996), pp. 201-207.

(56) References Cited

OTHER PUBLICATIONS

Paulsson et al. Adherence of coagulase-negative staphylococci to heparin and other glycosaminoglycans immobilized on polymer surfaces. Journal of Biomedical Materials Research, vol. 28 (1994), pp. 311-317.

Pfaffl. A new mathematical model for relative quantification in real-time RT-PCR. Nucleic Acids Research, vol. 29, No. 9 (2001), pp. 2002-2007.

Pierleoni et al. PredGPI: a GPI-anchor predictor. BMC Bioinformatics, vol. 9 (2008), 392 (11 pages).

Rusnati et al. Multiple Interactions of HIV-I Tat Protein with Size-defined Heparin Oligosaccharides. Journal of Biological Chemistry, vol. 274, No. 40 (1999), pp. 28198-28205.

Saiman et al. Risk factors for candidemia in Neonatal Intensive Care Unit patients. Pediatr Infect Dis J, vol. 19 (2000), pp. 319-324.

Sangupta, et al. Ent!]moeba histolytica: Monoclonal Antibody against the beta 1 integrin-like Molecule (140 kDa) Inhibits Cell Adhesion to Extracellular Matrix Components. Experimental Parasitology 98, 83-89 (2001).

Saphire et al. Host cyclophilin A mediates HIV-1 attachment to target cells via heparans. EMBO journal, vol. 18, No. 23 (1999), pp. 6771-6785.

Schenerman et al. Comparability Testing of a Humanized Monoclonal Antibody (Synagis®) to Support Cell Line Stability, Process Validation, and Scale-Up for Manufacturing. Biologicals, vol. 27 (1999), pp. 203-215.

Shanks et al. Heparin Stimulates *Staphylococcus aureus* Biofilm Formation. Infection and Immunity, vol. 73, No. 8 (2005), pp. 4596-4606.

Shuklaet al. A Novel Role for 3-O-Sulfated Heparan Sulfate in Herpes Simplex Virus 1 Entry. Cell, vol. 99, (1999), pp. 13-22.

Torrent et al. The "CPC Clip Motif": A Conserved Structural Signature for Heparin-Binding Proteins. PLoS One, vol. 7, No. 8 (2012), e42692, (8 pages).

Villeponteau. Heparin increases chromatin accessibility by binding the trypsin-sensitive basic residues in histones. Biochem. J. (1992) 288, 953-958.

Williams and Straus. Specificity and Affinity of Binding of Herpes Simplex Virus Type 2 Glycoprotein B to Glycosaminoglycans. Journal of Virology, vol. 71, No. 2 (1997), pp. 1375-1380.

Wilson et al. Rapid Hypothesis Testing with Candida albicans through Gene Disruption with Short Homology Regions. J. Bacteriology, vol. 181, No. 6 (1999), pp. 1868-1874.

Xiao et al. Activation-dependent Conformational Changes in β-Arrestin 2. Journal of Biological Chemistry 279 (2004) 55744-55753.

Harrop, et al. Heparin specifically inhibits binding of V3 loop antibodies to HIV-1 gp120, an effect potentiated by CD4 binding. AIDS, 1994, vol. 8, No. 2, pp. 183-192.

Lortat-Jacob and Grimaud. Interferon-Gamma C-Terminal Function: New Working Hypothesis. Heparan Sulfate and Heparin, New Targets for IFN-Gamma, Protect, Relax the Cytokine and Regulate Its Activity. Cellular and Molecular Biology 37(3), 253-260, 1991.

Hamilton, et al. Heparin sodium versus 0.9% sodium chloride injection for maintaining patency of indwelling intermittent infusion devices. Clinical Pharmacy 7 (1988) 439-43.

Klotz and Smith. Glycosaminoglycans inhibit Candida albicans adherence to extracellular matrix proteins. FEMS Microbiology Letters 99(1992) 205-208.

Drew. Liquid Culture. Chapter 10 in Manual of Methods for General Bacteriology 1981 pp. 151-178.

Sobel, et al. Localization and Characterization of a Heparin Binding Domain Peptide of Human von Willebrand Factor. J. Biol. Chem. 267 (1992) 8857-8862.

Spear et al. Heparan sulfate glycosaminoglycans as primary cell surface receptors for herpes simplex virus. Adv. Exp Med Biol 313 (1992) 341-353.

\* cited by examiner

| Doubling Times (hours) at 30°C | | |
|---|---|---|
|  | No Heparin | + Heparin |
| YPD | 1.70 | 1.69 |
| RPMI-HEPES | 3.56 | 3.75 |
| RPMI-MOPS | 3.58 | 3.51 |
| CSM | 1.82 | 1.79 |

| Percent Hyphae | | |
|---|---|---|
|  | No Heparin | + Heparin |
| YPD, 30 °C, 2.5 hours | 0.13 | 0.09 |
| RPMI-HEPES, 37 °C, 1 hour | 7.37 | 5.01 |

| Optical Density$_{595}$ at 10,000 CFU/well *C. albicans* | | | | | |
|---|---|---|---|---|---|
| Heparin units/well (μg/well) | 1.25 (6.3) | 2.5 (12.5) | 5.0 (25.0) | 10.0 (50.0) | 20.0 (100.0) |
| Mean OD$_{595}$ (+/- SD) | 0.53 (+/- 0.05) | 0.51 (+/- 0.03) | 0.48 (+/- 0.04) | 0.51 (+/- 0.02) | 0.49 (+/- 0.03) |

| Motif 1 | Motif 2 | Motif 3 | Motif 4 | Motif 5 |
|---|---|---|---|---|
| 804 QKKHQIHK | 1383 THKGRF | 1530 MKRGKP | 1593 FKKRFFKL | 1612 SHKTRA |

↓ ↓

804 QAAHQIHK        1593 FKAAFFKL

1593 FKKRFFKL
(Motif 4)

ANTIBODY BINDING MICROBIAL HEPARIN BINDING MOTIF TO RETARD OR PREVENT MICROBIAL BIOFILM FORMATION ON IMPLANTED MEDICAL DEVICES

This application claims priority to co-pending U.S. application Ser. No. 14/518,051 filed Oct. 20, 2014, which is a continuation-in-part of International Application Serial No. PCT/US2013/031499 filed Mar. 14, 2013, which claims priority to U.S. application Ser. No. 61/636,243 filed Apr. 20, 2012, each of which is expressly incorporated by reference herein in its entirety.

A novel interaction between *Candida albicans* (*C. albicans*) surface proteins and heparin, a drug commonly used in patients at risk for catheter-associated biofilms and candidemia, is disclosed with an antibody that reduced or prevented a microorganism surface protein from binding to heparin, and reduced catheter-associated biofilm formation, where the reduction in biofilm formation can reduce the microorganism's virulence in a patient, with reduction encompassing any level of decrease.

Heparin is a highly sulfated, non-branched, anionic disaccharide composed of uronic acid, predominantly iduronic acid, in 1,4 linkage with glucosamine. Heparin is a known anticoagulant that is often infused in indwelling catheters to prevent the blood flowing through the catheter from clotting. Heparan sulfate is composed of the same disaccharide but is less sulfated and has a more varied structure than heparin. Heparan sulfate linked to core proteins, such as syndecans or glypicans, forms heparan sulfate proteoglycans (HSPGs). HSPGs are widely expressed on mammalian cell surfaces and in the extracellular matrix. Heparin binding motifs can bind to both heparin and heparan sulfate.

Several microbial proteins bind heparin and heparan sulfate, e.g., HIV-1 gp120, CypA, and Tat; hepatitis C envelope glycoprotein E2; herpes simplex virus glycoproteins B, C, and D; dengue virus envelope protein; *Plasmodium falciparum* circumsporozoite (CS) protein, *Listeria monocytogenes* ActA, and Lcl of *Legionella pneumophila* (1-11). Such microbial protein interactions with surface HSPGs typically promote binding and entry of the microbial organism into the mammalian cell (except for HIV-1 gp120 and Tat), but the mechanisms by which individual microbial proteins recognize heparin or heparan sulfates are largely undefined. Positively charged tripeptides containing Lys or Arg in the amino terminus of *L. monocytogenes* ActA (aa 40-230) and in *L. pneumophila* Lcl (aa 69-349) were shared with tripeptides in a number of heparin-binding mammalian proteins such as EGF-like growth factor and vonWillebrand factor, but the precise amino acids that mediated binding to heparin were not defined for ActA or Lcl (10-11).

Eukaryotic proteins that bind heparin express either linear or conformational heparin binding motifs (HBM). Linear heparin binding motifs are short, conserved peptides containing both basic (B) and hydropathic (X) amino acids in specific patterns first identified by Cardin (XBBXBX) and Weintraub (XBBBXXBX) and subsequently expanded by Sobel (XBBBXXBBBXXBBX) (12-14). Molecular modeling studies suggested that basic amino acids such as lysine, arginine, and histidine were critical for interaction with anionic sulfate or carboxylate groups in heparin through electrostatic and hydrogen bonds. For example, substituting alanine for basic amino acids in linear HBM in the morphogen sonic hedgehog abolished binding to heparin (15). However, because many heparin-binding proteins failed to exhibit linear motifs, the concept of spatial orientation of basic residues was propounded (16). The CPC clip motif, a structural signature in which two cationic residues surround one polar residue, was conserved in eukaryotic heparin binding proteins, as well as in vaccinia complement protein and papillomavirus 18 capsid protein (17).

Because of its propensity to form biofilms in implanted medical devices such as indwelling central venous catheters, *Candida albicans* (*C. albicans*) is a leading pathogen in infections of indwelling catheters. A biofilm is a multilayered structure of microbes embedded in a polysaccharide matrix that forms on central venous catheters as well as implanted prosthetic joints, contact lenses, and other such medical devices (18, 19). A biofilm is undesirable because antibiotics and host defenses cannot penetrate it, thus a biofilm prevents elimination of microorganisms that have attached or adhered to a surface of an implanted medical device. For example, because of the high flow-through in a central venous catheter, sessile projections from a biofilm break off and are carried into the bloodstream to cause infection that can be carried by the blood to other sites in the body.

Heparin is a known anticoagulant, and catheters are often infused with heparin to prevent blood flowing through the catheter from clotting (20). Because heparin inhibited attachment of *C. albicans* to extracellular matrix proteins (21), the inventors hypothesized that *C. albicans* interacted with heparin through linear heparin binding motifs (HBMs): conserved sequences of basic (Arg, Lys, His) and hydropathic amino acids in prescribed patterns.

BRIEF DESCRIPTION OF THE DRAWINGS

FIG. 1 schematically illustrates the internal lumen of an indwelling catheter.

FIGS. 2A-E demonstrate lack of an effect by heparin on wild type *Candida albicans* (*C. albicans*) planktonic growth and morphology.

FIGS. 3A-D demonstrate *C. albicans* binding to heparin and heparin analogs in vitro.

FIGS. 4A-C show that two lysine residues in linear heparin binding Motif 1 in *C. albicans* Int1 mediate binding to heparin, as measured by an ELISA assay in vitro. FIG. 4A discloses SEQ ID NOS 1, 40, 48, 2, 3, 52 and 53, respectively, in order of appearance. FIG. 4B discloses SEQ ID NO: 2. FIG. 4C discloses SEQ ID NOS 52-53, respectively, in order of appearance.

FIG. 5 compares pre-immune rabbit IgG with affinity-purified IgG raised against the sequence HKQEKQKKHQIHKV (SEQ ID NO:4) for ability to inhibit binding of *C. albicans* to heparin.

FIGS. 6A-C show consequences of heparin binding in vitro. FIG. 6A discloses SEQ ID NO: 65. FIG. 6B discloses SEQ ID NO: 66. FIG. 6C discloses SEQ ID NO: 67.

FIGS. 7A-B show consequences of heparin binding in vitro.

FIGS. 8A-F demonstrate that heparin binding motifs contribute to biofilm formation in vivo.

FIG. 9 demonstrates that affinity-purified IgG raised against the sequence HKQEKQKKHQIHKV (SEQ ID NO:4) substantially inhibited biofilm production in jugular venous catheters in rats. FIG. 9 discloses SEQ ID NO: 6.

FIG. 10 schematically illustrates the internal lumen of an indwelling catheter in the presence of antibody against heparin binding motifs on cell wall proteins of *C. albicans*.

FIG. 11 shows Anti-KKHQ specific binding to *Candida* species.

FIGS. 12A-C show Anti-KKHQ effect on biofilm progression.

Thirty-four *C. albicans* surface proteins encoding at least one linear heparin binding motif (HBM) were identified from a sequence-based search. Twelve of these 34 proteins flanked recently described transcriptionally active regions that are involved in biofilm production. Thirty-three of these 34 proteins are known targets of master biofilm regulators (22).

*C. albicans* binding to 2.5 units (12.5 µg) solid-phase heparin in an ELISA assay was significantly decreased by desulfation of heparin at the 2-0 or 2-N groups, and by preincubation of *C. albicans* with heparin. The protein Int1 contained the largest number of HBMs; Int1 is a surface protein that is involved in adhesion, filamentation, and antigenic recognition. In the Int1 sequence $_{804}$QKKHQIHK (SEQ ID NO: 1), alanine mutation of lysine residues at positions 805/806 significantly reduced binding of the Int1 mutant to heparin. Rabbit IgG recognizing the polypeptide $_{799}$HKQEKQKKHQIHKV$_{812}$ (SEQ ID NO: 4) inhibited *C. albicans* binding to heparin by 19%; pre-immune rabbit IgG had no effect.

Consequences of heparin binding in vitro included removal of *C. albicans* surface antigens such as Eno1, Pgk1, Tdh3, and Ssa1/2, which themselves contain putative HBMs; impairment of histatin-mediated killing; and modulation of gene expression. In vivo, substitution of alanine residues for lysines at positions 805/806 in $_{804}$QKKHQIHK (SEQ ID NO: 1) markedly attenuated biofilm formation in central venous catheters in rats. In addition, pre-incubation of *C. albicans* with rabbit IgG recognizing the polypeptide $_{799}$HKQEKQKKHQIHKV$_{812}$ (SEQ ID NO: 4) inhibited biofilm formation in vivo; pre-immune IgG had no inhibitory effect. These results identify linear HBM in *C. albicans* surface proteins, characterize specific lysine residues that mediate heparin binding, and demonstrate relevance for innate and adaptive immunity in vitro and biofilm formation in vivo.

The inventive method and composition ameliorated this undesirable situation by using antibodies against a specific heparin-binding motif that is expressed by surface proteins on *C. albicans*; other microorganisms also express similar heparin binding motifs. Without being held to a single theory, the disclosed antibodies reduce or prevent the undesirable biofilm from forming on the surface of a medical device, particularly a plastic device, implanted in a patient. Microorganisms include bacteria, yeast, fungi, etc. as known to one skilled in the art. Medical devices include those implanted or implantable in a patient, particularly plastic medical devices, including but not limited to catheters and central lines but excluding current non-plastic implanted joints, pacemakers, pacemaker wires, and spinal rods.

In one embodiment of the inventive method, antibodies were produced against a linear heparin binding motif that was expressed by a surface protein of *Candida albicans* (*C. albicans*). Related heparin binding motifs occur in surface proteins from *Staphylococcus epidermidis* (*S. epidermidis*) and *Staphylococcus aureus* (*S. aureus*).

Linear heparin binding motifs are sequential amino acids that conform to one of three consensus motifs (Cardin, Sobel, or Weintraub motifs); they have been identified in multiple mammalian proteins that bind heparin. While conformational heparin binding motifs also occur in some proteins, they must be identified by crystal structure of the protein. Antibodies to these linear heparin binding motifs inhibited *C. albicans* from adhering to heparin bound to a plastic surface (a microtiter plate).

Of the six million patients who have a central line implanted each year, more than 75,000 will develop bloodstream infections (23). Central line-associated blood stream infections (CLABSI) are a major source of hospital-acquired infection; over 43,000 CLABSI occurred among patients hospitalized in U.S. intensive care units (ICUs) in 2001, which is 3.2 infections for every 1000 line days. With a protocol for their sterile insertion and daily maintenance, CLABSI in ICUs dropped to 18,000 in 2009, but even with these improvements in ICUs procedures, more than 23,000 CLABSI occurred in patients on inpatient wards and 37,000 CLABSI occurred in outpatient hemodialysis patients in 2009. Even with a 50% reduction in CLABSI in ICU patients, the annual cost of these infections across the U.S. is more than $13 billion (23).

*Staphylococcus epidermidis* is the most common cause of CLABSI in central lines, with gram-negative rods second, *S. aureus* third, and *Candida* species fourth (24). In peripherally inserted central catheters (PICC), i.e., central lines inserted through peripheral veins in the arm, *Candida* species are the second most common cause of line infection (25). *Candida* spp. are equivalent to *S. aureus* in infections in central lines in the ambulatory setting (26). Among *Candida* spp, *C. albicans* is the most common cause of CLABSI (24).

When *Candida* species infect a central venous catheter, the organism enters the bloodstream to cause candidemia. Hosts at highest risk of candidemia, include burn patients and patients on a pump during coronary artery bypass procedures (27). Neutropenic oncology patients, premature newborns, and patients with major abdominal surgery such as intestinal resections are also high-risk patients with 8- to 16-fold the number of infections of other patient groups (27).

A major risk factor in candidemia is the presence of central lines (28-33), whose lumens are a site for formation of microbial biofilms that are effectively shielded from antimicrobial agents and host defenses. A second commonality is the use of heparin as an anticoagulant in most catheters. The amount of heparin is often considerable; e.g., a premature newborn in a neonatal intensive care unit may receive 150 units/kg/day, compared to 2.8 units/kg for a 70 kg adult receiving a 100 unit flush twice a day (20).

The ability to bind heparin is a unifying feature among *S. epidermidis*, *S. aureus*, and, *Candida albicans* (34-36), three of the leading causes of catheter-associated bloodstream infections. In experiments with *S. aureus*, high concentrations of heparin have been shown to increase *S. aureus* biofilm formation in vitro (37).

A first step in biofilm formation is microorganism adhesion or adherence to a surface of the implanted device, such as a catheter (38). In FIG. 1, negatively charged heparin molecules (circles) injected into the catheter lumen bind to the positively charged catheter surface, and heparin sulfate moieties (curved lines) are exposed on vascular endothelium lining catheter lumens. Linear heparin binding motifs present on the surface of microorganisms, such as *C. albicans*, interact either with heparin (A) or with heparin sulfate (B) and enable the organism to attach to the inside of the catheter. As the attached microorganisms replicate, they form the multilayered structure of a biofilm (C) and secrete the polysaccharide mortar-like matrix that holds the biofilm together. The inventors hypothesize that interactions between heparin and surface proteins on microorganisms such as *C. albicans* facilitate biofilm formation, and subsequent infection of the bloodstream when projections from biofilm break off into the catheter lumen and enter the bloodstream.

Heparin is associated with central line infections, particularly those due to *Candida* spp. In a randomized trial of 260 central lines, 128 were coated with chlorhexidine and 132 were coated with heparin; all *Candida* colonization and all candidemias occurred in patients whose central lines were coated with heparin (39). A second study in renal dialysis patients showed that those patients who received 5000 units of heparin in the middle of dialysis had considerably more catheter loss due to infection compared to patients not treated with heparin. Although staphylococcal infections were most common in this patient group, candidemia also occurred (40).

One mechanism by which heparin interacts with proteins is through linear heparin binding motifs, conserved sequences of basic amino acids such as lysine, arginine, and histidine interspersed with hydropathic amino acids (14). Microbial heparin-binding proteins are identified by short consensus motifs of basic (B) and hydropathic (X) amino acids, as defined by Cardin [XBBXBX], Weintraub [XBBBXXBX], or Sobel [XBBBXXBBBXBBX].

In the invention, a computer-based algorithm examined all 400 *C. albicans* surface and cell wall proteins for heparin binding motifs (HBM). Of the 6,000 known *Candida albicans* proteins, about 400 are localized to the cell wall of yeast or hyphae, depending upon the extraction technique (41). A sequence-based search identified putative Cardin, Sobel, or Weintraub motifs in 159 *C. albicans* proteins. Table 1 shows HBM in cell surface proteins expressed by *C. albicans*. The 34 proteins in Table 1 include only those that have the attribution "cell surface", "fungal cell wall", "yeast cell wall", or "hyphal cell wall" as the cellular component in the *Candida* Genome Database, where *=Weintraub motif; #=Cardin motif; ‡=Identified by molecular modeling studies; A="cell wall" in protein description (as of January 2011); obtained from *Candida* Genome Database (CGD); B="cell wall" in Gene Ontology (GO) annotation (as of January 2011); obtained from CGD; C=cell wall proteins as reviewed by Alberti-Segui (42) and D=cell wall proteins as reviewed by Chaffin (41).

The following procedure was used to identify a set of cell wall proteins in *C. albicans* with HBM. The first step combined evidence to identify possible cell wall proteins in *C. albicans*. Specifically, using "cell wall" as keywords, 154 putative cell wall proteins were identified from protein descriptions, and another 245 unique cell wall proteins were identified from Gene Ontology functional annotations from *Candida* Genome Database (www.candidagenome.org; Assembly 21). Also included were 125 non-redundant cell wall proteins identified by Alberti-Segui (50) and another 174 reported by Chaffin (22) and mapped annotations to Assembly 21. The second step screened for consensus HBM in protein ORF sequences of these cell wall proteins from Assembly 21. Three types of consensus motifs were included: Weintraub (XBBBXXBX), Sobel (XBBBXX-BBBXXBBX), and Cardin (XBBXBX) motifs, where B is a basic amino acid and X is a hydropathic amino acid. In the algorithm, basic amino acids are H, K, and R. Hydropathic amino acids are W, F, Y, L, I, C, M, G, V, S, T, A, N, P, and Q. A total of 159 cell wall proteins were identified that have possible HBM, and some have multiple motifs. The 159 proteins that met the search criteria were then manually curated to select only those proteins whose cell wall localization was confirmed by manual or computational methods in the *Candida* Genome Database.

Proteins with GPI anchoring sequences within these 159 cell wall proteins with HBM were further identified. Three Web servers were used to perform GPI anchoring sequence prediction: SignalP (43), GPI-SOM (44), and PredGPI (45). Combined results of these three prediction methods indicated that 15 out of these 159 proteins had GPI anchoring sequences, four of which overlapped with reviewed GPI anchoring proteins (46).

The algorithm identified 34 cell wall proteins with potential linear heparin binding sequences that matched the Cardin, Weintraub, and Sobel motifs. The 34 identified cell wall proteins were Ahp1, Als7, Atc1, Bud2, Cat1, Cef3, Chs1, Crh12, Dot4, Not5, Pdi1, Pga4, Pgk1, Phr3, Rbt1, Rps6A, Sam2, Srb1, Ssa2, Ssb1, Tdh3, Eft2, Eno1, Gap1, Gph1, Gpm2, Hem13, Hsp104, Hsp70 (also called Ssa1), Ino1, Int1, Ipp1, Ugp1, Xyl2. Three of these proteins, Als7, Pga4, and Rbt1, have GPI anchors. The genes encoding eleven of these proteins, Als7, Cat1, Dot4, Eno1, Gph1, Ino1, Rbt1, Sam2, Srb1, Ssa2, and Ugp1, are located in newly defined transcriptionally active regions that are critically involved in biofilm formation (22). Moreover, many of these proteins are known to be regulated by at least one of six master biofilm regulators; by RNA-seq, where RNA-seq is defined as the use of high-throughput sequencing techniques to sequence cDNA in order to get sequence information about the transcriptome, the sample's RNA content; CAT1, GAP1, GPH1, and HSP104 are up-regulated in biofilm formation, while CHS1, ENO1, GPM2, HEM13, INO1, IPP1, PGK1, RPS6A, SAM2, SRB1, SSA2, SSB1, and TDH3 are down-regulated (22).

Given the presence of putative HBM among *C. albicans* surface proteins and the possible interactions with heparin in central venous catheters or with heparin sulfate proteoglycans expressed on host tissues such as vascular endothelium, the biochemical determinants and immunologic consequences of this interaction were defined. The protein Int1 (SEQ ID NO: 5) (accession number P53705.2; GI 187608862) had the highest number of HBM (five). Int1 (SEQ ID NO: 5) spans 1711 amino acids and is localized to the cell wall of the bud neck in *C. albicans*. It mediates adhesion, hyphal formation, and virulence, defined as the ability to cause disease such as bloodstream infection (47). Using the same search technique, HBM were also detected in surface proteins of *S. epidermidis* and *S. aureus*.

TABLE 1

| Gene ID (Assembly 21) | Protein | Ref. | # of motifs | Motif 1 | Motif 2 | Motif 3 | Motif 4 | Motif 5 |
|---|---|---|---|---|---|---|---|---|
| orf19.4257 | Int1 | C | 5 | $_{804}$QKKHQIHK$^‡$ (SEQ ID NO: 1) | $_{1383}$THKGRF$^\#$ (SEQ ID NO: 40) | $_{1530}$MKRGKP$^\#$ (SEQ ID NO: 48) | $_{1593}$FKKRFFKL* (SEQ ID NO: 2) | $_{1612}$SHKTRA$^\#$ (SEQ ID NO: 3) |
| orf19.1738 | Ugp1 | B, D | 3 | $_{176}$SHRIRV$^\#$ (SEQ ID NO: 7) | $_{310}$IKKFKY$^\#$ (SEQ ID NO: 41) | $_{368}$IRHFKG$^\#$ (SEQ ID NO: 49) | | |

TABLE 1-continued

| Gene ID (Assembly 21) | Protein | Ref. | # of motifs | Motif 1 | Motif 2 | Motif 3 | Motif 4 | Motif 5 |
|---|---|---|---|---|---|---|---|---|
| orf19.3370 | Dot4 | B | 3 | $_{442}$NKKGKS# (SEQ ID NO: 8) | $_{519}$CHKCHN# (SEQ ID NO: 42) | $_{635}$FKRFKF# (SEQ ID NO: 50) | | |
| orf19.3651 | Pgk1 | A, B, D | 3 | $_{136}$GKKVKA# (SEQ ID NO: 9) | $_{146}$VKKFRQ# (SEQ ID NO: 43) | $_{168}$AHRAHS# (SEQ ID NO: 51) | | |
| orf19.4660 | Rps6A | B, D | 2 | $_{185}$QRKRALKA* (SEQ ID NO: 10) | $_{192}$AKKVKN# (SEQ ID NO: 44) | | | |
| orf19.5107 | Not5 | B | 2 | $_{114}$QKRSRF# (SEQ ID NO: 11) | $_{333}$VKKLKP# (SEQ ID NO: 45) | | | |
| orf19.5130 | Pdi1 | D | 2 | $_{210}$NKKFKN# (SEQ ID NO: 12) | $_{301}$GKKYRG# (SEQ ID NO: 46) | | | |
| orf19.6387 | Hsp104 | D | 2 | $_{53}$VKRARY# (SEQ ID NO: 13) | $_{199}$ARRSKS# (SEQ ID NO: 47) | | | |
| orf19.1065 | Ssa2 | B, D | 1 | $_{258}$LRRLRT# (SEQ ID NO: 14) | | | | |
| orf19.1067 | Gpm2 | B | 1 | $_{45}$IKKNHL# (SEQ ID NO: 15) | | | | |
| orf19.1327 | Rbt1 | A, B, C | 1 | $_{121}$GKKVKQ# (SEQ ID NO: 16) | | | | |
| orf19.2762 | Ahp1 | B, D | 1 | $_{171}$LKRIHN# (SEQ ID NO: 17) | | | | |
| orf19.2803 | Hem13 | B, D | 1 | $_{257}$IRRGRY# (SEQ ID NO: 18) | | | | |
| orf19.3590 | Ipp1 | B, D | 1 | $_{74}$TKKGKL# (SEQ ID NO: 19) | | | | |
| orf19.377 | Phr3 | B, C | 1 | $_{115}$PHHHLNRY* (SEQ ID NO: 20) | | | | |
| orf19.395 | Eno1 | B, D | 1 | $_{141}$AKKGKF# (SEQ ID NO: 21) | | | | |
| orf19.3966 | Crh12 | A, B, C | 1 | $_{420}$TKHIHN# (SEQ ID NO: 22) | | | | |
| orf19.4035 | Pga4 | B, C, D | 1 | $_{259}$AKRPRP# (SEQ ID NO: 23) | | | | |
| orf19.4152 | Cef3 | B | 1 | $_{623}$LRKYKG# (SEQ ID NO: 24) | | | | |
| orf19.4304 | Gap1 | B | 1 | $_{72}$QRKLKT# (SEQ ID NO: 25) | | | | |
| orf19.4980 | Ssa1 | B, D | 1 | $_{259}$LRRLRT# (SEQ ID NO: 26) | | | | |
| orf19.5188 | Chs1 | B, C | 1 | $_{126}$PKRQKT# (SEQ ID NO: 27) | | | | |
| orf19.5788 | Eft2 | B, D | 1 | $_{581}$NKHNRI# (SEQ ID NO: 28) | | | | |
| orf19.6190 | Srb1 | B, D | 1 | $_{123}$FHKAHG# (SEQ ID NO: 29) | | | | |
| orf19.6214 | Atc1 | A, B | 1 | $_{959}$PKRVKV# (SEQ ID NO: 30) | | | | |
| orf19.6229 | Cat1 | B | 1 | $_{82}$GKKTRI# (SEQ ID NO: 31) | | | | |
| orf19.6367 | Ssb1 | B, D | 1 | $_{263}$LRRLRT# (SEQ ID NO: 32) | | | | |

TABLE 1-continued

| Gene ID (Assembly 21) | Protein | Ref. | # of motifs | Motif 1 | Motif 2 | Motif 3 | Motif 4 | Motif 5 |
|---|---|---|---|---|---|---|---|---|
| orf19.657 | Sam2 | B, D | 1 | $_{380}$PKKLKF# (SEQ ID NO: 33) | | | | |
| orf19.6814 | Tdh3 | B, D | 1 | $_{70}$GHKIKV# (SEQ ID NO: 34) | | | | |
| orf19.7021 | Gph1 | B, D | 1 | $_{656}$TKHHIPKA* (SEQ ID NO: 35) | | | | |
| orf19.7400 | Als7 | B, C | 1 | $_{1482}$SKRNKN# (SEQ ID NO: 36) | | | | |
| orf19.7585 | Ino1 | B, D | 1 | $_{151}$MKRAKV# (SEQ ID NO: 37) | | | | |
| orf19.7676 | Xyl2 | A, B, D | 1 | $_{330}$THRFKF# (SEQ ID NO: 38) | | | | |
| orf19.940 | Bud2 | B | 1 | $_{716}$LRKGKS# (SEQ ID NO: 39) | | | | |

Heparin effect on *Candida albicans* growth and morphology was determined. A single colony of BWP17wt was inoculated into 3 ml YPD medium and incubated overnight at 30° C. with shaking at 225 rpm. Overnight cultures were diluted to an $OD_{600}$ of 0.1 in 5 ml of YPD (yeast) or RPMI-HEPES (hyphae) in a 50 ml conical polypropylene tube and incubated in the presence or absence of 100 units/ml preservative-free pharmaceutical heparin at 30° C. for six hours. Cells (1 ml) were fixed with an equal volume of 4% formaldehyde in FACS buffer at 4° C. for one hour, then pelleted (7,000 rpm for 3 minutes) and washed with PBS. After reconstitution in 0.5 ml PBS, filipin (50 mg/ml stock solution in DMSO) was added to a final concentration of 100 μg/ml and incubated with cells at room temperature for five minutes. Cells were pelleted, washed with PBS and mounted on a slide using Fluoromount G. For calcofluor white staining, after six hours incubation, 1 μl of 1 mg/ml stock solution of calcofluor white in 0.1 N NaOH was added to 100 μl cells to a final calcofluor white concentration of 10 μg/ml.

Microscopy was performed by imaging filipin, PKH26, DAPI, and heparin-Alexa Fluor 488 on a Nikon Ti-E inverted microscope with a 100×CFI APO oil NA 1.49 objective. Filipin was excited with a Prior Lumen 200 metal halide light source set at 10% light output. This light was further attenuated by ND4 and ND8 neutral density filters in series to reduce light output to approximately 3% of output from the liquid light guide. The filters used for imaging were EX 360/40, dichroic 400 nm lp, EM 460/50. Images were acquired with an Andor iXon emccd camera. Exposure times were 391 ms. Excitation of PKH26/DAPI/Heparin-Alexa Fluor 488 triple staining was accomplished with a Nikon A1R si laser scanning confocal. DAPI was imaged with 405 nm excitation and a 450/50 filter with a laser power of 16.3 and a photomultiplier tube (pmt) voltage of 92. Alexa Fluor 488 was imaged with 488 nm excitation from an Argon-ion laser and a 525/50 filter with a laser power of 6.0 and a pmt voltage of 84. PKH26 was imaged with 561 nm excitation and a 595/50 filter with a laser power of 13.2 and a pmt voltage of 108. Gains were kept below 110 to eliminate contribution from *C. albicans* autofluorescence; lack of autofluorescence was confirmed by comparison to a control sample without heparin-Alexa Fluor 488. Images were processed with Nikon NIS-Elements AR 4.11.00 64-bit software. Calcofluor white slides were examined using a Zeiss Axiovert 200M fluorescent microscope equipped with a Plan-Apochromat 63×/1.40 oil objective lens with 1.6× optivar and DAPI filter at 350 nm excitation and 460 nm emission. Images were captured using a Zeiss Axiocam color camera and processed with Axiovision version 4.8.2.

Flow cytometry was performed by inoculating a single colony of BWP17wt into 3 ml YPD medium and incubating overnight at 30° C. with shaking at 225 rpm. Overnight cultures were diluted to $OD_{600}$ of 0.1 in 5 ml of YPD or RPMI-HEPES and incubated in the presence or absence of 100 units/ml preservative-free pharmaceutical heparin at 30° C. for one hour. One ml aliquots of each mixture were removed, pelleted (7,000 rpm for 3 min), washed twice with PBS, and reconstituted in 1 ml PBS. Flow cytometry analysis was performed using the Imagestream$^X$ flow cytometer (Amnis, Seattle Wash.) equipped with a 405 nm, 488 nm, 653 nm, laser and multi-mag function. The 40× magnification, 10 mm/sec flow rate, and 488 nm laser were used to collect SSC and Brightfield parameters. The flow cell allows particles up to 100 μm wide (height unlimited) to be collected in the instrument. INSPIRE (v.6.0) software was used to acquire events. Software analysis using IDEAS (v5.0) identified percent hyphae using aspect ratio, height and width features using the side scatter (Channel 6) and brightfield (Channel 1) parameters. Objects were selected within each file and tagged to use as identification of truth sets within the population.

For growth curves in the presence or absence of soluble heparin, a single colony of BWP17wt was inoculated into 3 ml YPD medium and incubated overnight at 30° C. with shaking at 225 rpm. Overnight cultures were diluted to an $OD_{600}$ of 0.1 in 5 ml of YPD, RPMI-MOPS, RPMI-HEPES or CSM in a 50 ml conical polypropylene tube. Preservative-free pharmaceutical heparin (1000 units/ml) was added to yield a final concentration of 100 units/ml in the heparin-treated samples. Cultures were grown at 30° C. with shaking and $OD_{600}$ measured periodically. Doubling times ($t_d$) were calculated based on the equation $t_d = \ln 2/\mu$ (μ=specific growth rate (48). One hundred units/ml heparin, the concentration recommended to prevent clotting of central venous catheters (20), had no effect on doubling times of planktonic yeast cells grown in YPD, RPMI-HEPES, RPMI-MOPS or CSM, as shown in FIGS. 2A and 2B.

FIGS. 2A-E demonstrate lack of an effect by heparin on wild type Candida albicans (C. albicans) planktonic growth and morphology.

Figure 1:
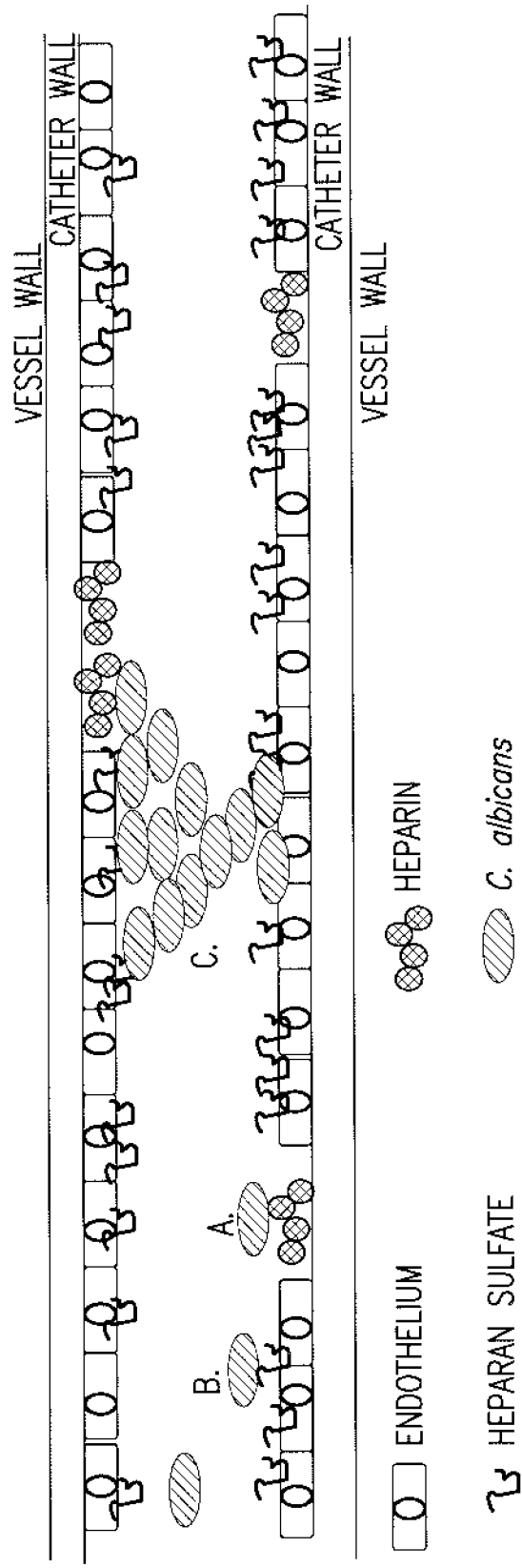
Figure 2A:
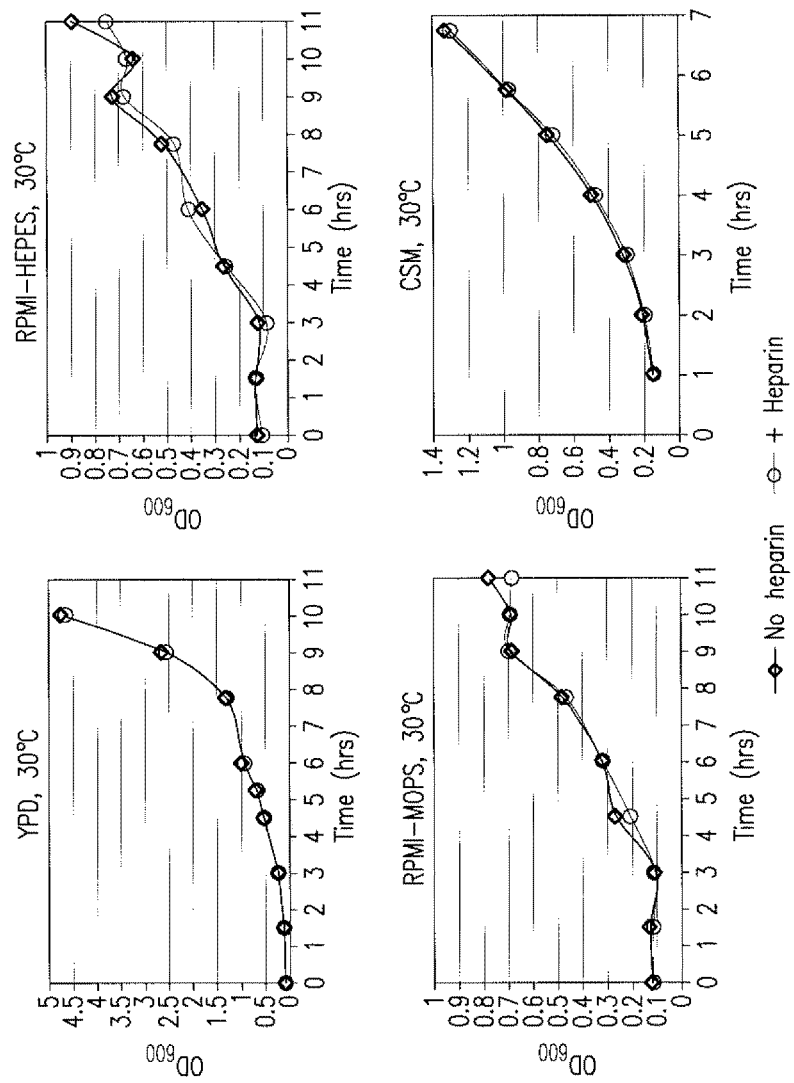
FIG. 2A shows that growth curves in the presence (open circles) or absence (closed diamonds) of soluble heparin were identical.
Figures 2B, 2C, 2D:
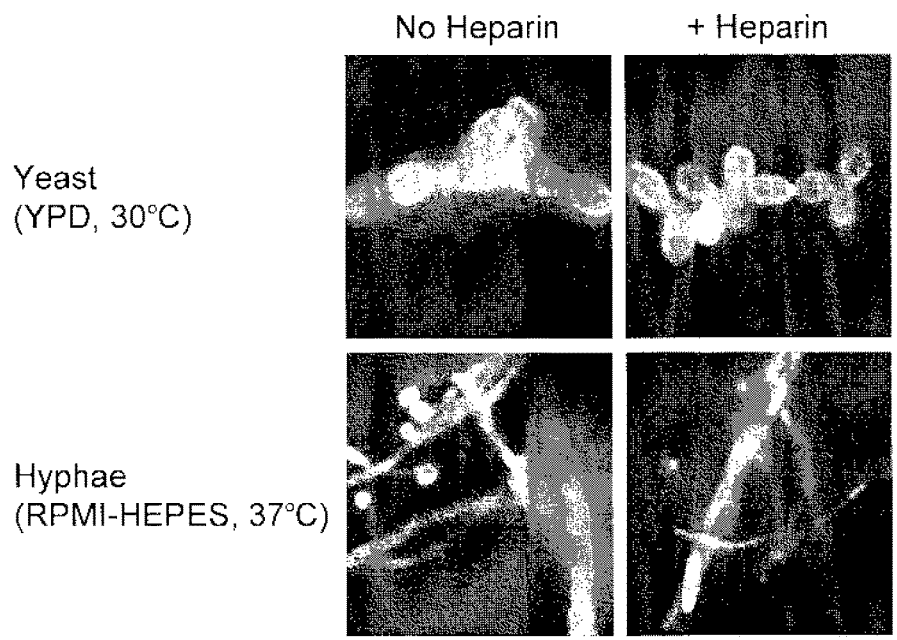
FIG. 2B shows that doubling times in various media at 30° C. in the absence and presence of heparin (100 units/ml) were identical.
FIG. 2C shows that percent hyphae as determined by flow cytometry did not differ after incubation with or without heparin (100 units/ml) under conditions that favor yeast (YPD, 30° C.) or hyphae (RPMI-HEPES, 37° C.).
Figure 2E:
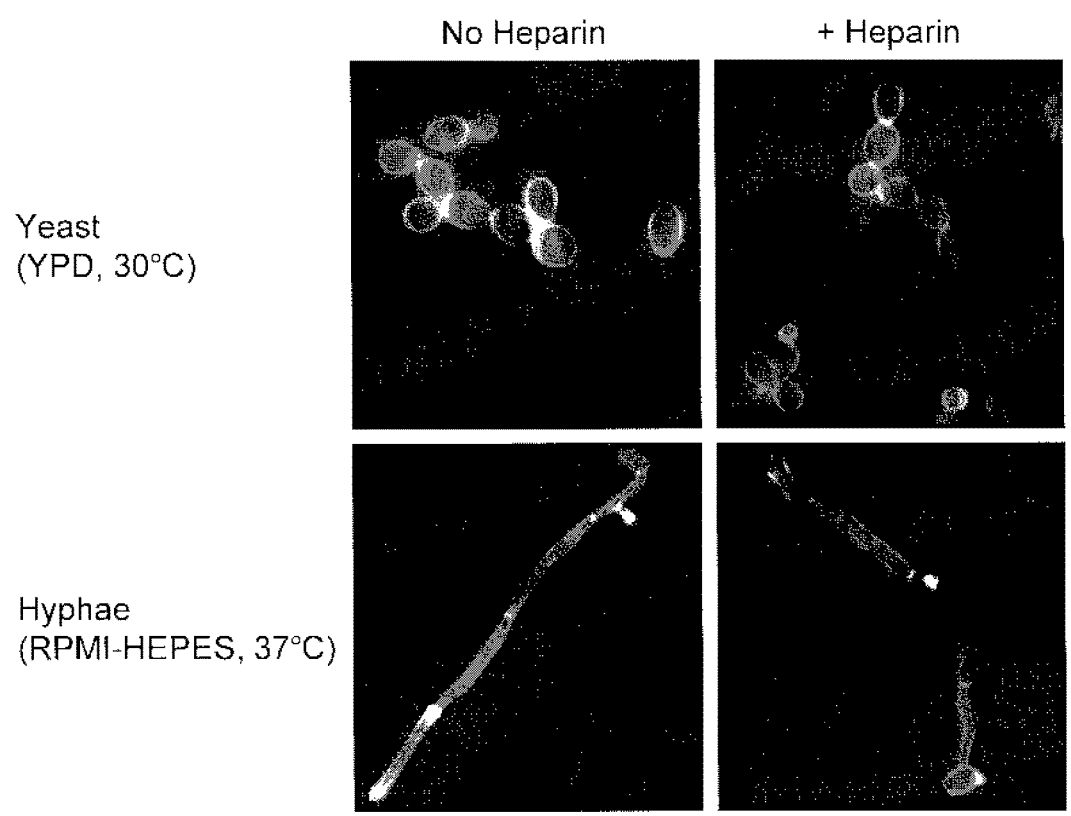

FIGS. 2D-E show that the integrity of membrane sterols identified with filipin (FIG. 2D) and the location of septin rings identified with calcofluor white staining (FIG. 2E) were identical between untreated and heparin-treated organisms. Thus, concentrations of heparin commonly used to maintain patency of central venous catheters (100 units/ml) did not lead to readily observable differences in growth or cellular architecture of the organism.

Binding of heparin by C. albicans was examined in vitro. Heparin was labeled with Alexa Fluor 488 by a method modified from Osmond (49). Briefly, 5 mg heparin (Sigma) was dissolved in 0.5 ml MES buffer (0.1M 2-(N-morpholino)ethanesulfonic acid hydrate, pH 4.5, Sigma), then mixed with a solution of 1 mg Alexa Fluor 488 hydrazide (Life Technologies) in 0.4 ml MES buffer. After adding 0.2 ml of EDC solution (15 mg 1-ethyl-3-(3-dimethylaminopropyl) carbo-diimide/ml water, Thermo Scientific), the mixture was stirred at room temperature for 30 min. A second 0.2 ml aliquot of EDC solution was added and the mixture stirred at room temperature for an additional 30 min. After adding 1.3 ml NaOAc (1 M, pH 4.8) and stirring at room temperature for one hour, heparin-Alexa Fluor 488 was purified on a PD-10 desalting column (GE Healthcare) equilibrated in autoclaved nanopure water. Fractions containing the labeled material detected at 490 nm were combined and dried overnight on a SpeedVac concentrator (Savant) with heating. The resulting solid was dissolved in autoclaved nanopure water to 10 mg/ml and stored at 4° C.

Heparin-Alexa Fluor 488 bound to PKH26- and DAPI-labeled C. albicans. A single colony of BWP17wt was inoculated into 3 ml YPD medium and incubated overnight at 30° C. with shaking at 225 rpm. Using a PKH26 Red Fluorescent Cell staining kit (including PKH26 dye and diluent C, Sigma), $2 \times 10^7$ cells were mixed with 1 ml diluent C. To this solution was added a mixture of 4 µl PKH26 dye in 1 ml diluent C, and the mixture allowed to stand at room temperature for 3 min. After adding 10 ml 3% BSA, the mixture was centrifuged at 3,000 rpm for 7 min. The resultant magenta-colored cells were washed with 10 ml each of 1% BSA and PBS, with centrifugation after each step. After supernatant removal, the cells were reconstituted in 10 ml fresh PBS. Two 1 ml ($2 \times 10^6$ cells) aliquots were placed in separate 15 ml conical tubes, centrifuged, and supernatants removed. Each was reconstituted with 2 ml YPD, and heparin-Alexa Fluor 488 (0.1 ml of above 10 mg/ml solution) was added to the experimental sample. Control and experimental samples were incubated at 30° C. with shaking (225 rpm) for 30 min, at which time 0.4 ml aliquots of each were removed, pelleted (10,000 rpm for 3 min), and washed twice with PBS. After reconstitution with 0.5 ml PBS, DAPI (4',6-diamidino-2-phenylindole dihydrochloride (Sigma, stock solution of 5 mg/ml) was added to a final concentration of 1 µg/ml and the solution allowed to stand at room temperature for 10 min. Cells were pelleted and washed twice with PBS, then mounted on a microscope slide using Fluoromount G.

To measure the binding of C. albicans to solid-phase heparin, a heparin-binding ELISA assay was developed, as follows. A single colony of each C. albicans wild type or mutant strain from a YPD plate was inoculated into 3 ml YPD medium and incubated overnight at 30° C. with shaking at 225 rpm. Sigma heparin (fresh solution made daily), diluted to 25 units/ml in autoclaved, sterile-filtered PBS was added as 0.1 ml aliquots to each well of an allyl amine-coated 96-well heparin binding microtiter plate (BD Biosciences). The plate was incubated at room temperature overnight in the dark (50). In the morning, the plate was washed with acetate buffer (100 mM NaCl, 50 µM NaOAc, 0.2% Tween 20, pH 7.2), incubated with 3% bovine serum albumin (BSA) in PBS at 30° C. for 1 hour, then washed with PBS. In the meantime, overnight cultures of C. albicans were subcultured by dilution to $OD_{600}$ of 0.2 in 25 ml of YPD, and grown at 30° C. to mid-log phase ($OD_{600}$ 0.6-0.7). Cells were pelleted (3,000 rpm for 7 minutes), washed twice with PBS and reconstituted in RPMI-HEPES to $4 \times 10^5$, $2 \times 10^5$, and $1 \times 10^5$ CFU/ml, respectively. One hundred µl of each C. albicans dilution was applied to the microtiter wells; experiments for each strain were performed in quadruplicate. The plate was incubated at 30° C. for one hour and washed with PBS to remove non-adherent C. albicans. One-tenth ml of a biotinylated polyclonal rabbit anti-C. albicans antibody raised against soluble proteins in a C. albicans lysate (Meridian Life Science), which had been diluted 1:2500 in FACS-Tween (0.05% Tween 20 in FACS buffer consisting of 0.3% BSA), was added to each well. The plate was incubated at 30° C. for one hour, then washed with PBS-Tween (0.05% Tween 20 in PBS). One-tenth ml streptavidin alkaline phosphatase (Biolegend) diluted 1:10,000 in FACS-Tween was then added to each well, and the plate was incubated at 30° C. for 30 minutes. After washing with PBS-Tween and AKP buffer (100 mM Tris base, 50 µM $MgCl_2$, 100 mM NaCl, pH 9.5), 0.1 ml alkaline phosphatase substrate (KPL) was added to each well. After 45 minutes, absorbance at 595 nM was read on a Beckman Coulter DTX 880. When desulfated heparin analogs, chondroitin sulfate, or dermatan sulfate were used, equimolar amounts of the analogs (with respect to heparin) were applied to the allyl amine-coated 96-well plate instead of heparin.

The ability of soluble heparin to inhibit C. albicans binding to plate-bound heparin was demonstrated by pre-incubating $1 \times 10^6$ CFSE-labeled C. albicans with 200 units heparin at 37° C. for one hour in wells of a 96-well black plate. C. albicans was labeled with carboxyfluorescein succinimidyl ester (CFSE), succinimidyl ester (CFSE; Invitrogen), which is used to track cell division and therefore does not kill the organism (28), as follows. A single colony of C. albicans was suspended in CSM to an $OD_{600}$ of 0.1, diluted 1:200 into 25 ml CSM and grown at 30° C. overnight to mid-log phase ($OD_{600}$ 0.6-0.7). Cells were washed twice in sterile PBS and suspended in PBS at $2 \times 10^7$ CFU/ml. Carboxyfluorescein succinimidyl ester (Life Technologies) was dissolved in DMSO, diluted in PBS to 50 µM, and 0.5 ml CFSE mixed with 0.5 ml C. albicans suspension. The mixture was incubated for 20 min at room temperature on a rotator, washed once with FACS buffer, once with PBS, then suspended in 1 ml FACS buffer. Intensity of labeling was determined as the mean fluorescence intensity using a BD Accuri C6 cytometer (San Jose, Calif.) with excitation at 488 nm and a 533/30 emission filter. Wells of a black 96-well microtiter plate were incubated with 0.1 mg poly-D-lysine for one hour at room temperature, washed three times with PBS, then incubated with 200 units of heparin in 100 µl RPMI-HEPES overnight at room temperature. The following afternoon, C. albicans wild type strain and mutants were labeled with CFSE as follows: after growth of C. albicans to mid-log phase in CSM medium, organisms were washed two times in PBS and suspended in PBS at a concentration of $2 \times 10^7$/ml. 0.5 ml cells was mixed with 0.5 ml CFSE, covered in foil, and rotated on a mixer for 20 minutes at room temperature. CFSE-labeled C. albicans cells were pelleted in a minifuge at 3000 rpm for four minutes, washed once with FACS buffer (0.3% bovine serum albumin in PBS), washed again with PBS, and then suspended in 1 ml FACS buffer at a concentration of $1 \times 10^7$/ml. 100 µl CFSE-labeled C. albicans ($1 \times 10^6$) were deposited in test wells for 60 minutes at room temperature. At the end of the incubation period, wells were washed three times with PBS, and fluorescence in each well was measured (Beckman Coulter Multimode detector DTX880).

Figures 3A, 3B:
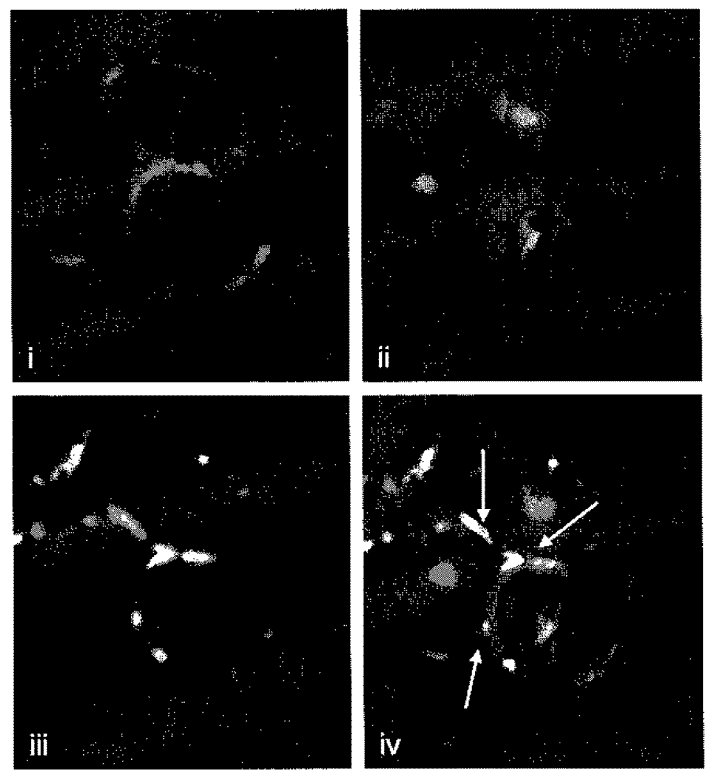

FIGS. 3A-D demonstrate C. albicans binding to heparin in vitro. FIG. 3A shows confocal microscopy of C. albicans in the presence of heparin-Alexa Fluor 488, with (i) C. albicans cell wall stained with PKH26, (ii) nucleus stained with DAPI, (iii) cell wall outlined by heparin-Alexa Fluor 488, and (iv) arrows indicating co-localization of heparin with C. albicans cell surface. Incubation of C. albicans with 100 units/ml heparin-Alexa Fluor 488 for 30 mins at 30° C. demonstrated co-localization of heparin with the C. albicans cellular surface (FIG. 3A). Heparin deposition was seen at the interface of adjoining yeast cells and in individual cells.

FIG. 3B shows binding of 10,000 colony-forming units (CFU) C. albicans ($OD_{595}$) to increasing concentrations of heparin immobilized on an allyl amine-coated 96-well microtiter plate; values are ±SD of duplicate wells. Binding of C. albicans at 10,000 CFU/well did not change over heparin concentrations ranging from 1.25 units/well (6.3 µg/well) to 20 units/well (100 µg/well) (FIG. 3B), indicating saturation of the allyl amine plate by heparin in low concentrations.

Figure 3C:
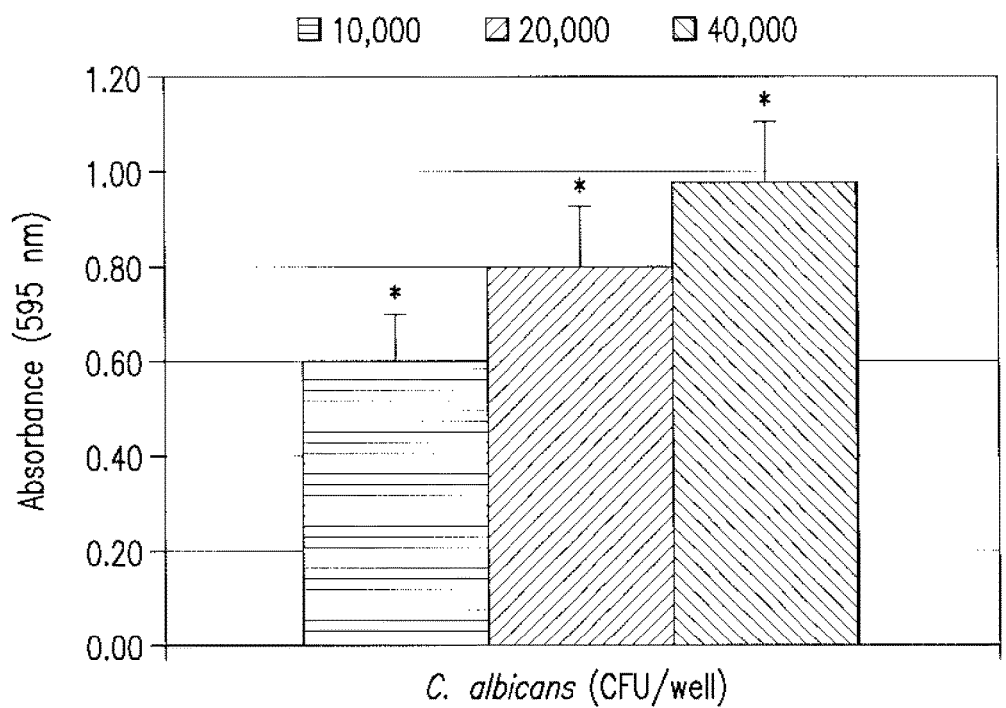

FIG. 3C shows the linear dose-response for the heparin binding ELISA assay with 2.5 units/well heparin and increasing C. albicans input from 10,000 (left-most bar), 20,000 (center bar), and 40,000 (right-most bar) CFUs; the graph represents mean±SD of four experiments, *p<0.007 for all inputs. FIG. 3C shows that the $OD_{595}$ of the ELISA assay increases linearly as input of C. albicans increased from 10,000 colony forming units (CFU)/well to 40,000 CFU/well.

Figure 3D:
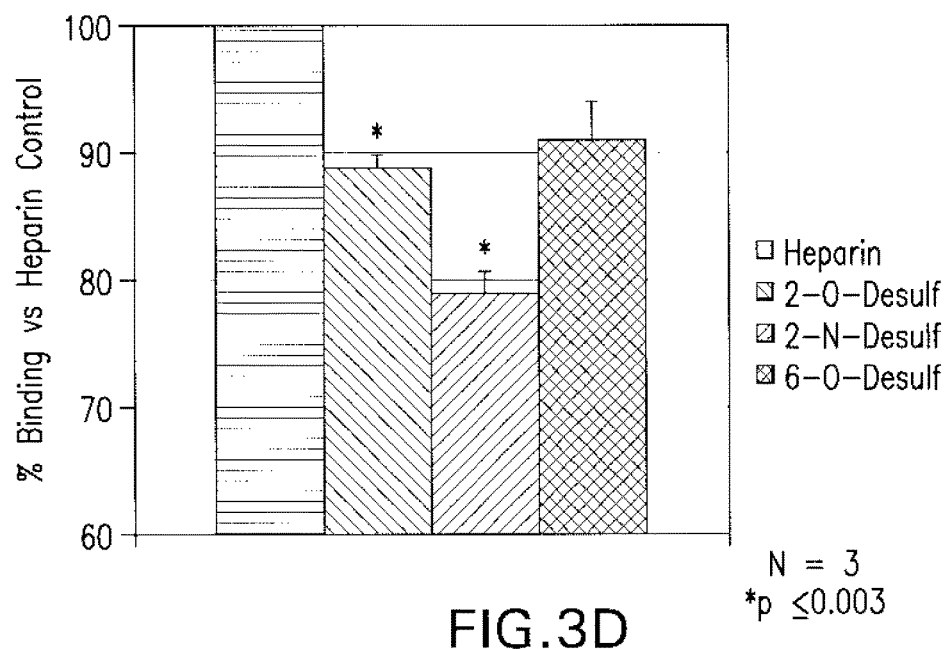

FIG. 3D shows binding of C. albicans (40,000 CFU/well) to equimolar amounts of heparin analogs desulfated at the 2-O (second from the left bar), 2-N (second from the right bar), or 6-O (right-most bar) positions versus heparin control (left-most bar) (normalized to 100%), with the graph representing mean±SD of three experiments, performed in triplicate *p<0.003, ** p=0.20 vs. heparin control. With equimolar amounts of desulfated heparins, binding of C. albicans was decreased by 11% when heparin was desulfated at the 2-0 position of iduronic acid (p=0.003), and by 21% when heparin was desulfated at the 2-N position of glucosamine (p=0.002) (FIG. 3D). Removal of the sulfate group at the 6-O position of glucosamine did not significantly reduce binding.

Pre-incubation of CFSE-labeled C. albicans with 100 units/ml heparin decreased binding to heparin by 27% (p=0.022; data not shown). C. albicans also recognizes the related structures of chondroitin sulfate and dermatan sulfate. Binding of C. albicans to heparin and to chondroitin sulfate was equivalent, but binding to dermatan sulfate was reduced (p=0.019; data not shown). These results confirmed that the binding of C. albicans to heparin and similar glycosaminoglycans (chondroitin sulfate and dermatan sulfate) could be reproducibly measured and, in the case of heparin, specifically inhibited by pre-incubating the organisms with heparin. These results also suggested that surface components of C. albicans may mediate C. albican binding to heparin.

Location of HBM in Int1 (SEQ ID NO: 5) were determined. Five overlapping polypeptides spanning amino acids 51-1711 of Int1 were expressed with a 6× His tag (SEQ ID NO: 54) in S. cerevisiae BJ3501 and purified by affinity chromatography (HisTrap column; GELifesciences). Fractions containing the His-tagged polypeptide were pooled, diluted with loading buffer (10 mM phosphate, pH 7.0 plus 250 mM NaCl) and applied to a heparin sepharose column (HiTrap Heparin HP; GE Lifesciences). Heparin-binding polypeptides were eluted with a step gradient of NaCl (0.5-2 M) in loading buffer. Eluted fractions were analyzed by SDS-PAGE and immunoblot using anti-His tagged antibody (Santa Cruz) and chemiluminescent detection (SuperSignal West Pico Mouse IgG Detection Kit, Pierce) according to manufacturers' instructions. Polypeptides spanning aa 656-1193 and aa 1548-1711 bound to heparin-Sepharose and were eluted with NaCl, indicating that the HBM in those domains, schematized as Motif 1 (SEQ ID NO: 1), Motif 4 (SEQ ID NO: 2), and Motif 5 (SEQ ID NO: 3) (FIG. 4A), were candidates for mediating binding to heparin. Bolded letters represent basic amino acids in heparin binding motifs; unbolded letters represent hydropathic residues. Polypeptides spanning aa 51-385, aa 385-659, and 1188-1551 failed to bind to a heparin-Sepharose column.

Figures 4A, 4B:
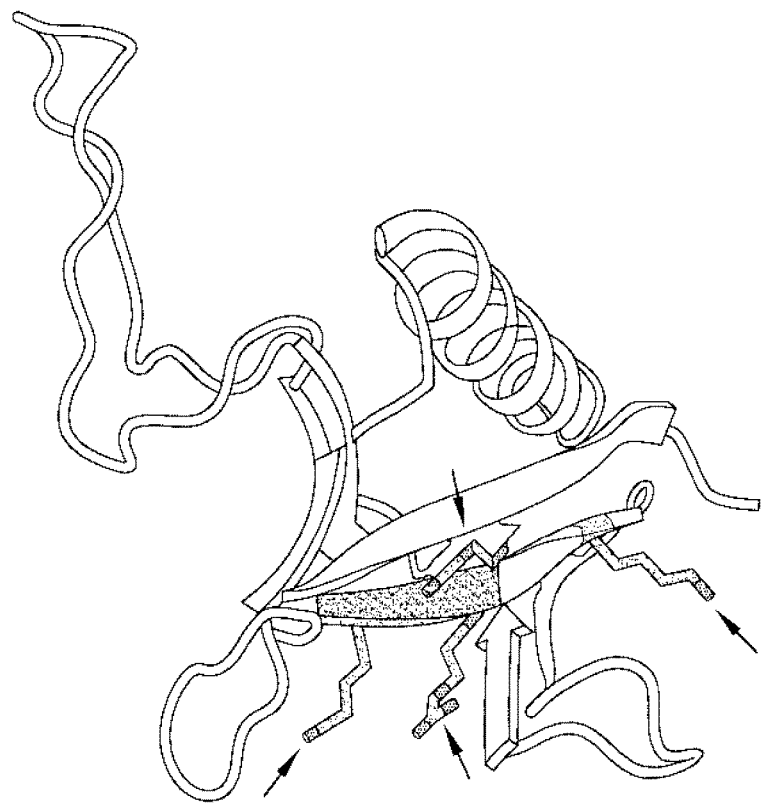

The linear polypeptide spanning aa 656-1193 contains one potential heparin binding site, 504QKKHQIHK (SEQ ID NO: 1) (basic residues shown in red) (Motif 1 in Table 1 and FIG. 4A). The linear polypeptide spanning aa 1548-1711 contains a canonical Weintraub motif $_{1593}$FKKRFFKL (SEQ ID NO: 2) (Motif 4 in Table 1 and FIG. 4A) and a canonical Cardin motif $_{1612}$SHKTRA (SEQ ID NO: 3) (Motif 5 in Table 1 and FIG. 4A). Sequence homology search using BLAST indicated that aa 1548-1711 contains a Pleckstrin homology domain (PHD), which is structurally resolved. Using homology-based 3-D modeling, we found that the three lysine residues and single arginine residue in Motif 4 were located on the rim of the PHD and might facilitate binding to a strong anion such as heparin by electrostatic interaction (FIG. 4B, arrows). The Cardin motif (Motif 5) did not share this conformation.

To test whether $_{804}$QKKHQIHK (SEQ ID NO: 1) (Motif 1) and/or $_{1593}$FKKRFFKL (SEQ ID NO: 2) (Motif 4) mediated the binding of heparin to C. albicans, standard PCR-mediated mutagenesis (51) was used to construct a set of isogenic INT1 disruptants and mutants (Table 2).

TABLE 2

| Strain | Abbreviation | Genotype | Source |
|---|---|---|---|
| BWP17 | — | ura3::imm434/ura3::imm434 his1::hisG/his1::hisG arg4::hisG/arg4::hisG | [27] |
| BWP17WT | WT | BWP17 plus arg4::ARG4::URA3/his1::hisG::HIS1 | [27] |
| VBIDM2 | — | as BWP17 plus int1::ARG4/int1::URA3 | [60] |
| VBIDM6-2 | DD | as VBIDM2 plus his1::hisG/HIS1 | [60] |
| KO503 | Motif 4 | VBIDM2 plus his1::hisG::HIS1-INT1 (KK1595AA) | current |
| KO507 | Motif 1 | VBIDM2 plus his1::hisG::HIS1-INT1(KK804AA) | current |
| KO508 | Motifs 1&4 | VBIDM2 plus his1::hisG::HIS1-INT1(KK804AA, KK1595AA) | current |
| KO509 | Reint | VBIDM2 plus his1::hisG::HIS1-INT1 (WT) | current |

Construction of mutants was as follows. *C. albicans* genomic DNA was isolated from saturated overnight cultures using glass beads as described (52). A lithium acetate method was used to transform *C. albicans* (41). Plasmids and PCR products were purified using kits (Fermentas/ThermoFisher, Pittsburgh Pa.) or established methods (53). Pfu enzyme (New England Biolabs) with High Fidelity buffer was employed for all amplifications. Products were sequenced to affirm fidelity prior to use. Primers are described in Table 3.

TABLE 3

| Primer | Internal reference | Sequence | Purpose |
|---|---|---|---|
| 1 | SAC2035UP | gggagctcGTTACTTGTCATTAATTAGTTACTTCC (SEQ ID NO: 55) | SacI 5' INT1 |
| 2 | MLU3'UTR | ggacgcgtTTTTATCTTTTTATGTAAATATATACTA (SEQ ID NO: 56) | MluI 3'INT1 |
| 3 | INT1 KR1595AA F | ATTGTCCAATTTTTAAGGCTGCTTTTTTCAAATTAAT GGG (SEQ ID NO: 57) | mutate Motif 1 |
| 4 | INT1 KR1595AA R | CCATTAATTTGAAAAAAGCAGCCTTAAAAATTGGAC AATC (SEQ ID NO: 58) | mutate Motif 1 |
| 5 | INT1 KK805AA F | GCATAAACAAGAAAAGCAGGCCGCCCATCAAATTC ATAAAGTTCC (SEQ ID NO: 59) | mutate Motif 4 |
| 6 | INT1 KK805AA R | GGAACTTTATGAATTTGATGGGCGGCCTGCTTTTC TTGTTTATGC (SEQ ID NO: 60) | mutate Motif 4 |
| 7 | GHISR | CTCCCGGCCGCCATGGCCGC (SEQ ID NO: 61) | check integration |
| 8 | HIS3AMP | GTTGGTGTGGCCCAGAGACTCT (SEQ ID NO: 62) | check integration |

A single copy of Int1, including 1450 bp upstream and 548 bp downstream from the Int1 open reading frame (www.candidagenome.org, Assembly 21), was integrated into the hisG locus of the int1−/− strain VBIDM2 (54) to produce the reconstituted strain KO509. Briefly, a copy of Int1 was generated by PCR, using primers 1 and 2 with BWP17wt DNA as template and cloned into the SacI/MluI sites of pGEMHIS (51) to create pKO509. pKO509 was digested with SwaI and transformed into VBIDM2 to create the reconstituted strain KO509. PCR-mediated overlap extension mutagenesis (55) was used to produce copies of Int1 mutated at putative heparin binding domains. Briefly, primer pairs 1+3 and 2+4 (or 1+5 and 2+6) were used to produce two overlapping fragments of INT1 in which putative heparin binding domains were mutated (FKKRFFKL (SEQ ID NO: 2)→FKAAFFKL (SEQ ID NO: 53) or KQKKHQ (SEQ ID NO: 64)→KQAAHQ (SEQ ID NO: 63)), and a full length mutated sequence generated in a third per using primers 1+2 with the fragments as template. The mutated sequences were cloned into the SacI/MluI sites of pGEM-HIS to create pKO503 and pKO507, respectively. A construct mutated at both sites (pKO508) was produced using primers 1+5 and 2+6 with plasmid DNA from pKO503 as template. Full length mutated products cloned into pGEM-HIS and used to transform VBIDM2 as above, producing strains KO503, KO507, and KO508. The correct insertion and orientation of all constructs was confirmed by PCR. In growth curves performed with and without 100 units/ml heparin at 30° C. in RPMI-HEPES, there was no difference in the doubling times of the wild type, Δint1 mutant, INT1 reintegrant, or the reintegrants containing alanine substitutions in Motif 1 ($_{804}$QKKHQIHK (SEQ ID NO: 1) to QAAHQIHK (SEQ ID NO: 52)), Motif 4 ($_{1593}$FKKRFFKL (SEQ ID NO: 2) to FKAAFFKL (SEQ ID NO: 53)), or Motifs 1 and 4. Percent binding of each mutant to heparin in the ELISA assay was compared to the wild type according to the formula [Absorbance$_{595}$ mutant]/[Absorbance$_{595}$ wild type]×100.

The ELISA assay used a commercially available 96-well microtiter plate coated with polymerized allylamine (BD Biosciences) (27), in which wells were inoculated with 2.5 units (12.5 μg) heparin in 100 μl phosphate buffered saline (PBS) per well. The plate was covered and allowed to stand at room temperature overnight, then washed with acetate buffer (100 mM NaCl, 50 mM NaOAc, 0.2% Tween, pH 7.2). Wells were washed three times with PBS, then inoculated with $1\times10^4$ to $4\times10^4$ *Candida albicans* yeast cells that were grown overnight at 30° C. in yeast peptone dextrose (YPD) broth, washed, and resuspended in RPMI-HEPES at $1\times10^7$ organisms/ml. The plate was then incubated at 30° C. for one hour, then washed with PBS-Tween (PBST, PBS/ 0.05% Tween). A commercially available biotinylated anti-Candida antibody (Meridian Life Science, Memphis Tenn.) was diluted 1:1500 in FACS-TWEEN (0.3% BSA/0.05% Tween), added to the wells, incubated at 30° C. for one hour, then washed with PBST. Streptavidin-alkaline phosphatase (BioLegend, San Diego Calif.) was then added to the wells at a 1:10,000 dilution in FACS-TWEEN and incubated at 30° C. for 30 min, then washed with PBST and AKP buffer (100 mM Tris, 100 mM NaCl, 50 mM $MgCl_2*6H_2O$). BluePhos@ microwell substrate (Kirkegaard and Perry Laboratories, Gaithersburg Md.) was added to the wells and allowed to react for 45 min at room temperature. The color change was read spectrophotometrically at absorbance of 595 nm.

FIGS. 4A-D show that linear heparin binding motifs in C. albicans Int1 mediate binding to heparin.

FIG. 4A illustrates the five putative heparin binding sites in Int1. Mutations were made by substituting alanine residues in Motif 1: $_{804}$QKKHQIHK (SEQ ID NO: 1) to QAAHQIHK (SEQ ID NO: 52) (Table 1, Motif 1) and in Motif 4: $_{1593}$FKKRFFKL (SEQ ID NO: 2) to FKAAFFKL (SEQ ID NO: 53) (Table 1, Motif 4). A third reintegrant had alanine substitutions at both sites.

FIG. 4B shows molecular modeling of Motif 4, which predicts that the three lysine residues and the single arginine residue (arrows) might facilitate binding to a strong anion like heparin.

Figure 4C:
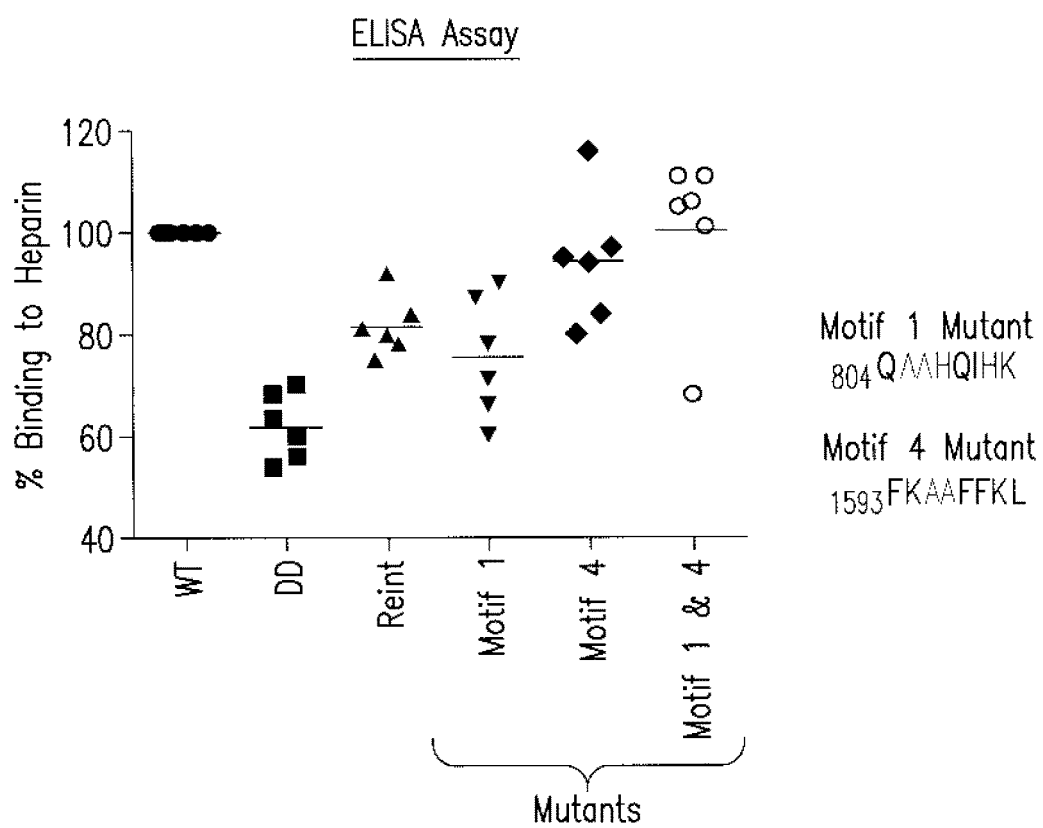

FIG. 4C shows heparin binding of C. albicans WT (normalized to 100%), Δint1 double disruptant (DD), and four single-copy reintegrants: (1) Reint contains one wild type copy of Int1; (2) Motif 1 mutant contains alanine substitutions for lysine residues at positions 805/806 ($_{804}$QAAHQIHK (SEQ ID NO: 52)); (3) Motif 4 mutant contains alanine substitutions for lysine 1595 and arginine 1596 (1593FKAAFFKL (SEQ ID NO: 53)), and (4) Motif 1&4 mutant contains alanine substitutions at both sites. Binding to heparin was highest for the wild-type C. albicans strain that expressed both copies of the INT1 gene. Disruption of both copies of INT1 (DD) reduced the binding of heparin by 40% (p=0.031) despite removing just one of the 34 C. albicans genes encoding putative linear HBM. Reintegration of one copy of the wild type INT1 gene (Reint) partially restored the ability of C. albicans to bind to heparin. Differences in heparin binding among the WT, Reint and DD strains were statistically significant (p=0.031 in all cases). Among the three isogenic strains with alanine mutations in putative heparin binding sites, mutation of Motif 1 was associated with the largest reduction in heparin binding, compared to the wild type strain (p=0.031), to the Motif 4 mutant (p=0.036), and to the Motif 1&4 mutant (p=0.031). Results with the Motif 1 mutant were not significantly different from the percent binding observed with the double disruptant (p=0.063) or the reintegrant (p=0.115), nevertheless, this trend of reduced binding suggested that lysine residues in Motif 1 might be likely mediators of heparin binding. Results are presented as mean±SD for n=5 experiments performed in quadruplicate, * p=0.031, ** p=0.036.

Figure 5:
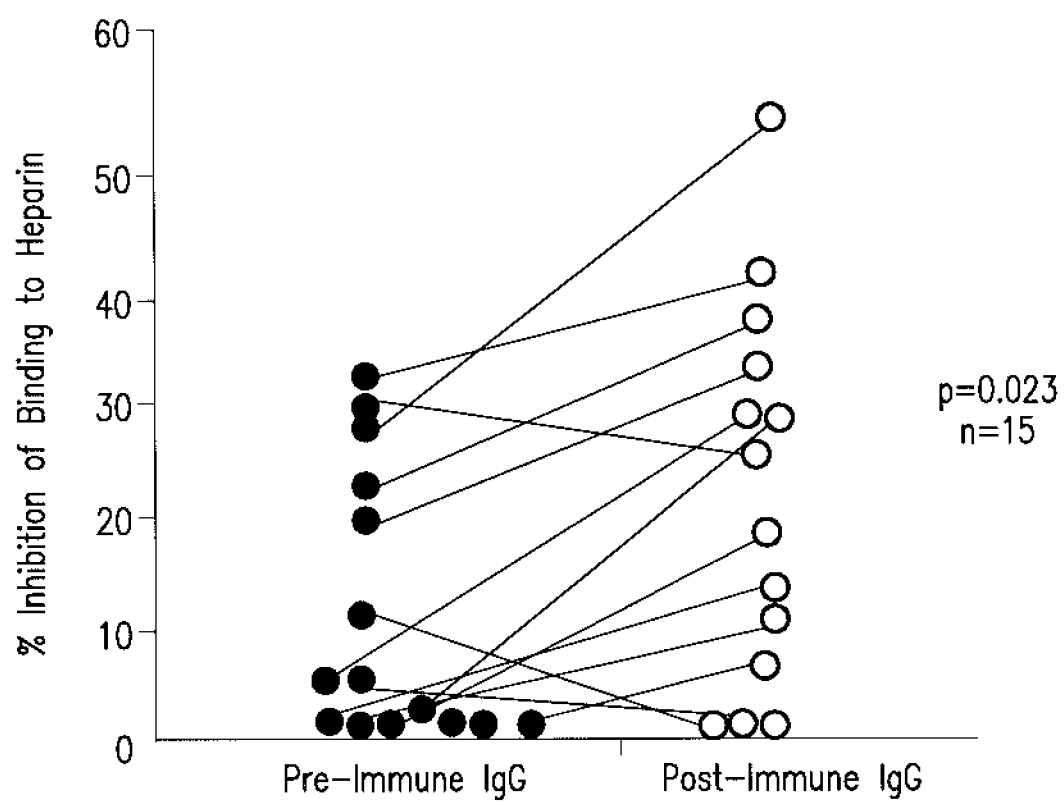

Because Motif 1 in Int1 appeared to mediate a considerable proportion of the binding of C. albicans to heparin, a peptide encompassing this motif HKQEKQKKHQIHKV (SEQ ID NO: 4) was used to immunize rabbits with a commercial protocol (Pacific Immunology). Affinity-purified immune IgG and IgG from pre-immune rabbit serum (both from Pacific Immunology) were compared for the ability to inhibit binding of C. albicans to heparin (FIG. 5). Antibody and heparin inhibition studies were performed as follows. Antibody was produced and tested by Pacific Immunology, Ramona, Calif. (www.pacificimmunology.com; NIH Animal Welfare Assurance Number A41820-01; USDA License 93-R-283). A peptide corresponding to amino acids 799-812 of Int1 (HKQEKQKKHQIHKV (SEQ ID NO: 4)), encompassing Motif 1, was conjugated to KLH via an N-terminal cysteine residue and used to immunize two NZW rabbits. The animals were immunized once with conjugated peptide in a proprietary formulation of Freund's complete adjuvant and boosted 3 times with conjugated peptide in Freund's incomplete adjuvant. The same peptide was conjugated to CNBr-Sepharose and used for affinity purification of epitope-specific IgG. The final serum titer for both animals was >1:100,000 by ELISA. Both pre-immune rabbit serum and serum from bleed 3 were chromatographed on a 2 ml Protein A column (Thermo Scientific) to yield pre- and post-immune IgG and brought to a concentration of 1.6 mg/ml. 100 μl poly-D-lysine (MP Biomedicals, Solon Ohio) diluted as 1 mg in 10 ml distilled water was added to each well of black 96-well plates (Costar) and incubated at room temperature for 60 min. After three washes with PBS, 100 μl pharmacologic heparin (2000 units/ml in RPMI-HEPES) was added to each well and incubated overnight at room temperature in the dark. In the morning, the plate was washed three times with PBS, then a 1:1000 dilution of pre- or post-immune IgG in PBS was added to each well and incubated for 30 min at room temperature. After overnight growth to mid-exponential phase in CSM, C. albicans wild type and double disruptant strains were labeled with CFSE as above. After labeling, samples of each strain were removed to determine the intensity of labeling by flow cytometry, as described above. CFSE-labeled C. albicans were diluted in RPMI-HEPES to yield $1\times10^6$ cells per 100 μl and added to each well for 60 min at 30° C. The plate was washed three times with PBS; fluorescence in each well was measured with a Beckman DTS 880. Experiments were performed in triplicate. For heparin inhibition studies, wild type C. albicans were grown as above, labeled with CFSE, and washed to remove excess CFSE. Organisms were pelleted, the supernatant was removed, and the pellets were suspended in 2 ml pharmacologic heparin (20,000 units/ml) diluted with RPMI-HEPES to a concentration of 250 units/ ml (1.3 mg/ml). CFSE-labeled C. albicans were incubated with heparin for 60 min at 37° C. with shaking at 400 RPM, then added to the wells of a black plate, incubated for 60 min at RT, and washed three times with PBS; fluorescence in each well was measured with a Beckman DTS 880. The assay was performed in a 96-well black plate with CFSE-labeled C. albicans. Wells were coated with poly-D-lysine, 100 μg/100 μl PBS for 60 min at room temperature, then 200 units heparin in 50 μl RPMI-HEPES were added to each well. The plate was incubated overnight at room temperature. The following afternoon, pre-immune IgG and post-immune IgG were diluted in PBS to a final concentration of 13.2 μg/ml. 50 μl of pre- or post-immune IgG was deposited in the appropriate well for 30 min at room temperature, then $1\times10^6$ CFSE-labeled C. albicans in 50 μl RPMI-HEPES were added for two hours at room temperature. After this incubation, the wells were washed three times with PBS, and fluorescence was measured on the multimode detector as previously described.

Polyclonal IgG to the HKQEKQKKHQIHKV (SEQ ID NO: 4) motif in domain 3 of Int1 blocked 19% of binding of wild type C. albicans (WT) to heparin. FIG. 5 shows heparin binding of wild type *C. albicans* preincubated with pre-immune IgG (left closed circles) and wild type *C. albicans* pre-incubated with post-immune IgG raised to the polypeptide HKQEKQKKHQIHKV (SEQ ID NO: 4) (right closed circles), where data represent mean±SD of n=15 experiments performed in duplicate, * p=0.023, by paired statistics. These results confirmed the importance of Motif 1, as a mediator of heparin binding in *C. albicans*.

In other systems, heparin has been reported to cleave surface proteins (56), change protein conformation (57), and bind trypsin-sensitive lysine and arginine residues in histone H1 (58). In order to understand whether incubation with heparin changed the conformation of *C. albicans* surface proteins, $1 \times 10^7$ *C. albicans* were incubated for one hour at 37° C. on a rotator with pharmacologic heparin (20,000 units/ml) diluted in RPMI-HEPES to a working concentration of 250 units/ml. *C. albicans* $1 \times 10^7$ *C. albicans* in an equal volume of RPMI-HEPES served as control. Supernatants were removed. 300 μl of Hep+ and Hep− supernatants were incubated with 100 μl avidin agarose beads (Thermo Scientific) for 60 min at room temperature on a rotator in the presence of 50 units heparin (Hep+); an equal volume of RPMI-HEPES was substituted for heparin in the Hep− supernatants. Beads were pelleted, and 100 μl beads were incubated with 100 μl 3.0 M NaCl for 30 mins at room temperature on a rotator. Beads were pelleted and the supernatants were withdrawn; 100 μl TCA was added to 100 μl Hep+ or 100 μl Hep− supernatants and incubated on ice overnight at 4° C. The TCA precipitates were stored at −80° C. until analysis by mass spectroscopy.

Six biological replicates of TCA precipitated protein pellets from equal cellular equivalence of heparin-treated (Hep+) and untreated (Hep−) conditioned medium from cultures of *C. albicans* were each solubilized in 50 μL Laemmli gel buffer. To remove any residual TCA and to further concentrate the samples, each was subjected to buffer exchange and concentration using an Amicon ultra 3 kDa microfuge filtration cartridge at 14,000×g for 15 min with five subsequent additions of 50 μL of 1× Laemmli gel buffer between spins. The resulting retained proteins (6 Hep+ and 6 Hep−) were subsequently prepared for SDS-PAGE by combining into two pools of three samples for the Hep+ and Hep− conditioned medium. The replicate sample pools were loaded onto two 4-12% mini gels and separated using the MOPS buffer system followed by silver staining to visualize the proteins using the Sigma Proteosilver system. The proteins were prepared for identification and quantitation by mass spectrometry by gridding the gel lanes from the replicates of Hep+ and Hep− samples into 11 equal regions followed by in gel trypsin digestion and extraction of peptides as described (59).

The recovered peptides from the gridded gel sections were analyzed by liquid chromatography coupled nano-electrospray mass spectrometry (nLC-MSMS) on a TripleTOF 5600 mass spectrometer (AB Sciex, Toronto Canada) attached to an Eksigent (Dublin Calif.) nanoLC ultra nano-flow system. Recovered peptides from each fraction were loaded on to IntegraFrit Trap Column (outer diameter of 360 μm, inner diameter of 100, and 25 μm packed bed) from New Objective, Inc. (Woburn Mass.) at 2 μl/min in FA/H2O 0.4/99.2 (v/v) for 10 min to desalt and concentrate the samples. For the chromatographic separation of peptides, the trap-column was switched to align with the analytical column, Acclaim PepMap100 (inner diameter of 75 μm, length of 15 cm, C18 particle sizes of 3 μm and pore sizes of 100 Å) from Dionex-Thermo Fisher Scientific (Sunnyvale Calif.). The peptides were eluted using a linear gradient from 95% phase A (FA/H2O 0.4/99.6, v/v) to 40% phase B (FA/ACN 0.4/99.6, v/v) from 5 min to 22.5 min (2% ACN/min) at a flow of 300 nL/min. As the peptides eluted from the column they were sprayed into the mass spectrometer using NANOSpray® III Source (AB Sciex, Toronto Canada). Ion source gas 1 (GS1), ion source gas 2 (GS2) and curtain gas (CUR) were respectively kept at 7, 0 and 25 vendor specified arbitrary units. Interface heater temperature and ion spray voltage was kept at 150 C, and at 2.3 kV respectively. Mass spectrometer method was operated in positive ion mode set to go through 25 minutes, where each cycle performing one TOF-MS scan type (0.25 sec accumulation time, in a 400 to 1600 m/z window) followed by twenty information dependent acquisition (IDA)-mode MS/MS-scans on the most intense candidate ions selected from initially performed TOF-MS scan during each cycle having a minimum 150 counts. Each product ion scan was operated under vender specified high-sensitivity mode with an accumulation time of 0.05 sec and a mass tolerance of 50 mDa. Former MS/MS-analyzed candidate ions were excluded for 10 sec after its first occurrence, and data were recorded using Analyst®-TF (1.5.1) software.

NanoLC-MSMS data collected from the Hep+ and Hep− samples were converted to Mascot generic files and searched against the SwissProt fungal database on an in house server running Mascot version 2.2.07 (Matrix Science, Ltd). Specific search parameters included up to two missed tryptic cleavages, carbamidomethylation of Cys, oxidation of Met, peptide and fragmentation mass tolerance of 0.1 Da. Only proteins with a minimum of two peptides with Mascot peptide score indicating a peptide identity and a false discovery rate (FDR) against and inverse database at less than 1% were reported. Semi-quantitative measurements between the Hep+ and Hep− proteins were generated using a minimum of two tryptic peptides from each protein as surrogates for the amount of proteins from the two groups. This was accomplished by capturing extracted ion profiles for each peptide and then comparing the mono-isotopic peak intensity at the apex of the signal for the M+2H or M+3H signal for each peptide. An average ratio of the maximal peak intensity between two independent peptides for each protein presented was used to determine semi-quantitative ratios of proteins between the Hep+ and Hep− samples.

To determine the levels of these proteins in control versus heparin-treated organisms, the relative level of several tryptic peptides were used as surrogates for the protein levels.

Figure 6A:
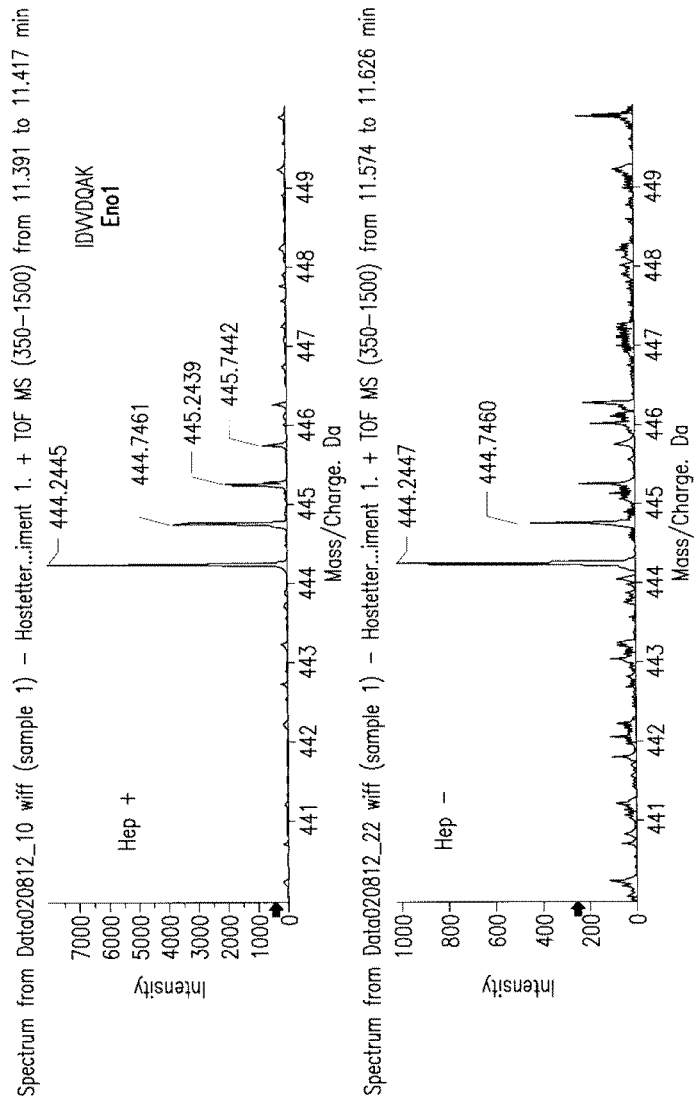
Figure 6B:
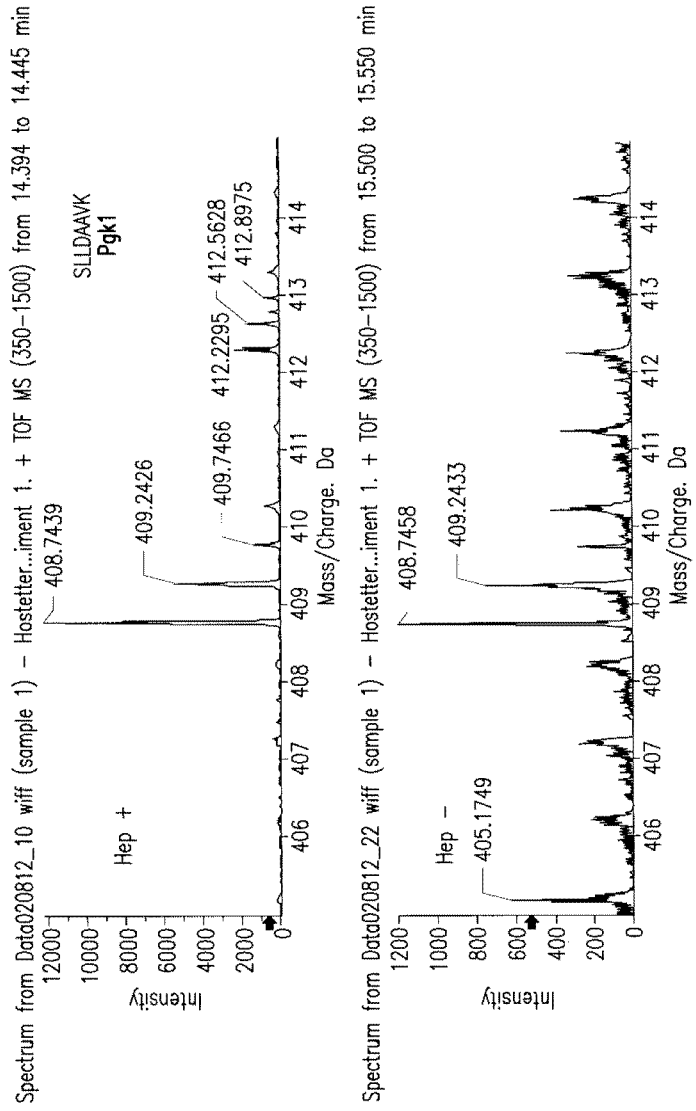
Figure 6C:
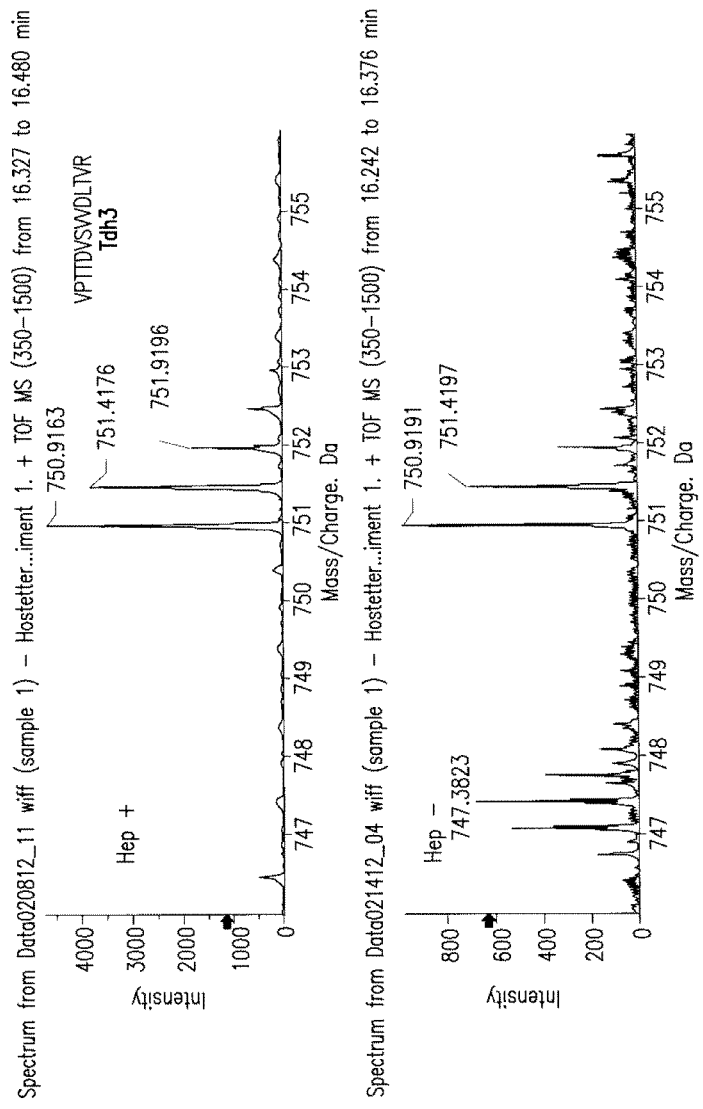

Compared to untreated organisms, heparin treatment led to a seven-fold increase in intensity of IDVVDQAK (SEQ ID NO: 65) from Eno1 (FIG. 6A), a ten-fold increase in intensity of SLLDAAVK (SEQ ID NO: 66) from Pgk1 (FIG. 6B), and a five-fold increase in VPTTDVSVVDLTVR (SEQ ID NO: 67) from Tdh3 (FIG. 6C) in supernatants.

Other peptides from Eno1, Pgk1, and Tdh3 also exhibited increased intensities, ranging from 10-16 fold the intensity of the corresponding peptides from untreated organisms (data not shown), further validating significant increases in the protein levels in the supernatants for heparin-treated cultures. Of the 12 proteins whose peptides were found in highest concentration in the supernatant (Table 4), all but one are known to be localized to the cell wall; cellular localization of Eft1 is not known. Eight of the twelve, including Eno1, Pgk1, Tdh3 and Ssa1/2, themselves contain putative heparin binding motifs (Table 1) and are considered critical antigens for innate and adaptive immune responses against *C. albicans* (31-36).

TABLE 4

| ID | Prot Score | Prot Mass | Peptide Matches** |
|---|---|---|---|
| Eno1*,# | 2877 | 47202 | 213 |
| Ssa2*,# | 1938 | 70199 | 73 |
| Pgk1*,# | 1826 | 45266 | 131 |
| Tdh3*,# | 1751 | 35508 | 192 |
| Hsp90# | 1666 | 80773 | 65 |
| Ssb1*,# | 1608 | 66562 | 82 |
| Met6# | 1566 | 85763 | 70 |
| Ssa1*,# | 1455 | 70452 | 61 |
| Adh1# | 1218 | 37255 | 67 |
| Eft1 | 1187 | 50426 | 99 |
| Ino1*,# | 1006 | 57857 | 39 |
| Eft2*,# | 933 | 93865 | 25 |

*proteins with putative linear heparin binding motifs;
**total peptides identified by MSMS including duplicates; and
cell wall proteins by Gene Ontology.

In order to evaluate the consequences of removal of Ssa1 and Ssa2 (Table 4), both targets of histatin, a histatin killing assay was performed as follows. C. albicans strains were grown to late log phase overnight in YPD. A single colony was suspended in 1 ml YPD, diluted 1:500 into 10 ml YPD, and incubated overnight at 30° C. and 225 rpm to $OD_{600}$ 1.0. Yeast cells were washed twice in PBS and $2 \times 10^4$ cells suspended in 250 µl RPMI+10 mM HEPES, pH 7.0, with or without 500 units/ml heparin (Sigma). The cells were incubated at 37° C. for one hour with shaking, washed twice with 10 mM phosphate buffer, pH 7.4, and suspended in 20 µl phosphate buffer. Histatin 5 (final concentration 15 µM; Peptides International) or 10 mM phosphate buffer was added to the preincubated cells (total volume 40 µl) and incubated further at 37° C. for 90 minutes with shaking. YPD (360 µl) was added to each tube, a 40 µl aliquot spread onto YPD plates, and colonies counted after two days. The effect of heparin treatment was determined by the formula % change=[(cfu+heparin)−(cfu−heparin)]/(cfu+heparin).

Heparin binding to trypsin-sensitive lysine and arginine residues in histone H1 unfolds chromatin and increases its accessibility (58). To test whether heparin binding could influence gene expression in C. albicans, qRT-PCR was performed on a selective set of 13 genes involved in adhesion, cell-cell interaction, and biofilm formation after incubating C. albicans with and without 100 units/ml heparin at 37° C. for 75 minutes. Gene expression studies were performed as follows. Overnight cultures (3 ml YPD at 30° C., 225 rpm) were diluted in 25 ml YPD to a nominal concentration of $8 \times 10^5$/ml and grown to $OD_{600}$ approximately 1.0 (30° C., 225 rpm), collected by centrifugation, and washed in PBS. Cells ($5 \times 10^7$) were suspended in 5 ml RPMI1640 with 25 mM MOPS pH7.4, with or without 100 units/ml Sigma heparin in 50 ml polypropylene tubes, and incubated at 37° C. with shaking for 75 minutes. One ml aliquots (approximately $10^7$ cells) were collected by centrifugation, washed once with room temperature PBS, and frozen at −80°. Pellets were thawed on ice and suspended in 1 ml Tri-Reagent (MRC Research) in a 2 ml screw capped tube containing about 0.2 g acid washed glass beads (Sigma) and vortexed three times for 1 minute with a 1 minute rest on ice between each vortex. The lysates were rested for five min at room temperature, centrifuged for five min at 12,000 rpm, and RNA isolated from the supernatant using the DirectZol kit (Zymo), including DNAse digestion, per manufacturer's instructions. cDNA was produced from equivalent quantities of RNA (between 300 and 900 ng) for each treatment using the Maxima Reverse Transcriptase Kit for qRT-PCR (Fermentas). Two µl of 1:5 dilution of cDNA was used in each qPCR reaction with 500 nM of each primer and Fast SYBR Green Master Mix (Life Technologies) on a 7500 FAST Instrument (Applied Biosystems) according to manufacturer's instructions. Relative expression was determined using the ΔΔCt method (60) with 18S RNA as the reference. Primers are shown in Table 5.

TABLE 5

| Primer | Sequence | SEQ ID NO |
|---|---|---|
| 18S F | TCTTGTGAAACTCCGTCGTG | 68 |
| 18S R | AGGGACGTAATCAACGCAAG | 69 |
| AHP1 F | TGTGCCTGGTGCTTTTACC | 70 |
| AHP1 R | TTAGCCCAAGCTGCCATTAC | 71 |
| ALS1 F | TCATTTGCCACCACTACCAC | 72 |
| ALS1 R | TGGCATAGGATTGTGACCAG | 73 |
| ALS3b F | GCTGGTGGTTATTGGCAACGTGC | 74 |
| ALS3b R | TGGTAAGGTGGTCACGGCGG | 75 |
| CDC10 F | AGATCAAGGGCAAACCTCAC | 76 |
| CDC10 R | ATAGGAGCATTTGGCACACC | 77 |
| EAP1 F | TACCCAGGCCAATACAAAGG | 78 |
| EAP1 R | TAATGGGCTTGACCTTGGAG | 79 |
| ECE1 F | CTAATGCCGTCGTCAGATTG | 80 |
| ECE1 R | AACATCTGGAACGCCATCTC | 81 |
| ENO1 F | CCATTGACAAAGCCGGTTAC | 82 |
| ENO1 R | TTAGATGGGTCGGATTCTGG | 83 |
| HGC1 F | AGGTCGCAAGCAACAACAAC | 84 |
| HGC1 R | AAGAAACAGCACGAGAACCAG | 85 |
| HWP1b F | TCCTGCCACTGAACCTTCCCCAG | 86 |
| HWP1b R | CCACTTGAGCCAGCTGGAGCG | 87 |
| HWP2 F | CCACCAAAACCAAGTGCTAC | 88 |
| HWP2 R | AACTCCAGATGATCCCGAAG | 89 |
| INT1 F | TGTGCCCACTGAAGTCAAAG | 90 |
| INT1 R | GCTTTACCGGTGATTTGGTC | 91 |
| RBT1 F | CACCTCATGCTCCAACAATG | 92 |
| RBT1 R | GATGATTCTGGGGCTGATTC | 93 |
| RBT5 F | TGCTGAAAGTTCTGCACCAG | 94 |
| RBT5 R | GCTTCAACGGAAACAGAAGC | 95 |

Figure 7A:
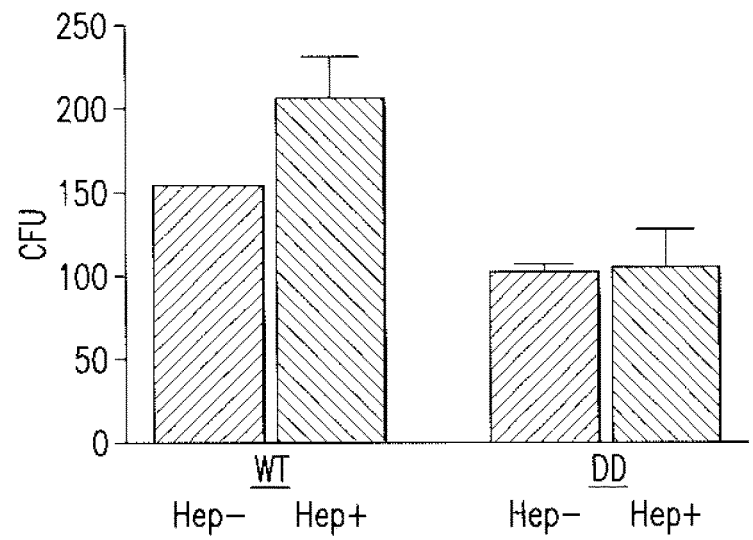

FIG. 7A shows CFU of C. albicans WT and DD after 75-minute incubation without (left bar of each set) or with (right bar of each set) 500 units/ml heparin followed by histatin 5 (15 µM), performed in duplicate. Confirming proteomic results showing removal of Ssa1/2 (Table 3), incubation of wild type C. albicans with 500 units/ml heparin led to a 25% decrease in histatin-mediated killing (FIG. 7A); in contrast, heparin treatment of the INT1 double disruptant did not impair killing (1.5% decrease).

Figure 7B:
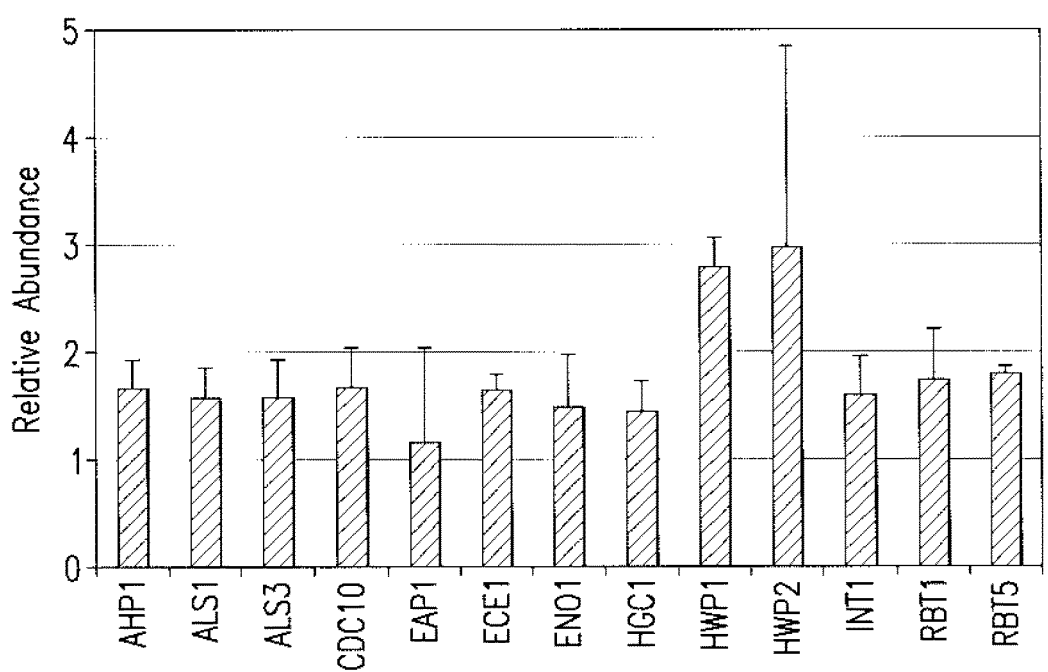

FIG. 7B shows relative mRNA expression of thirteen genes measured by qRT-PCR after incubation of C. albicans with heparin, with the level of expression compared to C.

albicans without heparin (=1). Results showed a 2.5 to 3-fold increase in mRNA for HWP1 and HWP2.

In order to understand whether heparin binding motifs 1 and 4 influenced *C. albicans* pathogenesis in vivo, we employed a rat model of biofilm formation in central venous catheters inserted into the jugular vein, as previously described (61). After insertion into the jugular vein of an anesthetized female Sprague-Dawley rat, a silastic catheter was heparinized with 100 units heparin/ml and remained in place for 24 hours. At the 24 hour timepoint, 500 µl of blood was withdrawn and cultures to insure sterility, and then 1×10$^6$ CFU of the desired *C. albicans* strain was instilled into the catheter and allowed to dwell for 6 hours. The animal was then sacrificed, the catheter was removed aseptically and processed for scanning electron microscopy. Biofilm formation on the intra-luminal surface of the catheter was assessed by scanning electron microscopy (SEM) at 100× and 2000×.

FIGS. 8A-F demonstrated that heparin binding motifs contribute to biofilm formation in vivo.

Figure 8A:
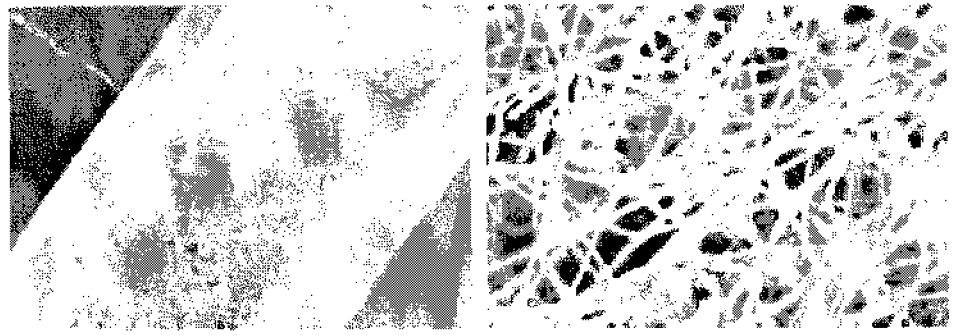
Figure 8B:
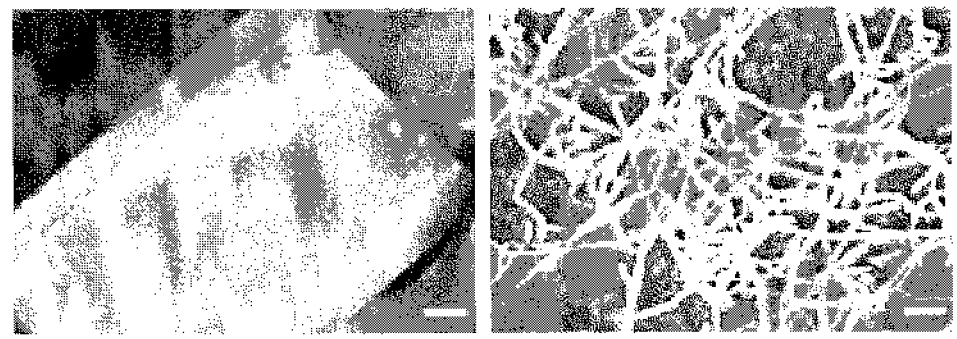
Figure 8C:
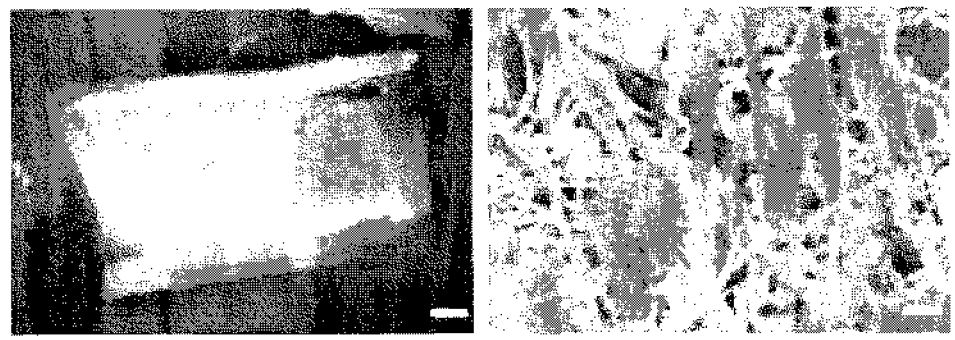
Figure 8D:
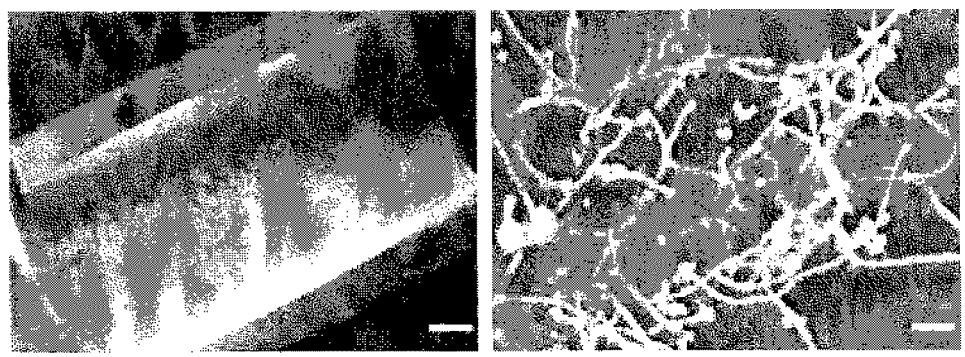
Figure 8E:
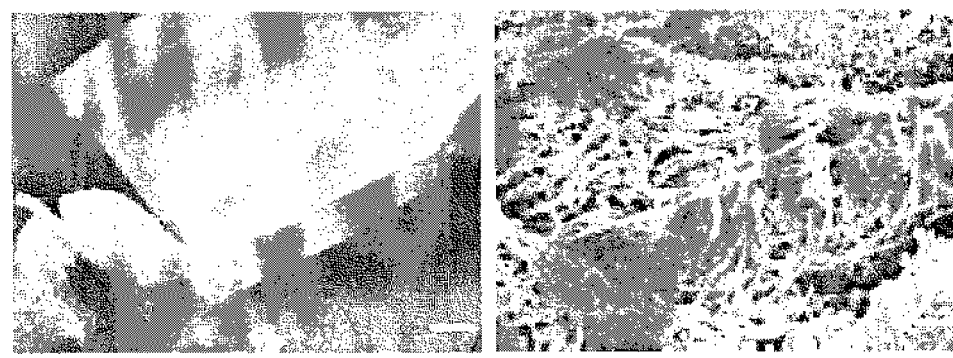
Figure 8F:
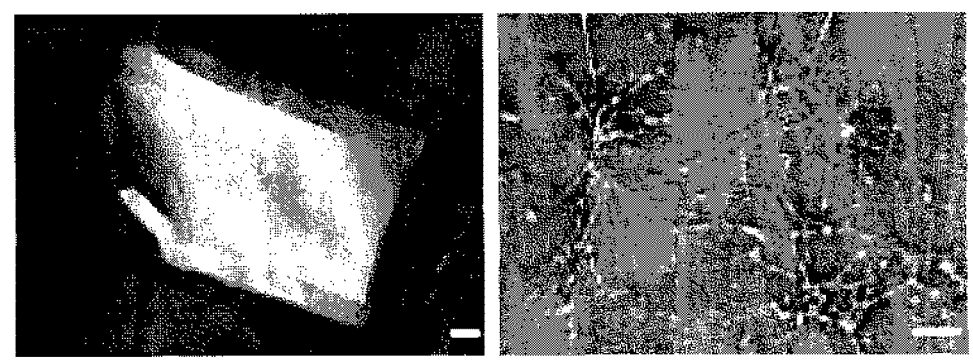

The INT1 wild type strain (WT) produced a profuse biofilm with intertwined hyphae and visible exopolysaccharide matrix (FIG. 8A). Biofilm formation by the Int1 double disruptant was much reduced on SEM (FIG. 8B), as expected. Reintegration of one wild type copy of INT1 restored a profuse biofilm (FIG. 8C). However, alanine substitution of lysines$_{805/806}$ in Motif 1 greatly impaired biofilm formation (FIG. 8D). Although alanine substitution of lysine$_{1595}$ and arginine$_{1596}$ in Motif 4 did not reduce biofilm formation (FIG. 8E), the Motif 1&4 mutant again produced sparse biofilm (FIG. 8F). These results showed that lysine residues 805/806 in Motif 1 were critical for biofilm formation in vivo.

Inhibition of biofilm formation by the antibody raised against the peptide sequence HKQEKQKKHQIHKV (SEQ ID NO:4) was also tested in the rat central venous catheter model. A 1:10 dilution of affinity-purified IgG against the peptide HKQEKQKKHQIHKV (SEQ ID NO: 4) was incubated with wild type *C. albicans* at 30° C. for one hour. A 1:10 dilution of pre-immune IgG was used as a control. The strains were then instilled into separate jugular venous catheters in individual rats. After 6 hours, catheters were removed and aseptically processed for scanning electron microscopy (100× and 2000×) as described above.

Figure 9:
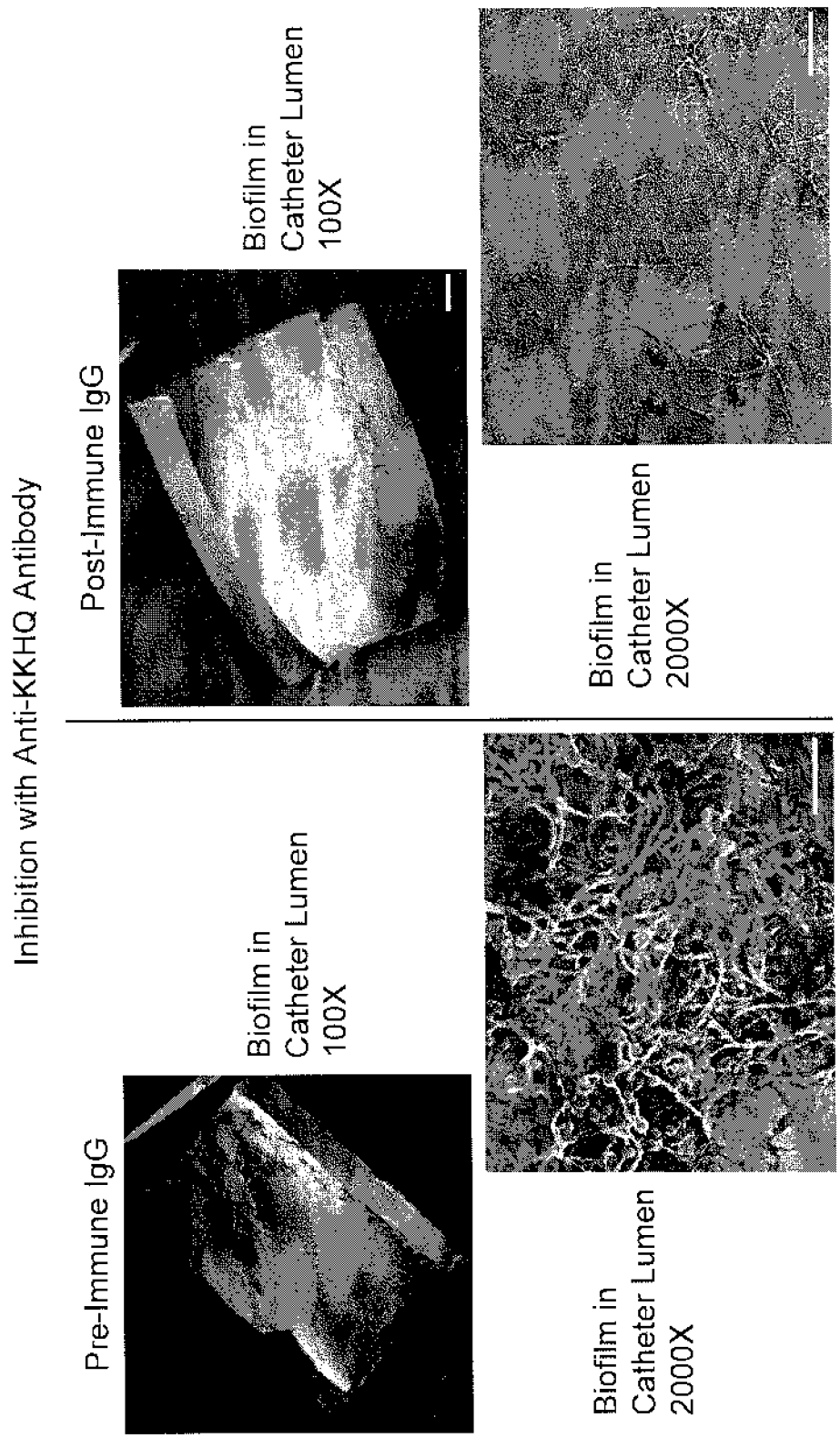

Central venous catheters from animals that received *C. albicans* pre-incubated with IgG against HKQEKQKKHQIHKV (SEQ ID NO:4) exhibited substantially reduced biofilm formation. FIG. 9 (left panel) shows intraluminal biofilm (100× and 2000×) from *C. albicans* incubated with pre-immune IgG; there is no diminution in biofilm, hyphae, or production of exopolysaccharide matrix. FIG. 9 (right panel) shows intraluminal biofilm (100× and 2000×) from *C. albicans* incubated with post-immune IgG recognizing the sequence HKQEKQKKHQIHKV (SEQ ID NO: 4); there is a marked diminution in biofilm with sparse hyphae and no matrix.

In vitro study results showed that *C. albicans* binds heparin through HBM in Int1 (FIG. 4C). The specificity of this interaction was confirmed by inhibition with heparin (data not shown) and with antibodies directed against a peptide that encompasses Motif 1 in Int1 (FIG. 5). Binding of heparin results in several consequences that could potentially impact virulence in vivo: removal of *Candida* surface proteins that serve as targets for innate (FIG. 7A) and adaptive (FIG. 6A-C) immune defenses and modulation of gene expression (FIG. 7B).

The in vivo studies of biofilm formation in heparinized central venous catheters in rats showed an obvious reduction in biofilm formation after mutation of lysine residues 805/806 in Motif 1 (FIGS. 8D, 8F). In addition, a rabbit IgG antibody directed against a peptide encompassing Motif 1 dramatically inhibited biofilm formation in the rat central venous catheter model as well (FIG. 9, right panel). These results not only demonstrate the central role of lysine residues in Motif 1 but also have important clinical implications because of the use of heparin in central venous catheters, in which setting *Candida* spp. are the fourth most common cause of infections (23, 24).

Putative linear HBM are also present in *Staphylococcus epidermidis* and *Staphylococcus aureus* (Long and Hostetter unpublished data), two organisms that are even more common causes of catheter-associated infection (43), as shown in Tables I-IV. For example, putative linear HBM were identified in the following cell wall or putative cell wall proteins, where the motif and the beginning position of the motif is indicated in parenthesis, from methicillin resistant *Staphylococcus aureus*, strain 252 (MRSA252): sasC (LKKNKY; 4; and IRKYKV; 11), isdB (YKKAKT; 289), sasF (SRRNKL; 618), glcB (IRKFKL; 415), sasA (MHHTHS; 1263), SAR0879 (LKKIKG; 573), SAR0986 (YRHLKP; 754), SAR1559 (IRKAHQ; 206), SAR2393 (PKRKVVKI; 149), and sasG (VRKARS; 140); from methicillin sensitive *Staphylococcus aureus*, strain 476 (MSSA476): SAS2383 (VRKARS; 140; and VKKSKI; 1319), SAS1682 (LKKNKY; 4; and IRKYKV; 11), SAS1063 (YKKAKT; 282), SAS1657 (YHKAKT; 484), SAS2532 (SRRNKL; 626), SAS2540 (MHHTHS; 2187), SAS0082 (LKKIKG; 573), SAS1011 (IRKAHQ; 206), SAS2035 (PKRKVVKI; 149), and SAS2424 (IRKFKL; 415); and from *Staphylococcus epidermidis*, strain RP62A: SERP1316 (FRKQKF; 4; VHRLKV; 352; and IHKIKP; 3234), SERP0660 (LKKWKV; 4; and IRRAHQ; 212), SERP0719 (TRKNHY; 13), SERP1482 (VKRFKN; 1730), SERP1654 (MKKSKV; 1), SERP2264 (MKRIKT; 393), SERP0207 (NRKNKN; 887), and SERP1691 (PKKIKN; 72).

In one embodiment, an antibody is generated against a linear heparin binding motif which is conserved among MSSA, MRSA, and *S. epidermidis*. In one embodiment, the conserved heparin binding motif is selected from the group consisting of LKKNKY, LKKNKY, LKKWKV, LKKIKG, LKKIKG, VRKARS, VRKARS, YKKAKT, YKKAKT, YHKAKT, PKRKVVKI, PKRKVVKI, IRKAHQ, IRKAHQ, and IRRAHQ.

Putative linear HBM were identified in the following cell wall or putative cell wall proteins from various yeast species, as shown in Table V where a check mark indicates that the motif is identical to the motif found in *C. albicans*, including *C. dubliniensis* (Int1 (YKKRFFKL), Eno1 (AKKGKF), and Tdh3 (GHKIKV) proteins), *C. parapsilosis* (Tdh3 protein (GHKIKV)), *C. tropicalis* (Int1 (FKRRFFKL), and Tdh3 (GHKIKV) proteins), *C. glabrata* (Int1 (FKKRFFTL) protein), *Lodderomyces elongisporus* (Int1 (FKKFIFKL) and Tdh3 (GHKIKV) proteins), and *A. nidulans* (Int1 (FKKRFFKL) protein). In embodiments, an antibody directed to a region of these proteins containing the putative HBM or the region of these proteins containing the putative HBM may be used in the described methods.

TABLE I

Methicillin resistant *Staphylococcus aureus*, strain 252 MRSA252

| GI Accession | Name | Description | "Cell wall" in Description | "Cell wall" in GO annotation | Have signaling peptide | Motif in Sequence | Motif | Start Location |
|---|---|---|---|---|---|---|---|---|
| GI: 49484003 | sasC | putative surface anchored protein | | | Yes | Yes | LPNTG | 2153 |
| GI: 49483291 | isdB | iron-regulated heme-iron binding protein | | | Yes | Yes | LPQTG | 616 |
| GI: 49484843 | sasF | putative surface anchored protein | | | Yes | Yes | LPKAG | 588 |
| GI: 49484739 | glcB | PTS system, glucose-specific IIABC component | | | | Yes | LPAAG | 22 |
| GI: 49484850 | sasA | putative serine rich repeat containing protein | | | | Yes | LPDTG | 1308 |
| GI: 49482351 | SAR0879 | putative myosin-crossreactive antigen | | | | Yes | LPKAG | 57 |
| GI: 49482500 | SAR0986 | putative nitric oxide reductase | | | | Yes | LPSAG | 230 |
| GI: 49483239 | SAR1559 | putative cobalt transport protein | | | | Yes | LPITG | 258 |
| GI: 49484356 | SAR2393 | hypothetical protein | | | | Yes | LPTAG | 177 |
| | sasG | virulence associated cell wall protein | | | | | | |

| GI Accession | Ortholog in MSSA476 | MSSA476 ortholog has motif? | Ortholog in RP62A | RP62A orthology has motif: | Have heparin binding motif? | # of heparin binding motifs |
|---|---|---|---|---|---|---|
| GI: 49484003 | SAS1682 | Yes | SERP1316 | Yes | Yes | 2 |
| GI: 49483291 | SAS1063 | Yes | | | Yes | 1 |
| GI: 49484843 | SAS2532 | Yes | SERP2264 | Yes | Yes | 1 |
| GI: 49484739 | SAS2424 | Yes | | | Yes | 1 |
| GI: 49484850 | SAS2540 | Yes | GI: 57865710 | No | Yes | 1 |
| GI: 49482351 | SAS0082 | Yes | GI: 57866574 | No | Yes | 1 |
| GI: 49482500 | | | | | Yes | 1 |
| GI: 49483239 | SAS1011 | Yes | SERP0660 | Yes | Yes | 1 |
| GI: 49484356 | SAS2035 | Yes | SERP1739 | Yes | Yes | 1 |
| | | | | | Yes | 1 |

| GI Accession | Motif 1 type | Motif 1 seq | Motif after | Motif 2 type | Motif 2 seq | Motif after |
|---|---|---|---|---|---|---|
| GI: 49484003 | Cardin | LKKNKY | 3 | Cardin | IRKYKV | 10 |
| GI: 49483291 | Cardin | YKKAKT | 288 | | | |
| GI: 49484843 | Cardin | SRRNKL | 617 | | | |
| GI: 49484739 | Cardin | IRKFKL | 414 | | | |
| GI: 49484850 | Cardin | MHHTHS | 1262 | | | |
| GI: 49482351 | Cardin | LKKIKG | 572 | | | |
| GI: 49482500 | Cardin | YRHLKP | 753 | | | |
| GI: 49483239 | Cardin | IRKAHQ | 205 | | | |
| GI: 49484356 | Wentraub | PKRKVVKI | 148 | | | |
| | Cardin | VRKARS | 139 | found by MKH | | |

TABLE II

Methicillin sensitiveie *Staphylococcus aureus*, strain 476 MSSA476

| ID MSSA476 | refSeq | GI Accession | Name | Description | "Cell wall" in Description | "Cell wall" in GO annotation |
|---|---|---|---|---|---|---|
| SAS2383 | YP_044496.1 | GI: 49487275 | SAS2383 | putative cell wall-anchored protein | Yes | Yes |
| SAS1682 | YP_043802.1 | GI: 49486581 | SAS1682 | putative surface anchored protein | | |
| SAS1063 | YP_043187.1 | GI: 49485966 | SAS1063 | iron-regulated heme-iron binding protein | | Yes |
| SAS1657 | YP_043776.1 | GI: 49486555 | SAS1657 | haptoglobin-binding surface anchored protein | | Yes |
| SAS2532 | YP_044646.1 | GI: 49487425 | SAS2532 | putative surface anchored protein | | |
| SAS2540 | YP_044654.1 | GI: 49487433 | SAS2540 | putative cell wall-anchored protein | Yes | Yes |
| SAS0082 | YP_042206.1 | GI: 49484985 | SAS0082 | putative myosin-crossreactive antigen | | |
| SAS1011 | YP_043135.1 | GI: 49485914 | SAS1011 | putative cobalt transport protein | | |

TABLE II-continued

Methicillin sensitiveie *Staphylococcus aureus*, strain 476 MSSA476

| | | | | |
|---|---|---|---|---|
| SAS2035 | YP_044146.1 | GI: 49486925 | SAS2035 | hypothetical protein |
| SAS2424 | YP_044538.1 | GI: 49487317 | SAS2424 | PTS system, glucose-specific IIABC component |

| ID MSSA476 | Have signaling peptide | Motif in Sequence | Motif | Start Location | Ortholog in MRSA252 | MRSA252 ortholog has motif? | Ortholog in RP62A | RP62A orthology has motif? | Have heparin binding motif? |
|---|---|---|---|---|---|---|---|---|---|
| SAS2383 | Yes | Yes | LPKTG | 1338 | sasG | | aap | Yes | Yes |
| SAS1682 | Yes | Yes | LPNTG | 2150 | sasC | Yes | SERP1316 | Yes | Yes |
| SAS1063 | Yes | Yes | LPQTG | 609 | isdB | Yes | | | Yes |
| SAS1657 | Yes | Yes | LPKTG | 860 | | | | | Yes |
| SAS2532 | Yes | Yes | LPKAG | 596 | sasF | Yes | SERP2264 | Yes | Yes |
| SAS2540 | | Yes | LPDTG | 2232 | sasA | Yes | GI: 57865710 | No | Yes |
| SAS0082 | | Yes | LPKAG | 57 | SAR0879 | Yes | GI: 57866574 | No | Yes |
| SAS1011 | | Yes | LPITG | 258 | SAR1559 | Yes | SERP0660 | Yes | Yes |
| SAS2035 | | Yes | LPTAG | 177 | SAR2393 | Yes | SERP1739 | Yes | Yes |
| SAS2424 | | Yes | LPAAG | 22 | glcB | Yes | | | Yes |

| ID MSSA476 | # of heparin binding motifs | Motif 1 type | Motif 1 seq | Motif after | Motif 2 type | Motif 2 seq | Motif after |
|---|---|---|---|---|---|---|---|
| SAS2383 | 2 | Cardin | VRKARS | 139 | Cardin | VKKSKI | 1318 |
| SAS1682 | 2 | Cardin | LKKNKY | 3 | Cardin | IRKYKV | 10 |
| SAS1063 | 1 | Cardin | YKKAKT | 281 | | | |
| SAS1657 | 1 | Cardin | YHKAKT | 483 | | | |
| SAS2532 | 1 | Cardin | SRRNKL | 625 | | | |
| SAS2540 | 1 | Cardin | MHHTHS | 2186 | | | |
| SAS0082 | 1 | Cardin | LKKIKG | 572 | | | |
| SAS1011 | 1 | Cardin | IRKAHQ | 205 | | | |
| SAS2035 | 1 | Wentraub | PKRKVVKI | 148 | | | |
| SAS2424 | 1 | Cardin | IRKFKL | 414 | | | |

TABLE III

*Staphylococcus epidermidis*, strain RP62A Strain RP62A

| ID RP62A | refSeq | GI Accession | Name | Description | "Cell wall" in Description | "Cell wall" in GO annotation |
|---|---|---|---|---|---|---|
| SERP1316 | YP_188888.1 | GI: 57867198 | SERP1316 | cell wall surface anchor family protein | | Yes |
| SERP0660 | YP_188245.1 | GI: 57866567 | SERP0660 | cobalt transport family protein | | |
| SERP0719 | YP_188302.1 | GI: 57866639 | SERP0719 | cell wall surface anchor family protein | | Yes |
| SERP1482 | YP_189048.1 | GI: 57867352 | SERP1482 | cell wall surface anchor family protein | | Yes |
| SERP1654 | YP_189219.1 | GI: 57867536 | SERP1654 | cell wall surface anchor family protein | | Yes |
| SERP2264 | YP_189815.1 | GI: 57865679 | SERP2264 | cell wall surface anchor family protein | | Yes |
| SERP0207 | YP_187803.1 | GI: 57866125 | SERP0207 | sdrG protein | | |
| SERP1691 | YP_189256.1 | GI: 57867615 | SERP1691 | cell division protein, FtsW/RodA/SpoVE family | | |

| ID RP62A | Have signaling peptide | Motif in Sequence | Motif | Start Location | Ortholog in MSSA476 | MSSA476 ortholog has motif? | Ortholog in MRSA252 | MRSA252 orthology has motif? | Have heparin binding motif? | # of heparin binding motifs |
|---|---|---|---|---|---|---|---|---|---|---|
| SERP1316 | Yes | Yes | LPEAG | 3654 | SAS1682 | Yes | sasC | Yes | Yes | 3 |
| SERP0660 | | Yes | LPITG | 264 | SAS1011 | Yes | SAR1559 | Yes | Yes | 2 |
| SERP0719 | Yes | Yes | LPETG | 787 | | | | | Yes | 1 |
| SERP1482 | Yes | Yes | LPDTG | 1937 | | | | | Yes | 1 |
| SERP1654 | Yes | Yes | LPETG | 165 | | | | | Yes | 1 |
| SERP2264 | Yes | Yes | LPATG | 639 | SAS2532 | Yes | sasF | Yes | Yes | 1 |
| SERP0207 | | Yes | LPDTG | 852 | SAS0521 | Yes | bbp | Yes | Yes | 1 |
| SERP1691 | Yes | Yes | LPITG | 352 | SAS1988 | Yes | SAR2371 | Yes | Yes | 1 |

| ID RP62A | Motif 1 type | Motif 1 seq | Motif after | Motif 2 type | Motif 2 seq | Motif after | Motif 3 type | Motif 3 seq | Motif after |
|---|---|---|---|---|---|---|---|---|---|
| SERP1316 | Cardin | FRKQKF | 3 | Cardin | VHRLKV | 351 | Cardin | IHKIKP | 3233 |
| SERP0660 | Cardin | LKKWKV | 3 | Cardin | IRRAHQ | 211 | | | |
| SERP0719 | Cardin | TRKNHY | 12 | | | | | | |
| SERP1482 | Cardin | VKRFKN | 1729 | | | | | | |
| SERP1654 | Cardin | MKKSKV | 0 | | | | | | |

TABLE III-continued

Staphylococcus epidermidis, strain RP62A
Strain RP62A

| | | | |
|---|---|---|---|
| SERP2264 | Cardin | MKRIKT | 392 |
| SERP0207 | Cardin | NRKNKN | 886 |
| SERP1691 | Cardin | PKKIKN | 71 |

TABLE IV

Linear Heparin Binding Motifs Conserved Among 2 or 3 Staphylococcus species

| | | | | | | | | | | |
|---|---|---|---|---|---|---|---|---|---|---|
| MRSA | sasC | | LKKNKY | sar0879 | LKKIKG | sasG | VRKARS | isdB | YKKAKT | sar2892 |
| MSSA | sasC | | LKKNYY | sas0082 | LKKIKG | sas2383 | VRKARS | sas1063 | YKKAKT sas1657 YHKAKT | sas2035 |
| St. epi | serp0660 | LKKWKV | | | | | | | | |

| | | | | |
|---|---|---|---|---|
| MRSA | PKRKVVKI | sar1559 | IRKAHQ | |
| MSSA | PKRKVVKI | sas1011 | IRKAHQ | |
| St. epi | | serp0660 | IRKAHQ | |

TABLE V

Heparin Binding Motifs in various yeast species

| HEPARIN-BINDING MOTIF C. albicans XXXXXXX | | | | | | | | |
|---|---|---|---|---|---|---|---|---|
| Motif | Protein | C. albicans | C. dubliniensis | C. parapsilosis | C. tropicalis | C. glabrata | Lodderomyces elongisporus | A. nidulans |
| FKKRFFKL | Int1 | ✓ | YKKRFFKL | no | FKRRFFKL | FKKRFFTL | FKKFIFKL | ✓ |
| LRRLRT | Ssa2/Ssb1 | ✓ | | | | | no | |
| AKKGKF | Eno1 | ✓ | ✓ | no | no | no | no | |
| GHKIKV | Tdh3 | ✓ | ✓ | ✓ | ✓ | | ✓ | |
| ✓ | identical | | | | | | | |

The interaction of C. albicans with heparin or heparin-like compounds may play a key role in clinical settings where heparin is used (e.g. central venous catheters, dialysis catheters) or possibly in tissues where heparan sulfates are preferentially expressed.

Because antibodies raised against a linear heparin binding motif inhibited binding of C. albicans to heparin, the heparin binding peptide HKQEKQKKHQIHKV (SEQ ID NO: 4) could be used as an immunizing antigen in immunocompetent patients to elicit antibodies that protect against heparin binding.

For example, a peptide from streptococcal M protein has been used to make a vaccine for rheumatic fever (62). Alternatively, antibodies raised against this peptide in immunized humans can be used for passive immunization. This technology is used with commercially available antibodies such as hepatitis B immune globulin (HBIG) or botulism immune globulin (BabyBIG®) (63). Hepatitis B immune globulin is commercially available; botulism immune globulin is made and distributed by the California Department of Public Health and is FDA-approved. A humanized monoclonal antibody recognizing a desired heparin binding motif could be made using technology for the production of palivizumab (Synagis®), a humanized monoclonal antibody that is given monthly to premature newborns to prevent infection with respiratory syncytial virus (64). Because similar heparin binding motifs are also found in S. epidermidis and S. aureus, using heparin binding motifs as antigens is a first step in developing vaccines against three of the most common causes of central line-associated bloodstream infection.

Antibodies raised against a linear heparin binding motif expressed by a surface protein of C. albicans inhibited adhesion of the yeast to heparin in vitro and abolished biofilm formation in vivo. Similar heparin binding motifs occur in surface proteins from S. epidermidis and S. aureus, two organisms which are also major causes of biofilm-related infections.

In one embodiment, an antibody reactive with a heparin binding motif expressed on the surface of a microorganism is administered to an individual. The microorganism may be, but is not limited to, a Candida species or a Staphylococcus species. In one embodiment, the microorganism is C. albicans, S. epidermidis and/or S. aureus. In one embodiment, the heparin binding motif is identified by a computer-based algorithm analysis of protein sequences expressed by a microorganism. In one embodiment, the heparin binding motif to which the antibody was generated is derived from Int1. In one embodiment, the antibody is directed to the peptide HKQEKQKKHQIHKV (SEQ ID NO: 4), or a fragment of this peptide. In one embodiment, the fragment is at least seven amino acids of the peptide. In one embodiment, the surface expression of the heparin binding motif depends on the life-cycle stage of the microorganism. In one embodiment, the antibody is a polyclonal antibody. In one embodiment, the antibody is a monoclonal antibody.

In one embodiment, a peptide that corresponds to a linear heparin binding motif expressed on the surface of a microorganism, or a portion of the peptide, is provided. In one embodiment, the peptide is used to generate antibodies directed against the peptide, using methods known in the art. Alternatively, a peptide is provided combined with additional carriers or as a component of a complex, e.g., an adjuvant non-toxic to humans. Such an adjuvant could be aluminum hydroxide used in Engerix-B® (commercially available hepatitis B vaccine), and in Comvax® (commercially available vaccine for *Haemophilius influenzae* type b and hepatitis B). The peptide corresponds to a linear heparin binding motif, or a portion of the motif, of a microorganism. In one embodiment, the microorganism is a *Candida* species and/or a *Staphylococcus* species. In one embodiment, the microorganism is *C. albicans, S. epidermidis* and/or *S. aureus*. In one embodiment, the heparin binding motif is identified by a computer-based algorithm analysis of protein sequences expressed by a microorganism. In one embodiment, the heparin binding motif is derived from Int1. In one embodiment, the peptide is HKQEKQKKHQIHKV (SEQ ID NO: 4), or a fragment of SEQ ID NO: 4. In one embodiment, the peptide is a fragment of the peptide HKQEKQKKHQIHKV (SEQ ID NO: 4), where the fragment contains at least seven amino acids of the peptide. In one embodiment, the surface expression of the heparin binding motif depends on the life-cycle stage of the microorganism. In one embodiment, the peptide is used to generate an antibody using methods known in the art.

Figure 10:
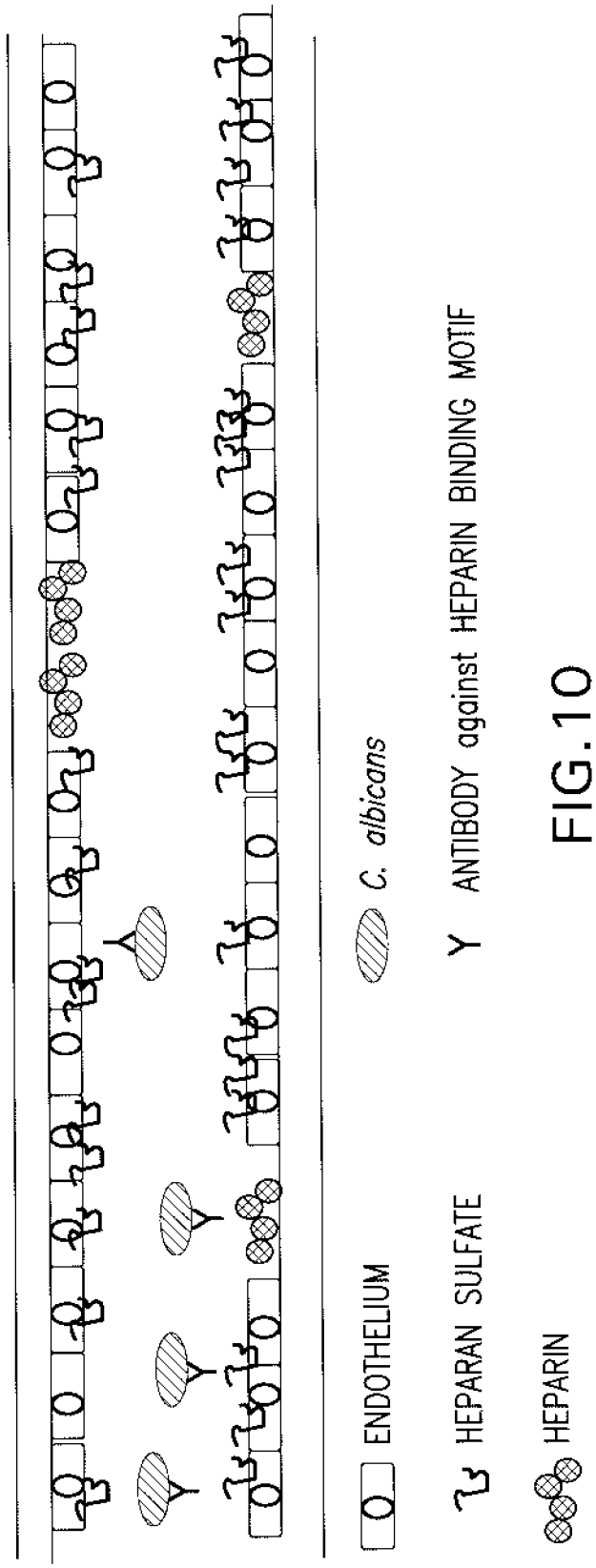
Figure 11:
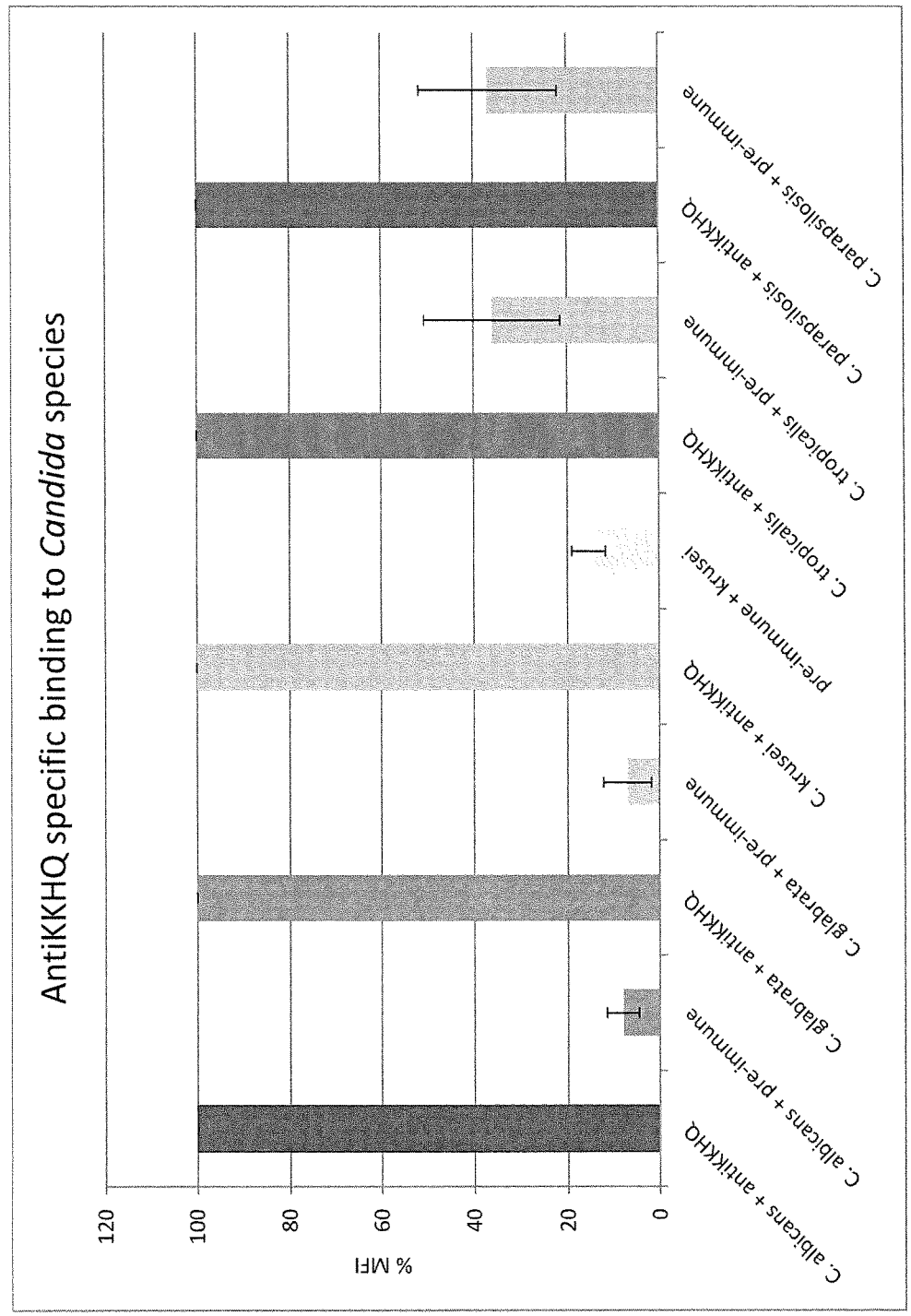
Figure 12A:
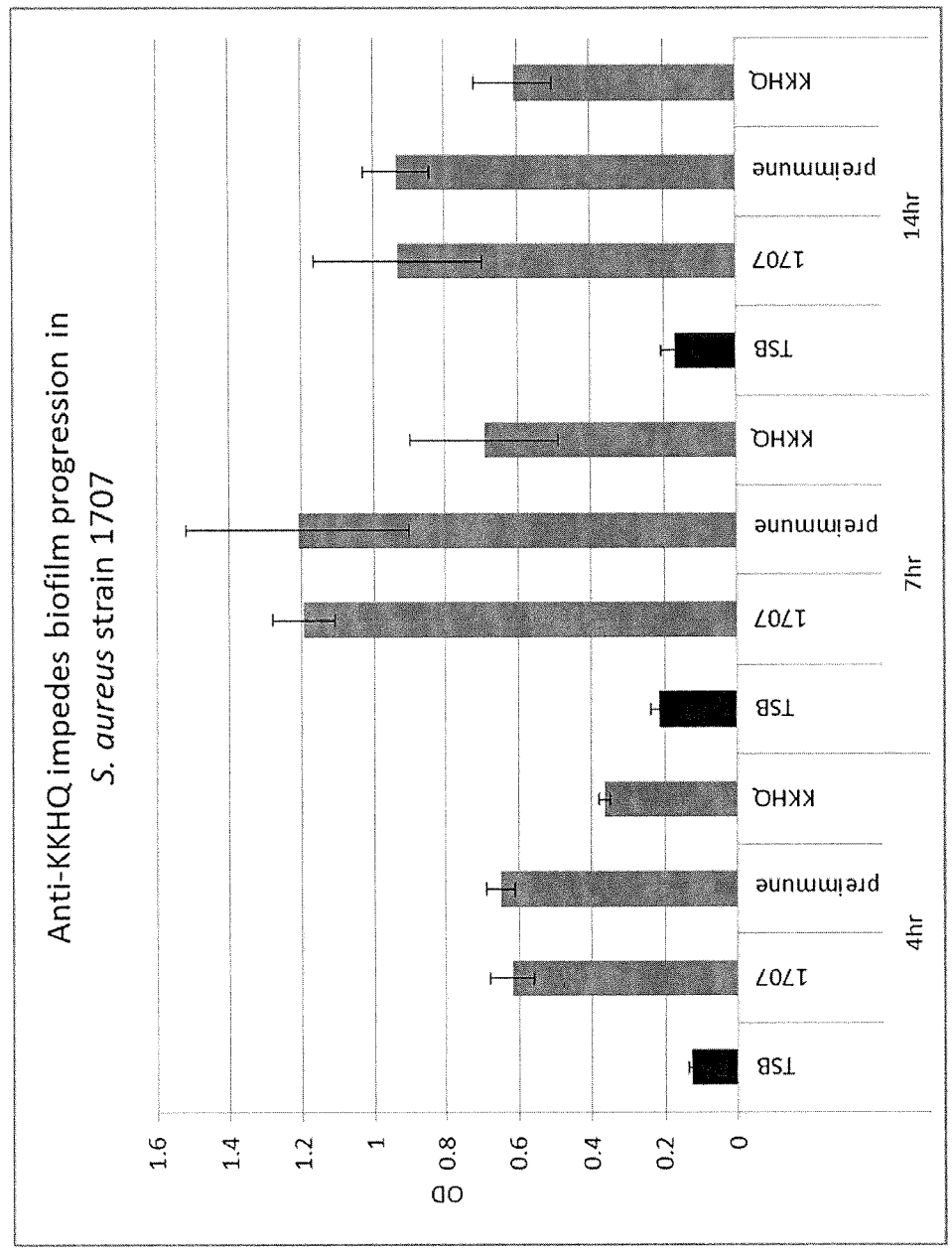
Figure 12B:
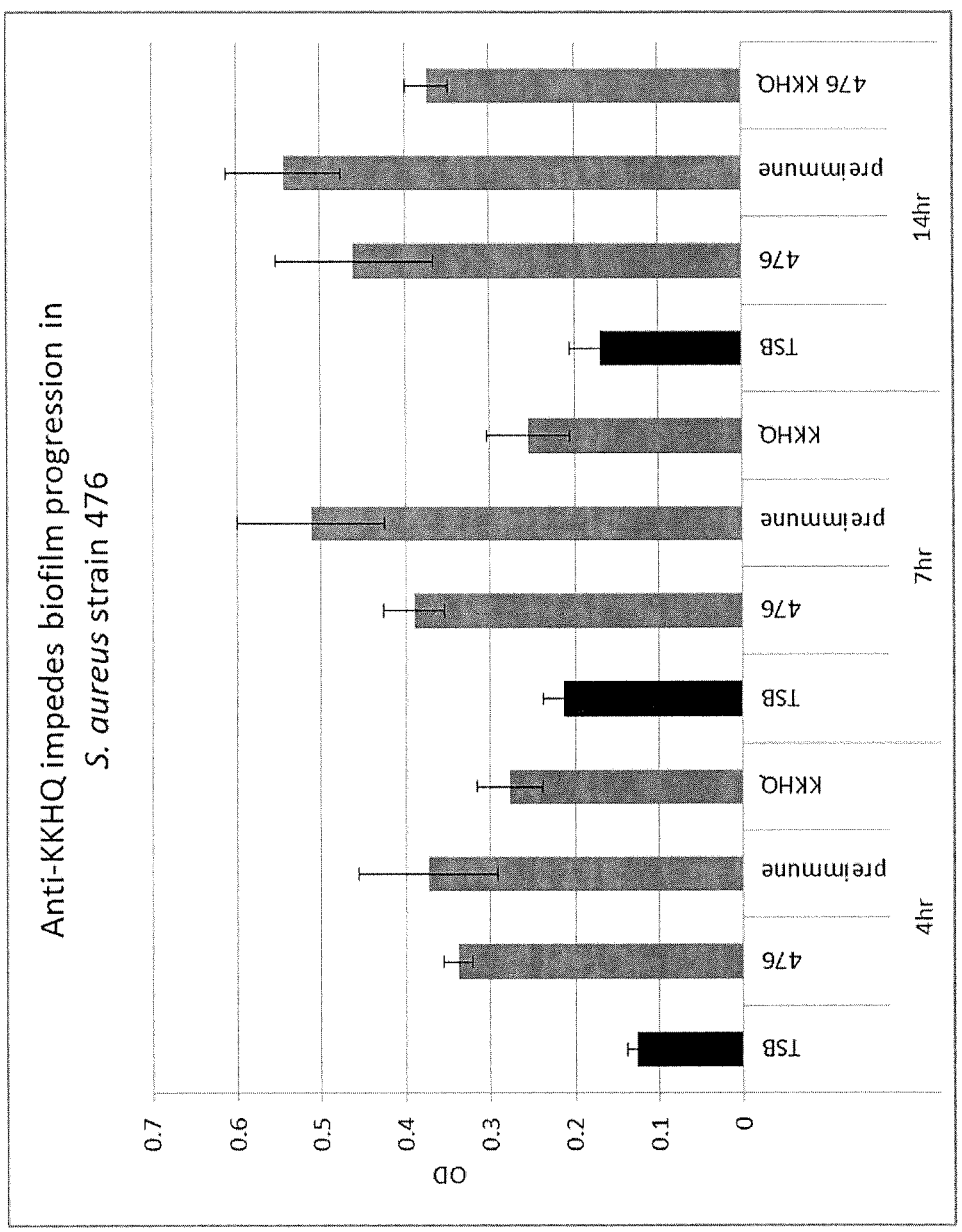
Figure 12C:
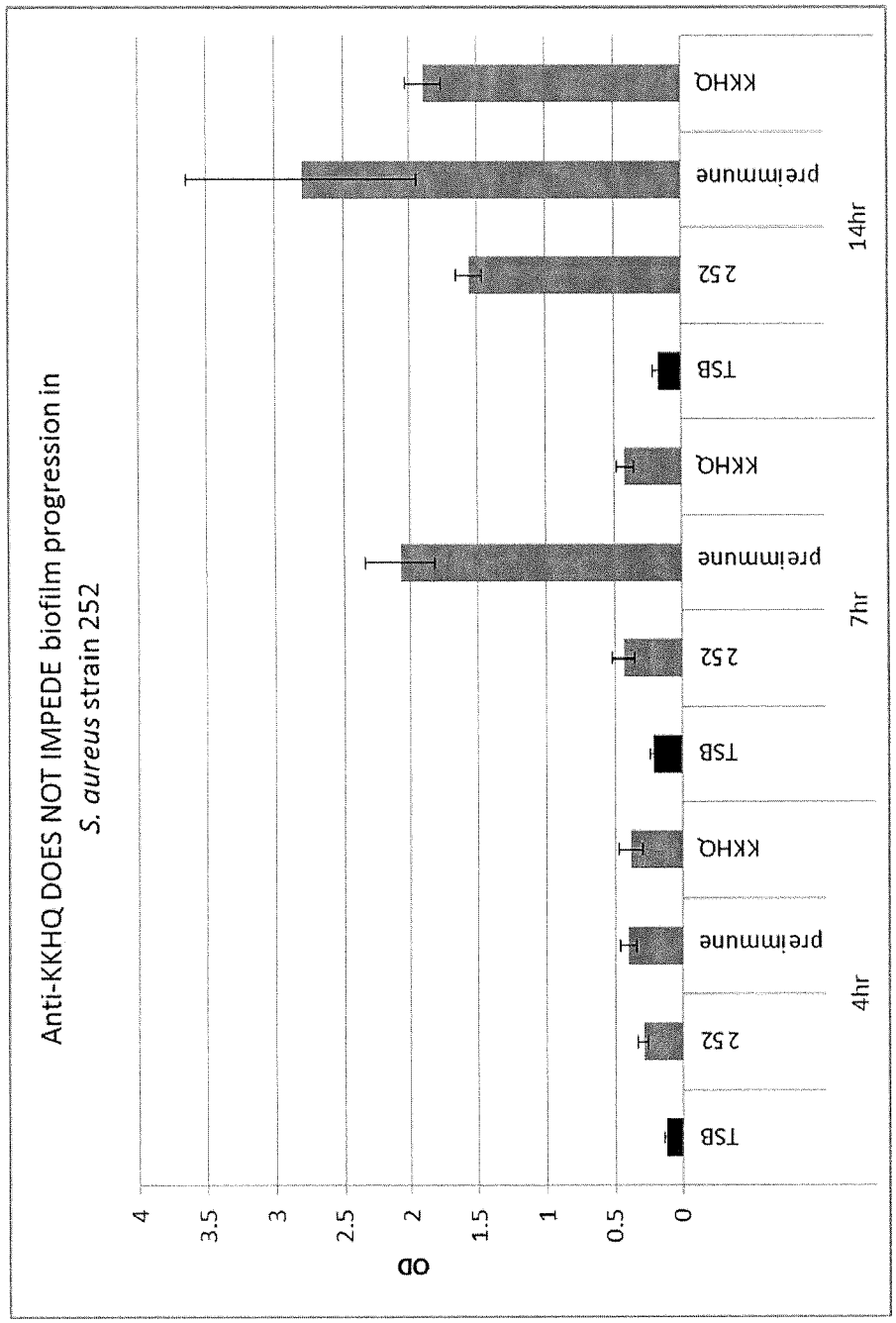

In one embodiment, a method is provided for ameliorating biofilm formation on a surface of an implanted device in a patient. In one embodiment, the method comprises administering an antibody to a patient, and ameliorating biofilm formation on a surface of an implanted device in a patient, wherein the antibody is directed to a heparin binding motif expressed on the surface of a microorganism. In one embodiment, the antibody is administered intravenously at a dose not more than 2 grams/kg given as an infusion over 10-24 hours. Since the half-life of antibody preparations is about four weeks, antibody administration would be repeated at monthly intervals over the life of the catheter. In one embodiment, the antibody has been modified to increase safety and/or efficacy in a human patient. In one embodiment, the antibody has been humanized using methods known in the art. In one embodiment, the described antibody is provided as a pharmaceutical composition with at least one biocompatible excipient, e.g., buffers, preservatives, tonicity adjusting agents, pH adjusting agents, osmolality adjusting agents, etc, as known to one skilled in the art. Without being held to a single theory, the antibody blocks binding between a heparin binding motif-containing protein expressed on the surface of a microorganism and heparin or heparin sulfate, which is expressed by human cells lining the lumen of the implanted device (FIG. 10). Binding of the antibody to the microorganism prevented its attachment to heparin or to heparin sulfate moieties. In the rat model of *Candida* infection of central venous catheters, the disclosed antibody recognizing a peptide encompassing Motif 1 in *Candida albicans* Int1 (also called anti-KKHQ antibody ("KKHQ" disclosed as SEQ ID NO: 6)) showed excellent in vivo results. The antibody recognizing Motif 1 (anti-KKHQ antibody ("KKHQ" disclosed as SEQ ID NO: 6)) substantially inhibited biofilm production, as shown in FIG. 9. FIGS. 11 and 12A-C demonstrate the anti-KKHQ antibody is effective against various *Candida* species.

The administration of the described antibody is referred to as passive immunization.

In one embodiment, the method comprises administering a peptide to a patient, where the peptide encompasses a heparin binding motif, or a fragment of the motif, that is expressed on the surface of a microorganism. The peptide is 14 amino acids in length, with amino acids both preceding and following the 8 amino acids of the heparin binding motif. In one embodiment, the peptide is HKQEKQKKHQI-HKV (SEQ ID NO: 4), or a fragment thereof. In one embodiment, the described peptide is provided as a pharmaceutical composition comprising at least one biocompatible excipient including but not limited to buffers, stabilizing agents, solubility enhancing agents, tonicity agents, etc. as known to one skilled in the art.

Without being held to a single theory, the peptide serves as an antigen to immunize the patient. It provides immunity by promoting endogenous generation of antibodies directed to the peptide, where the endogenously-produced antibodies block binding between heparin, which is administered through the catheter or is bound to a surface of an implanted medical device, and a heparin binding motif-containing protein expressed on a microorganism surface. Administration of the described peptide is referred to as active immunization. Peptide vaccines are typically administered subcutaneously or intramuscularly. Immunizing dose of the peptide and frequency of immunization are experimentally determined with humans.

The patient being treated may be naturally immunodeficient by having an underdeveloped immune response, e.g., a premature newborn. The patient being treated may have a normal immune response, but may be immunocompromised due to particular circumstances, e.g., as a result of treatment such as chemotherapy, or disease, or burns. In one embodiment, the disclosed antibody is administered to an immunodeficient patient. In one embodiment, the disclosed peptide is administered to an non-immunodeficient patient, e.g., an otherwise well adult or child who will receive long term antibiotics through a central line for the treatment of a serious infection, e.g., endocarditis.

In one embodiment, the implanted medical device, e.g., catheter, central line, hemodialysis catheter, peritoneal catheter, PICC line, plastic catheters such as central venous catheters, urinary tract catheters, central nervous system shunt catheters, peritoneal dialysis catheters, dialysis shunts, etc., is implanted in a vein, artery, or a body cavity. In one embodiment, the implanted medical device is a plastic device. In one embodiment, the implanted device is present in the patient's body for a period of time ranging from minutes to six weeks or longer. In one embodiment, the above described methods may be performed before the device is implanted in the patient. In one embodiment, a first dose of the antibody is administered before the medical device is implanted. In this embodiment, a peripheral intravenous line could administer this first dose of the antibody if the device to be implanted is a catheter.

In one embodiment, the described methods decrease the virulence of a microorganism, i.e., the method decrease the ability of a microorganism to cause infection in a patient.

All references cited are expressly incorporated by reference herein in their entirety.

1. Harrop H A, Coombe D R, Rider C C. Heparin specifically inhibits binding of V3 loop antibodies to HIV-1 gp120, an effect potentiated by CD4 binding. AIDS. 1994; 8(2):183-92.
2. Saphire A C, Bobardt M D, Gallay P A. Host cyclophilin A mediates HIV-1 attachment to target cells via heparans. The EMBO journal. 1999; 18(23):6771-85. PMCID: 1171739.
3. Rusnati M, Tulipano G, Spillmann D, Tanghetti E, Oreste P, Zoppetti G, Giacca M, Presta M. Multiple interactions of HIV-I Tat protein with size-defined heparin oligosaccharides. J Biol Chem. 1999; 274(40):28198-205.
4. Barth H, Schafer C, Adah M I, Zhang F, Linhardt R J, Toyoda H, Kinoshita-Toyoda A, Toida T, Van Kuppevelt T H, Depla E, Von Weizsacker F, Blum H E, Baumert T F. Cellular binding of hepatitis C virus envelope glycoprotein E2 requires cell surface heparan sulfate. J Biol Chem. 2003; 278(42):41003-12.
5. Williams R K, Straus S E. Specificity and affinity of binding of herpes simplex virus type 2 glycoprotein B to glycosaminoglycans. J Virol. 1997; 71(2):1375-80. PMCID: 191193.
6. Spear P G, Shieh M T, Herold B C, WuDunn D, Koshy T I. Heparan sulfate glycosaminoglycans as primary cell surface receptors for herpes simplex virus. Adv Exp Med Biol. 1992; 313:341-53.
7. Shukla D, Liu J, Blaiklock P, Shworak N W, Bai X, Esko J D, Cohen G H, Eisenberg R J, Rosenberg R D, Spear P G. A novel role for 3-O-sulfated heparan sulfate in herpes simplex virus 1 entry. Cell. 1999; 99(1):13-22.
8. Chen Y, Maguire T, Hileman R E, Fromm J R, Esko J D, Linhardt R J, Marks R M. Dengue virus infectivity depends on envelope protein binding to target cell heparan sulfate. Nat Med. 1997; 3(8):866-71.
9. Frevert U, Sinnis P, Cerami C, Shreffler W, Takacs B, Nussenzweig V. Malaria circumsporozoite protein binds to heparan sulfate proteoglycans associated with the surface membrane of hepatocytes. The Journal of experimental medicine. 1993; 177(5):1287-98. PMCID: 2190997.
10. Alvarez-Dominguez C, Vazquez-Boland J A, Carrasco-Marin E, Lopez-Mato P, Leyva-Cobian F. Host cell heparan sulfate proteoglycans mediate attachment and entry of *Listeria monocytogenes*, and the listerial surface protein ActA is involved in heparan sulfate receptor recognition. Infect Immun. 1997; 65(1):78-88. PMCID: 174559.
11. Duncan C, Prashar A, So J, Tang P, Low D E, Terebiznik M, Guyard C. Lcl of *Legionella pneumophila* is an immunogenic GAG binding adhesin that promotes interactions with lung epithelial cells and plays a crucial role in biofilm formation. Infect Immun. 2011; 79(6):2168-81. PMCID: 3125840.
12. Cardin A D, Weintraub H J. Molecular modeling of protein-glycosaminoglycan interactions. Arteriosclerosis. 1989; 9(1):21-32.
13. Sobel M, Soler D F, Kermode J C, Harris R B. Localization and characterization of a heparin binding domain peptide of human von Willebrand factor. J Biol Chem. 1992; 267(13):8857-62.
14. Capila I, Linhardt R J. Heparin-protein interactions. Angew Chem Int Ed Engl. 2002; 41(3):391-412.
15. Farshi P, Ohlig S, Pickhinke U, Hoing S, Jochmann K, Lawrence R, Dreier R, Dierker T, Grobe K. Dual roles of the Cardin-Weintraub motif in multimeric Sonic hedgehog. J Biol Chem. 2011; 286(26):23608-19. PMCID: 3123124.
16. Margalit H, Fischer N, Ben-Sasson S A. Comparative analysis of structurally defined heparin binding sequences reveals a distinct spatial distribution of basic residues. J Biol Chem. 1993; 268(26):19228-31.
17. Torrent M, Nogues M V, Andreu D, Boix E. The "CPC clip motif": a conserved structural signature for heparin-binding proteins. PLoS One. 2012; 7(8):e42692. PMCID: 3412806.
18. Finkel J S, Mitchell A P. Genetic control of *Candida albicans* biofilm development. Nat Rev Microbiol. 2011; 9(2):109-18.
19. Nobile C J, Mitchell A P. Genetics and genomics of *Candida albicans* biofilm formation. Cell Microbiol. 2006; 8(9):1382-91.
20. Hamilton R A, Plis J M, Clay C, Sylvan L. Heparin sodium versus 0.9% sodium chloride injection for maintaining patency of indwelling intermittent infusion devices. Clin Pharm. 1988; 7(6):439-43.
21. Klotz S A, Smith R L. Glycosaminoglycans inhibit *Candida albicans* adherence to extracellular matrix proteins. FEMS Microbiol Lett. 1992; 78(2-3):205-8.
22. Nobile C J, Fox E P, Nett J E, Sorrells T R, Mitrovich Q M, Hernday A D, Tuch B B, Andes D R, Johnson A D. A recently evolved transcriptional network controls biofilm development in *Candida albicans*. Cell. 2012; 148 (1-2):126-38. PMCID: 3266547.
23. Vital signs: central line-associated blood stream infections—United States, 2001, 2008, and 2009. MMWR Morbidity and mortality weekly report. 2011; 60(8):243-8.
24. Mermel L A, Allon M, Bouza E, Craven D E, Flynn P, O'Grady N P, Raad, I I, Rijnders B J, Sherertz R J, Warren D K. Clinical practice guidelines for the diagnosis and management of intravascular catheter-related infection: 2009 Update by the Infectious Diseases Society of America. Clin Infect Dis. 2009; 49(1):1-45.
25. Advani S, Reich N G, Sengupta A, Gosey L, Milstone A M. Central line-associated bloodstream infection in hospitalized children with peripherally inserted central venous catheters: extending risk analyses outside the intensive care unit. Clinical Infectious Diseases. 2011; 52(9):1108-15. PMCID: 3070870.
26. Downes K J, Metlay J P, Bell L M, McGowan K L, Elliott M R, Shah S S. Polymicrobial bloodstream infections among children and adolescents with central venous catheters evaluated in ambulatory care. Clinical Infectious Diseases 2008; 46(3):387-94.
27. Beck-Sague C, Jarvis W R. Secular trends in the epidemiology of nosocomial fungal infections in the United States, 1980-1990. National Nosocomial Infections Surveillance System. J Infect Dis. 1993; 167(5):1247-51.
28. Saiman L, Ludington E, Pfaller M, Rangel-Frausto S, Wiblin R T, Dawson J, Blumberg H, Patterson J, Rinaldi M, Edwards J E, Wenzel R P, Jarvis W, Group TNEoMSS. Risk factors for candidemia in neonatal intensive care unit patients. Pediatr Infect Dis J. 2000; 19(4):319-24.
29. Almirante B, Rodriguez D, Park B J, Cuenca-Estrella M, Planes A M, Almela M, Mensa J, Sanchez F, Ayats J, Gimenez M, Saballs P, Fridkin S K, Morgan J, Rodriguez-Tudela J L, Warnock D W, Pahissa A. Epidemiology and predictors of mortality in cases of *Candida* bloodstream infection: results from population-based surveillance, Barcelona, Spain, from 2002 to 2003. J Clin Microbiol. 2005; 43(4):1829-35.
30. Kao A S, Brandt M E, Pruitt W R, Conn L A, Perkins B A, Stephens D S, Baughman W S, Reingold A L, Rothrock G A, Pfaller M A, Pinner R W, Hajjeh R A. The epidemiology of candidemia in two United States cities: results of a population-based active surveillance. Clin Infect Dis. 1999; 29(5):1164-70.
31. MacDonald L, Baker C, Chenoweth C. Risk factors for candidemia in a children's hospital. Clin Infect Dis. 1998; 26(3):642-5.
32. Morgan J, Meltzer M I, Plikaytis B D, Sofair A N, Huie-White S, Wilcox S, Harrison L H, Seaberg E C, Hajjeh R A, Teutsch S M. Excess mortality, hospital stay, and cost due to candidemia: a case-control study using data from population-based candidemia surveillance. Infect Control Hosp Epidemiol. 2005; 26(6):540-7.
33. Pappas P G, Rex J H, Lee J, Hamill R J, Larsen R A, Powderly W, Kauffman C A, Hyslop N, Mangino J E, Chapman S, Horowitz H W, Edwards J E, Dismukes W E. A prospective observational study of candidemia: epide- 33. miology, therapy, and influences on mortality in hospitalized adult and pediatric patients. Clin Infect Dis. 2003; 37(5):634-43.
34. Li D Q, Lundberg F, Ljungh A. Binding of von Willebrand factor by coagulase-negative staphylococci. J Med Microbiol. 2000; 49(3):217-25.
35. Pascu C, Ljungh A, Wadstrom T. Staphylococci bind heparin-binding host growth factors. Curr Microbiol. 1996; 32(4):201-7.
36. Paulsson M, Gouda I, Larm O, Ljungh A. Adherence of coagulase-negative staphylococci to heparin and other glycosaminoglycans immobilized on polymer surfaces. Journal of biomedical materials research. 1994; 28(3): 311-7.
37. Shanks R M, Donegan N P, Graber M L, Buckingham S E, Zegans M E, Cheung A L, O'Toole G A. Heparin stimulates *Staphylococcus aureus* biofilm formation. Infect Immun. 2005; 73(8):4596-606.
38. Chandra J, Kuhn D M, Mukherjee P K, Hoyer L L, McCormick T, Ghannoum M A. Biofilm formation by the fungal pathogen *Candida albicans*: development, architecture, and drug resistance. Journal of Bacteriology. 2001; 183(18):5385-94.
39. Carrasco M N, Bueno A, de las Cuevas C, Jimenez S, Salinas I, Sartorius A, Recio T, Generelo M, Ruiz-Ocana F. Evaluation of a triple-lumen central venous heparin-coated catheter versus a catheter coated with chlorhexidine and silver sulfadiazine in critically ill patients. Intensive Care Med. 2004; 30(4):633-8.
40. Diskin C J. Catheter-related sepsis in dialysis patients. QJM: monthly journal of the Association of Physicians. 2007; 100(10):666-7; author reply 7.
41. Chaffin W L. *Candida albicans* cell wall proteins. Microbiol Mol Biol Rev. 2008; 72(3):495-544. PMCID: 2546859.
42. Alberti-Segui C, Morales A J, Xing H, Kessler M M, Willins D A, Weinstock K G, Cottarel G, Fechtel K, Rogers B. Identification of potential cell-surface proteins in *Candida albicans* and investigation of the role of a putative cell-surface glycosidase in adhesion and virulence. Yeast. 2004; 21(4):285-302.
43. Bendtsen J D, Nielsen H, von Heijne G, Brunak S. Improved prediction of signal peptides: SignalP 3.0. J Mol Biol. 2004; 340(4):783-95.
44. Fankhauser N, Maser P. Identification of GPI anchor attachment signals by a Kohonen self-organizing map. Bioinformatics. 2005; 21(9):1846-52.
45. Pierleoni A, Martelli P L, Casadio R. PredGPI: a GPI-anchor predictor. BMC Bioinformatics. 2008; 9:392. PMCID: 2571997.
46. Mao Y, Zhang Z, Gast C, Wong B. C-terminal signals regulate targeting of glycosylphosphatidylinositol-anchored proteins to the cell wall or plasma membrane in *Candida albicans*. Eukaryot Cell. 2008; 7(11):1906-15. PMCID: 2583546.
47. Gale C A, Bendel C M, McClellan M, Hauser M, Becker J M, Berman J, Hostetter M K. Linkage of adhesion, filamentous growth, and virulence in *Candida albicans* to a single gene, INT1. Science. 1998; 279(5355):1355-8.
48. Drew S W. Liquid Culture. In: Gerhardt P, editor. Manual of Methods for General Bacteriology. Washington, D.C.: American Society for Microbiology; 1981.
49. Osmond R I, Kett W C, Skett S E, Coombe D R. Protein-heparin interactions measured by BIAcore 2000 are affected by the method of heparin immobilization. Anal Biochem. 2002; 310(2):199-207.
50. Marson A, Robinson D E, Brookes P N, Mulloy B, Wiles M, Clark S J, Fielder H L, Collinson L J, Cain S A, Kielty C M, McArthur S, Buttle D J, Short R D, Whittle J D, Day A J. Development of a microtiter plate-based glycosaminoglycan array for the investigation of glycosaminoglycan-protein interactions. Glycobiology. 2009; 19(12):1537-46.
51. Wilson R B, Davis D, Mitchell A P. Rapid hypothesis testing with *Candida albicans* through gene disruption with short homology regions. Journal of Bacteriology. 1999; 181(6):1868-74.
52. Hoffman C S, Winston F. A ten-minute DNA preparation from yeast efficiently releases autonomous plasmids for transformation of *Escherichia coli*. Gene. 1987; 57(2-3): 267-72.
53. Sambrook J, Fritsch E, Maniatis T. Molecular Cloning: A Laboratory Manual. 2nd ed. New York: Cold Spring Harbor Laboratory Press; 1989.
54. Devore-Carter D, Kar S, Vellucci V, Bhattacherjee V, Domanski P, Hostetter M K. Superantigen-like effects of a *Candida albicans* polypeptide. J Infect Dis. 2008; 197(7):981-9.
55. Cormack B. Directed mutagenesis using the polymerase chain reaction. Curr Protoc Mol Biol 2001.
56. Xiao K, Shenoy S K, Nobles K, Lefkowitz R J. Activation-dependent conformational changes in {beta}-arrestin 2. J Biol Chem. 2004; 279(53):55744-53.
57. Lortat-Jacob H, Grimaud J A. Interferon-gamma C-terminal function: new working hypothesis. Heparan sulfate and heparin, new targets for IFN-gamma, protect, relax the cytokine and regulate its activity. Cellular and molecular biology. 1991; 37(3):253-60.
58. Villeponteau B. Heparin increases chromatin accessibility by binding the trypsin-sensitive basic residues in histones. Biochem J. 1992; 288 (Pt 3):953-8. PMCID: 1131979.
59. Eismann T, Huber N, Shin T, Kuboki S, Galloway E, Wyder M, Edwards M J, Greis K D, Shertzer H G, Fisher A B, Lentsch A B. Peroxiredoxin-6 protects against mitochondrial dysfunction and liver injury during ischemia-reperfusion in mice. Am J Physiol Gastrointest Liver Physiol. 2009; 296(2):G266-74. PMCID: 2643922.
60. Pfaffl M W. A new mathematical model for relative quantification in real-time RT-PCR. Nucleic Acids Res. 2001; 29:e45.
61. Andes D, Nett J, Oschel P, Albrecht R, Marchillo K, Pitula A. Development and characterization of an in vivo central venous catheter *Candida albicans* biofilm model. Infect Immun. 2004; 72(10):6023-31. PMCID: 517581.
62. Guerino M T, Postol E, Demarchi L M, Martins C O, Mundel L R, Kalil J, L. G. HLA class II transgenic mice develop a safe and long lasting immune response against StreptInCor, an anti-group A *streptococcus* vaccine candidate. Vaccine. 2011; 29(46):8250-6.
63. 2012 Report of the Committee on Infectious Diseases. Elk Grove Village, Ill.: American Academy of Pediatrics.
64. Schenerman M A, Hope J N, Kletke C, Singh J K, Kimura R, Tsao E I, Folena-Wasserman G. Comparability testing of a humanized monoclonal antibody (Synagis) to support cell line stability, process validation, and scale-up for manufacturing. Biologicals. 1999; 27(3):203-15.

The instant application contains a Sequence Listing which has been submitted in ASCII format via EFS-Web and is hereby incorporated by reference in its entirety. The ASCII copy, created on Mar. 8, 2013, is named 070248_94_SL.txt and is 30,824 bytes in size.

The embodiments described in the specification are only specific embodiments of the inventors who are skilled in the art and are not limiting. Therefore, various changes, modifications, or alterations to those embodiments may be made without departing from the spirit of the invention or the scope of the following claims.

What is claimed is:

1. A method to reduce or inhibit biofilm formation on a surface of an indwelling or implanted medical device in a patient, the method comprising administering before, during, and/or after installation or implantation of the medical device in the patient an effective amount of a composition, the composition comprising
   at least one biocompatible excipient and an antibody that binds isolated peptide HKQEKQKKHQIHKV (SEQ ID NO: 4) or that binds a fragment of at least seven contiguous amino acids of SEQ ID NO: 4; or the composition comprising
   at least one biocompatible excipient and isolated peptide HKQEKQKKHQIHKV (SEQ ID NO: 4) or a fragment of at least seven contiguous amino acids of SEQ ID NO: 4,
the administering occurring under conditions to result in reduced heparin-binding to a surface of the implanted medical device, resulting in reduced or inhibited biofilm formation on the medical device.

2. The method of claim 1 where, when the composition comprises the peptide, the peptide antigenically immunizes the patient by endogenously generating anti-peptide antibodies that reduce or inhibit biofilm formation on the surface of the indwelling or implanted device by reducing or inhibiting microorganism heparin-mediated-binding to the device surface.

3. The method of claim 1 where the medical device is selected from the group consisting of a venous catheter, an arterial catheter, a central line, a hemodialysis catheter, a peritoneal catheter, a peripherally inserted central catheter, a urinary tract catheter, a central nervous system shunt, a peritoneal dialysis catheter, a dialysis shunt, and combinations thereof.

4. The method of claim 1 resulting in decreased infection in the patient.

5. The method of claim 1 resulting in decreased microorganism virulence.

6. The method of claim 1 where the composition administered is at least one biocompatible excipient and an antibody that binds isolated peptide HKQEKQKKHQIHKV (SEQ ID NO: 4) or that binds a fragment of at least seven contiguous amino acids of SEQ ID NO: 4.

* * * * *

```
                            SEQUENCE LISTING

<160> NUMBER OF SEQ ID NOS: 95

<210> SEQ ID NO 1
<211> LENGTH: 8
<212> TYPE: PRT
<213> ORGANISM: Candida albicans

<400> SEQUENCE: 1

Gln Lys Lys His Gln Ile His Lys
1               5

<210> SEQ ID NO 2
<211> LENGTH: 8
<212> TYPE: PRT
<213> ORGANISM: Candida albicans

<400> SEQUENCE: 2

Phe Lys Lys Arg Phe Phe Lys Leu
1               5

<210> SEQ ID NO 3
<211> LENGTH: 6
<212> TYPE: PRT
<213> ORGANISM: Candida albicans

<400> SEQUENCE: 3

Ser His Lys Thr Arg Ala
1               5

<210> SEQ ID NO 4
<211> LENGTH: 14
<212> TYPE: PRT
<213> ORGANISM: Candida albicans

<400> SEQUENCE: 4

His Lys Gln Glu Lys Gln Lys Lys His Gln Ile His Lys Val
1               5                   10

<210> SEQ ID NO 5
<211> LENGTH: 1711
<212> TYPE: PRT
<213> ORGANISM: Candida albicans

<400> SEQUENCE: 5

Met Gln Thr Ser Ile Ser Thr Thr Thr Ile Glu Asp His Leu His His
1               5                   10                  15

Tyr Ser Pro Glu Glu Ser Gln Lys Leu Leu Ser Arg Glu Ser Ser Ile
            20                  25                  30

Asn Thr Asp Leu Phe Lys His Glu Asn Glu Ser Val Asp Leu Leu Leu
        35                  40                  45

Lys Glu Met Asn Ser Thr Pro Ser Lys Leu Leu Pro Ile Asp Lys His
    50                  55                  60

Ser His Leu Gln Leu Gln Pro Gln Ser Ser Ala Ser Ile Phe Asn
65                  70                  75                  80

Ser Pro Thr Lys Pro Leu Asn Phe Pro Arg Thr Asn Ser Lys Pro Ser
                85                  90                  95

Leu Asp Pro Asn Ser Ser Ser Asp Thr Tyr Thr Ser Glu Gln Asp Gln
            100                 105                 110
```

-continued

```
Glu Lys Gly Lys Glu Lys Lys Asp Thr Thr Phe Gln Thr Ser Phe
            115                 120                 125

Asp Arg Asn Phe Asp Leu Asp Asn Ser Ile Asp Ile Gln Gln Thr Ile
        130                 135                 140

Gln His Gln Gln Gln Pro Gln Gln Gln Gln Leu Ser Gln Thr
145                 150                 155                 160

Asp Asn Asn Leu Ile Asp Glu Phe Ser Phe Gln Thr Pro Met Thr Ser
                165                 170                 175

Thr Leu Asp Leu Thr Lys Gln Asn Pro Thr Val Asp Lys Val Asn Glu
            180                 185                 190

Asn His Ala Pro Thr Tyr Ile Asn Thr Ser Pro Asn Lys Ser Ile Met
        195                 200                 205

Lys Lys Ala Thr Pro Lys Val Ser Pro Lys Lys Val Ala Phe Thr Ala
210                 215                 220

Thr Asn Pro Glu Ile His His Tyr Pro Asp Asn Arg Val Glu Glu Glu
225                 230                 235                 240

Asp Gln Ser Gln Gln Lys Glu Asp Ser Val Glu Pro Pro Ser Ile Gln
                245                 250                 255

His Gln Trp Lys Asp Pro Ser Gln Phe Asn Tyr Ser Glu Asp Thr
            260                 265                 270

Asn Ala Ser Val Pro Pro Thr Pro Pro Leu His Thr Thr Lys Pro Thr
        275                 280                 285

Phe Ala Gln Leu Leu Asn Lys Asn Asn Glu Val Asn Ser Glu Pro Glu
290                 295                 300

Ala Leu Thr Asp Met Lys Leu Lys His Glu Asn Phe Ser Asn Leu Ser
305                 310                 315                 320

Leu Asp Glu Lys Val Asn Leu Tyr Leu Ser Pro Thr Asn Asn Asn Asn
                325                 330                 335

Ser Lys Asn Val Ser Asp Met Asp Ser His Leu Gln Asn Leu Gln Asp
            340                 345                 350

Ala Ser Lys Asn Lys Thr Asn Glu Asn Ile His Asn Leu Ser Phe Ala
        355                 360                 365

Leu Lys Ala Pro Lys Asn Asp Ile Glu Asn Pro Leu Asn Ser Leu Thr
370                 375                 380

Asn Ala Asp Ile Ser Leu Arg Ser Ser Gly Ser Ser Gln Ser Ser Leu
385                 390                 395                 400

Gln Ser Leu Arg Asp Asp Asn Arg Val Leu Glu Ser Thr Pro Gly Ser
                405                 410                 415

Pro Lys Lys Val Asn Pro Gly Leu Ser Leu Asn Asp Gly Ile Lys Gly
            420                 425                 430

Phe Ser Asp Glu Val Val Glu Ser Leu Leu Pro Arg Asp Leu Ser Arg
        435                 440                 445

Asp Lys Leu Glu Thr Thr Lys Glu Asn Asp Ala Pro Glu His Asn Asn
450                 455                 460

Glu Asn Phe Ile Asp Ala Lys Ser Thr Asn Thr Lys Gly Gln Leu
465                 470                 475                 480

Leu Val Ser Ser Asp Asp His Leu Asp Ser Phe Asp Arg Ser Tyr Asn
                485                 490                 495

His Thr Glu Gln Ser Ile Leu Asn Leu Leu Asn Ser Ala Ser Gln Ser
            500                 505                 510

Gln Ile Ser Leu Asn Ala Leu Glu Lys Gln Lys Gln Ile Gln Glu Gln
        515                 520                 525
```

-continued

Glu Gln Thr Gln Ala Ala Glu Pro Glu Glu Thr Ser Phe Ser Asp
    530                 535                 540

Asn Ile Lys Val Lys Gln Glu Pro Lys Ser Asn Leu Glu Phe Val Lys
545                 550                 555                 560

Val Thr Ile Lys Lys Glu Pro Val Ser Ala Thr Glu Ile Lys Ala Pro
                565                 570                 575

Lys Arg Glu Phe Ser Ser Arg Ile Leu Arg Ile Lys Asn Glu Asp Glu
            580                 585                 590

Ile Ala Glu Pro Ala Asp Ile His Pro Lys Lys Glu Glu Ala Asn
        595                 600                 605

Ser His Val Glu Asp Thr Asp Ala Leu Leu Lys Lys Ala Leu Asn Asp
    610                 615                 620

Asp Glu Glu Ser Asp Thr Thr Gln Asn Ser Thr Lys Met Ser Ile Arg
625                 630                 635                 640

Phe His Ile Asp Ser Asp Trp Lys Leu Glu Asp Ser Asn Asp Gly Asp
                645                 650                 655

Arg Glu Asp Asn Asp Asp Ile Ser Arg Phe Glu Lys Ser Asp Ile Leu
            660                 665                 670

Asn Asp Val Ser Gln Thr Ser Asp Ile Ile Gly Asp Lys Tyr Gly Asn
        675                 680                 685

Ser Ser Ser Glu Ile Thr Thr Lys Thr Leu Ala Pro Pro Arg Ser Asp
    690                 695                 700

Asn Asn Asp Lys Glu Asn Ser Lys Ser Phe Glu Asp Pro Ala Asn Asn
705                 710                 715                 720

Glu Ser Ser Gln Gln Gln Leu Glu Val Pro His Thr Lys Glu Asp Asp
                725                 730                 735

Ser Ile Leu Ala Asn Ser Ser Asn Ile Ala Pro Pro Glu Glu Leu Thr
            740                 745                 750

Leu Pro Val Val Glu Ala Asn Asp Tyr Ser Ser Phe Asn Asp Val Thr
        755                 760                 765

Lys Thr Phe Asp Ala Tyr Ser Ser Phe Glu Glu Ser Leu Ser Arg Glu
    770                 775                 780

His Glu Thr Asp Ser Lys Pro Ile Asn Phe Ile Ser Ile Trp His Lys
785                 790                 795                 800

Gln Glu Lys Gln Lys Lys His Gln Ile His Lys Val Pro Thr Lys Gln
                805                 810                 815

Ile Ile Ala Ser Tyr Gln Gln Tyr Lys Asn Glu Gln Glu Ser Arg Val
            820                 825                 830

Thr Ser Asp Lys Val Lys Ile Pro Asn Ala Ile Gln Ser Lys Lys Phe
        835                 840                 845

Lys Glu Val Asn Val Met Ser Arg Arg Val Val Ser Pro Asp Met Asp
    850                 855                 860

Asp Leu Asn Val Ser Gln Phe Leu Pro Glu Leu Ser Glu Asp Ser Gly
865                 870                 875                 880

Phe Lys Asp Leu Asn Phe Ala Asn Tyr Ser Asn Asn Thr Asn Arg Pro
                885                 890                 895

Arg Ser Phe Thr Pro Leu Ser Thr Lys Asn Val Leu Ser Asn Ile Asp
            900                 905                 910

Asn Asp Pro Asn Val Val Glu Pro Glu Pro Lys Ser Tyr Ala Glu
        915                 920                 925

Ile Arg Asn Ala Arg Arg Leu Ser Ala Asn Lys Ala Ala Pro Asn Gln
    930                 935                 940

Ala Pro Pro Leu Pro Pro Gln Arg Gln Pro Ser Ser Thr Arg Ser Asn

```
                    945                 950                 955                 960
           Ser Asn Lys Arg Val Ser Arg Phe Arg Val Pro Thr Phe Glu Ile Arg
                            965                 970                 975
           Arg Thr Ser Ser Ala Leu Ala Pro Cys Asp Met Tyr Asn Asp Ile Phe
                            980                 985                 990
           Asp Asp Phe Gly Ala Gly Ser Lys Pro Thr Ile Lys Ala Glu Gly Met
                        995                 1000                1005
           Lys Thr Leu Pro Ser Met Asp Lys Asp Val Lys Arg Ile Leu
                   1010                1015                1020
           Asn Ala Lys Lys Gly Val Thr Gln Asp Glu Tyr Ile Asn Ala Lys
                   1025                1030                1035
           Leu Val Asp Gln Lys Pro Lys Lys Asn Ser Ile Val Thr Asp Pro
                   1040                1045                1050
           Glu Asp Arg Tyr Glu Glu Leu Gln Gln Thr Ala Ser Ile His Asn
                   1055                1060                1065
           Ala Thr Ile Asp Ser Ser Ile Tyr Gly Arg Pro Asp Ser Ile Ser
                   1070                1075                1080
           Thr Asp Met Leu Pro Tyr Leu Ser Asp Glu Leu Lys Lys Pro Pro
                   1085                1090                1095
           Thr Ala Leu Leu Ser Ala Asp Arg Leu Phe Met Glu Gln Glu Val
                   1100                1105                1110
           Arg His Pro Leu Arg Ser Asn Ser Val Leu Val His Pro Gly Ala
                   1115                1120                1125
           Gly Ala Ala Thr Asn Ser Ser Met Leu Pro Glu Pro Asp Phe Glu
                   1130                1135                1140
           Leu Ile Asn Ser Pro Ala Arg Asn Val Ser Asn Asn Ser Asp Asn
                   1145                1150                1155
           Val Ala Ile Ser Gly Asn Ala Ser Thr Ile Ser Phe Asn Pro Leu
                   1160                1165                1170
           Asp Met Asn Phe Asp Asp Gln Ala Thr Ile Gly Gln Asn Ile Gln
                   1175                1180                1185
           Glu Gln Pro Ala Ser Lys Ser Ala Asn Thr Val Arg Gly Asp Asp
                   1190                1195                1200
           Asp Gly Leu Ala Ser Ala Pro Glu Thr Pro Arg Thr Pro Thr Lys
                   1205                1210                1215
           Lys Glu Ser Ile Ser Ser Lys Pro Ala Lys Leu Ser Ser Ala Ser
                   1220                1225                1230
           Pro Arg Lys Ser Pro Ile Lys Ile Gly Ser Pro Val Arg Val Ile
                   1235                1240                1245
           Lys Lys Asn Gly Ser Ile Ala Gly Ile Glu Pro Ile Pro Lys Ala
                   1250                1255                1260
           Thr His Lys Pro Lys Lys Ser Phe Gln Gly Asn Glu Ile Ser Asn
                   1265                1270                1275
           His Lys Val Arg Asp Gly Gly Ile Ser Pro Ser Ser Gly Ser Glu
                   1280                1285                1290
           His Gln Gln His Asn Pro Ser Met Val Ser Val Pro Ser Gln Tyr
                   1295                1300                1305
           Thr Asp Ala Thr Ser Thr Asp Pro Asp Glu Asn Lys Asp Val Gln
                   1310                1315                1320
           His Lys Pro Arg Glu Lys Gln Lys Gln Lys His His Arg His
                   1325                1330                1335
           His His His Lys Gln Lys Thr Asp Ile Pro Gly Val Val Asp Asp
                   1340                1345                1350
```

```
Glu Ile Pro Asp Val Gly Ser Gln Glu Arg Gly Lys Leu Phe Phe
    1355                1360                1365

Arg Val Leu Gly Ile Lys Asn Ile Asn Leu Pro Asp Ile Asn Thr
    1370                1375                1380

His Lys Gly Arg Phe Thr Leu Thr Leu Asp Asn Gly Val His Cys
    1385                1390                1395

Val Thr Thr Pro Glu Tyr Asn Met Asp Asp His Asn Val Ala Ile
    1400                1405                1410

Gly Lys Glu Phe Glu Leu Thr Val Ala Asp Ser Leu Glu Phe Ile
    1415                1420                1425

Leu Thr Leu Lys Ala Ser Tyr Glu Lys Pro Arg Gly Thr Leu Val
    1430                1435                1440

Glu Val Thr Glu Lys Lys Val Val Lys Ser Arg Asn Arg Leu Ser
    1445                1450                1455

Arg Leu Phe Gly Leu Lys Asp Ile Ile Thr Thr Thr Lys Phe Val
    1460                1465                1470

Pro Thr Glu Val Lys Asp Thr Trp Ala Asn Lys Phe Ala Pro Asp
    1475                1480                1485

Gly Ser Phe Ala Arg Cys Tyr Ile Asp Leu Gln Gln Phe Glu Asp
    1490                1495                1500

Gln Ile Thr Gly Lys Ala Ser Gln Phe Asp Leu Asn Cys Phe Asn
    1505                1510                1515

Glu Trp Glu Thr Met Ser Asn Gly Asn Gln Pro Met Lys Arg Gly
    1520                1525                1530

Lys Pro Tyr Lys Ile Ala Gln Leu Glu Val Lys Met Leu Tyr Val
    1535                1540                1545

Pro Arg Ser Asp Pro Arg Glu Ile Leu Pro Thr Ser Ile Arg Ser
    1550                1555                1560

Ala Tyr Glu Ser Ile Asn Glu Leu Asn Asn Glu Gln Asn Asn Tyr
    1565                1570                1575

Phe Glu Gly Tyr Leu His Gln Glu Gly Gly Asp Cys Pro Ile Phe
    1580                1585                1590

Lys Lys Arg Phe Phe Lys Leu Met Gly Thr Ser Leu Leu Ala His
    1595                1600                1605

Ser Glu Ile Ser His Lys Thr Arg Ala Lys Ile Asn Leu Ser Lys
    1610                1615                1620

Val Val Asp Leu Ile Tyr Val Asp Lys Glu Asn Ile Asp Arg Ser
    1625                1630                1635

Asn His Arg Asn Phe Ser Asp Val Leu Leu Leu Asp His Ala Phe
    1640                1645                1650

Lys Ile Lys Phe Ala Asn Gly Glu Leu Ile Asp Phe Cys Ala Pro
    1655                1660                1665

Asn Lys His Glu Met Lys Ile Trp Ile Gln Asn Leu Gln Glu Ile
    1670                1675                1680

Ile Tyr Arg Asn Arg Phe Arg Arg Gln Pro Trp Val Asn Leu Met
    1685                1690                1695

Leu Gln Gln Gln Gln Gln Gln Gln Ser Ser Gln Gln
    1700                1705                1710

<210> SEQ ID NO 6
<211> LENGTH: 4
<212> TYPE: PRT
<213> ORGANISM: Candida albicans
```

```
<400> SEQUENCE: 6

Lys Lys His Gln
1

<210> SEQ ID NO 7
<211> LENGTH: 6
<212> TYPE: PRT
<213> ORGANISM: Candida albicans

<400> SEQUENCE: 7

Ser His Arg Ile Arg Val
1               5

<210> SEQ ID NO 8
<211> LENGTH: 6
<212> TYPE: PRT
<213> ORGANISM: Candida albicans

<400> SEQUENCE: 8

Asn Lys Lys Gly Lys Ser
1               5

<210> SEQ ID NO 9
<211> LENGTH: 6
<212> TYPE: PRT
<213> ORGANISM: Candida albicans

<400> SEQUENCE: 9

Gly Lys Lys Val Lys Ala
1               5

<210> SEQ ID NO 10
<211> LENGTH: 8
<212> TYPE: PRT
<213> ORGANISM: Candida albicans

<400> SEQUENCE: 10

Gln Arg Lys Arg Ala Leu Lys Ala
1               5

<210> SEQ ID NO 11
<211> LENGTH: 6
<212> TYPE: PRT
<213> ORGANISM: Candida albicans

<400> SEQUENCE: 11

Gln Lys Arg Ser Arg Phe
1               5

<210> SEQ ID NO 12
<211> LENGTH: 6
<212> TYPE: PRT
<213> ORGANISM: Candida albicans

<400> SEQUENCE: 12

Asn Lys Lys Phe Lys Asn
1               5

<210> SEQ ID NO 13
<211> LENGTH: 6
<212> TYPE: PRT
<213> ORGANISM: Candida albicans

<400> SEQUENCE: 13
```

Val Lys Arg Ala Arg Tyr
1               5

<210> SEQ ID NO 14
<211> LENGTH: 6
<212> TYPE: PRT
<213> ORGANISM: Candida albicans

<400> SEQUENCE: 14

Leu Arg Arg Leu Arg Thr
1               5

<210> SEQ ID NO 15
<211> LENGTH: 6
<212> TYPE: PRT
<213> ORGANISM: Candida albicans

<400> SEQUENCE: 15

Ile Lys Lys Asn His Leu
1               5

<210> SEQ ID NO 16
<211> LENGTH: 6
<212> TYPE: PRT
<213> ORGANISM: Candida albicans

<400> SEQUENCE: 16

Gly Lys Lys Val Lys Gln
1               5

<210> SEQ ID NO 17
<211> LENGTH: 6
<212> TYPE: PRT
<213> ORGANISM: Candida albicans

<400> SEQUENCE: 17

Leu Lys Arg Ile His Asn
1               5

<210> SEQ ID NO 18
<211> LENGTH: 6
<212> TYPE: PRT
<213> ORGANISM: Candida albicans

<400> SEQUENCE: 18

Ile Arg Arg Gly Arg Tyr
1               5

<210> SEQ ID NO 19
<211> LENGTH: 6
<212> TYPE: PRT
<213> ORGANISM: Candida albicans

<400> SEQUENCE: 19

Thr Lys Lys Gly Lys Leu
1               5

<210> SEQ ID NO 20
<211> LENGTH: 8
<212> TYPE: PRT
<213> ORGANISM: Candida albicans

<400> SEQUENCE: 20

Pro His His His Leu Asn Arg Tyr
1               5

```
<210> SEQ ID NO 21
<211> LENGTH: 6
<212> TYPE: PRT
<213> ORGANISM: Candida albicans

<400> SEQUENCE: 21

Ala Lys Lys Gly Lys Phe
1               5

<210> SEQ ID NO 22
<211> LENGTH: 6
<212> TYPE: PRT
<213> ORGANISM: Candida albicans

<400> SEQUENCE: 22

Thr Lys His Ile His Asn
1               5

<210> SEQ ID NO 23
<211> LENGTH: 6
<212> TYPE: PRT
<213> ORGANISM: Candida albicans

<400> SEQUENCE: 23

Ala Lys Arg Pro Arg Pro
1               5

<210> SEQ ID NO 24
<211> LENGTH: 6
<212> TYPE: PRT
<213> ORGANISM: Candida albicans

<400> SEQUENCE: 24

Leu Arg Lys Tyr Lys Gly
1               5

<210> SEQ ID NO 25
<211> LENGTH: 6
<212> TYPE: PRT
<213> ORGANISM: Candida albicans

<400> SEQUENCE: 25

Gln Arg Lys Leu Lys Thr
1               5

<210> SEQ ID NO 26
<211> LENGTH: 6
<212> TYPE: PRT
<213> ORGANISM: Candida albicans

<400> SEQUENCE: 26

Leu Arg Arg Leu Arg Thr
1               5

<210> SEQ ID NO 27
<211> LENGTH: 6
<212> TYPE: PRT
<213> ORGANISM: Candida albicans

<400> SEQUENCE: 27

Pro Lys Arg Gln Lys Thr
1               5
```

```
<210> SEQ ID NO 28
<211> LENGTH: 6
<212> TYPE: PRT
<213> ORGANISM: Candida albicans

<400> SEQUENCE: 28

Asn Lys His Asn Arg Ile
1               5

<210> SEQ ID NO 29
<211> LENGTH: 6
<212> TYPE: PRT
<213> ORGANISM: Candida albicans

<400> SEQUENCE: 29

Phe His Lys Ala His Gly
1               5

<210> SEQ ID NO 30
<211> LENGTH: 6
<212> TYPE: PRT
<213> ORGANISM: Candida albicans

<400> SEQUENCE: 30

Pro Lys Arg Val Lys Val
1               5

<210> SEQ ID NO 31
<211> LENGTH: 6
<212> TYPE: PRT
<213> ORGANISM: Candida albicans

<400> SEQUENCE: 31

Gly Lys Lys Thr Arg Ile
1               5

<210> SEQ ID NO 32
<211> LENGTH: 6
<212> TYPE: PRT
<213> ORGANISM: Candida albicans

<400> SEQUENCE: 32

Leu Arg Arg Leu Arg Thr
1               5

<210> SEQ ID NO 33
<211> LENGTH: 6
<212> TYPE: PRT
<213> ORGANISM: Candida albicans

<400> SEQUENCE: 33

Pro Lys Lys Leu Lys Phe
1               5

<210> SEQ ID NO 34
<211> LENGTH: 6
<212> TYPE: PRT
<213> ORGANISM: Candida albicans

<400> SEQUENCE: 34

Gly His Lys Ile Lys Val
1               5

<210> SEQ ID NO 35
<211> LENGTH: 8
```

```
<212> TYPE: PRT
<213> ORGANISM: Candida albicans

<400> SEQUENCE: 35

Thr Lys His His Ile Pro Lys Ala
1               5

<210> SEQ ID NO 36
<211> LENGTH: 6
<212> TYPE: PRT
<213> ORGANISM: Candida albicans

<400> SEQUENCE: 36

Ser Lys Arg Asn Lys Asn
1               5

<210> SEQ ID NO 37
<211> LENGTH: 6
<212> TYPE: PRT
<213> ORGANISM: Candida albicans

<400> SEQUENCE: 37

Met Lys Arg Ala Lys Val
1               5

<210> SEQ ID NO 38
<211> LENGTH: 6
<212> TYPE: PRT
<213> ORGANISM: Candida albicans

<400> SEQUENCE: 38

Thr His Arg Phe Lys Phe
1               5

<210> SEQ ID NO 39
<211> LENGTH: 6
<212> TYPE: PRT
<213> ORGANISM: Candida albicans

<400> SEQUENCE: 39

Leu Arg Lys Gly Lys Ser
1               5

<210> SEQ ID NO 40
<211> LENGTH: 6
<212> TYPE: PRT
<213> ORGANISM: Candida albicans

<400> SEQUENCE: 40

Thr His Lys Gly Arg Phe
1               5

<210> SEQ ID NO 41
<211> LENGTH: 6
<212> TYPE: PRT
<213> ORGANISM: Candida albicans

<400> SEQUENCE: 41

Ile Lys Lys Phe Lys Tyr
1               5

<210> SEQ ID NO 42
<211> LENGTH: 6
<212> TYPE: PRT
<213> ORGANISM: Candida albicans
```

-continued

<400> SEQUENCE: 42

Cys His Lys Cys His Asn
1               5

<210> SEQ ID NO 43
<211> LENGTH: 6
<212> TYPE: PRT
<213> ORGANISM: Candida albicans

<400> SEQUENCE: 43

Val Lys Lys Phe Arg Gln
1               5

<210> SEQ ID NO 44
<211> LENGTH: 6
<212> TYPE: PRT
<213> ORGANISM: Candida albicans

<400> SEQUENCE: 44

Ala Lys Lys Val Lys Asn
1               5

<210> SEQ ID NO 45
<211> LENGTH: 6
<212> TYPE: PRT
<213> ORGANISM: Candida albicans

<400> SEQUENCE: 45

Val Lys Lys Leu Lys Pro
1               5

<210> SEQ ID NO 46
<211> LENGTH: 6
<212> TYPE: PRT
<213> ORGANISM: Candida albicans

<400> SEQUENCE: 46

Gly Lys Lys Tyr Arg Gly
1               5

<210> SEQ ID NO 47
<211> LENGTH: 6
<212> TYPE: PRT
<213> ORGANISM: Candida albicans

<400> SEQUENCE: 47

Ala Arg Arg Ser Lys Ser
1               5

<210> SEQ ID NO 48
<211> LENGTH: 6
<212> TYPE: PRT
<213> ORGANISM: Candida albicans

<400> SEQUENCE: 48

Met Lys Arg Gly Lys Pro
1               5

<210> SEQ ID NO 49
<211> LENGTH: 6
<212> TYPE: PRT
<213> ORGANISM: Candida albicans

<400> SEQUENCE: 49

Ile Arg His Phe Lys Gly
1               5

<210> SEQ ID NO 50
<211> LENGTH: 6
<212> TYPE: PRT
<213> ORGANISM: Candida albicans

<400> SEQUENCE: 50

Phe Lys Arg Phe Lys Phe
1               5

<210> SEQ ID NO 51
<211> LENGTH: 6
<212> TYPE: PRT
<213> ORGANISM: Candida albicans

<400> SEQUENCE: 51

Ala His Arg Ala His Ser
1               5

<210> SEQ ID NO 52
<211> LENGTH: 8
<212> TYPE: PRT
<213> ORGANISM: Candida albicans

<400> SEQUENCE: 52

Gln Ala Ala His Gln Ile His Lys
1               5

<210> SEQ ID NO 53
<211> LENGTH: 8
<212> TYPE: PRT
<213> ORGANISM: Candida albicans

<400> SEQUENCE: 53

Phe Lys Ala Ala Phe Phe Lys Leu
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 54

His His His His His His
1               5

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggagctcgt tacttgtcat taattagtta cttcc                          35

<210> SEQ ID NO 56
<211> LENGTH: 36
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 56
ggacgcgttt ttatctttt atgtaaatat atacta                                    36

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
attgtccaat ttttaaggct gcttttttca aattaatggg                                40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccattaattt gaaaaaagca gccttaaaaa ttggacaatc                                40

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcataaacaa gaaaagcagg ccgcccatca aattcataaa gttcc                          45

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggaactttat gaatttgatg ggcggcctgc ttttcttgtt tatgc                          45

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctcccggccg ccatggccgc                                                     20

<210> SEQ ID NO 62
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 62
gttggtgtgg cccagagact ct                                              22

<210> SEQ ID NO 63
<211> LENGTH: 6
<212> TYPE: PRT
<213> ORGANISM: Candida albicans

<400> SEQUENCE: 63

Lys Gln Ala Ala His Gln
1               5

<210> SEQ ID NO 64
<211> LENGTH: 6
<212> TYPE: PRT
<213> ORGANISM: Candida albicans

<400> SEQUENCE: 64

Lys Gln Lys Lys His Gln
1               5

<210> SEQ ID NO 65
<211> LENGTH: 8
<212> TYPE: PRT
<213> ORGANISM: Candida albicans

<400> SEQUENCE: 65

Ile Asp Val Val Asp Gln Ala Lys
1               5

<210> SEQ ID NO 66
<211> LENGTH: 8
<212> TYPE: PRT
<213> ORGANISM: Candida albicans

<400> SEQUENCE: 66

Ser Leu Leu Asp Ala Ala Val Lys
1               5

<210> SEQ ID NO 67
<211> LENGTH: 14
<212> TYPE: PRT
<213> ORGANISM: Candida albicans

<400> SEQUENCE: 67

Val Pro Thr Thr Asp Val Ser Val Val Asp Leu Thr Val Arg
1               5                   10

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcttgtgaaa ctccgtcgtg                                                 20

<210> SEQ ID NO 69
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agggacgtaa tcaacgcaag                                                20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tgtgcctggt gcttttacc                                                 19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ttagcccaag ctgccattac                                                20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tcatttgcca ccactaccac                                                20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tggcatagga ttgtgaccag                                                20

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gctggtggtt attggcaacg tgc                                            23

<210> SEQ ID NO 75
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 75
tggtaaggtg gtcacggcgg                                                   20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agatcaaggg caaacctcac                                                   20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ataggagcat ttggcacacc                                                   20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tacccaggcc aatacaaagg                                                   20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
taatgggctt gaccttggag                                                   20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ctaatgccgt cgtcagattg                                                   20

<210> SEQ ID NO 81
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 81
aacatctgga acgccatctc                                                   20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccattgacaa agccggttac                                                   20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ttagatgggt cggattctgg                                                   20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
aggtcgcaag caacaacaac                                                   20

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
aagaaacagc acgagaacca g                                                 21

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tcctgccact gaaccttccc cag                                               23

<210> SEQ ID NO 87
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 87
ccacttgagc cagctggagc g                                           21

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccaccaaaac caagtgctac                                             20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aactccagat gatcccgaag                                             20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tgtgcccact gaagtcaaag                                             20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gctttaccgg tgatttggtc                                             20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cacctcatgc tccaacaatg                                             20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic

```
        primer

<400> SEQUENCE: 93
gatgattctg gggctgattc                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tgctgaaagt tctgcaccag                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gcttcaacgg aaacagaagc                                               20
```